United States Patent
Wang et al.

(10) Patent No.: US 11,958,911 B2
(45) Date of Patent: Apr. 16, 2024

(54) ANTI-COAGULATION FACTOR XI ANTIBODY

(71) Applicant: SHANGHAI BENEMAE PHARMACEUTICAL CORPORATION, Shanghai (CN)

(72) Inventors: Wenyi Wang, Shanghai (CN); Quan Yu, Shanghai (CN); Xiaowu Liu, Shanghai (CN); John Liuzhong Xu, Shanghai (CN); Zhiqiang Du, Shanghai (CN)

(73) Assignee: Shanghai Benemae Pharmaceutical, Shanghai (CN)

( * ) Notice: Subject to any disclaimer, the term of this patent is extended or adjusted under 35 U.S.C. 154(b) by 0 days.

(21) Appl. No.: 16/537,427

(22) Filed: Aug. 9, 2019

(65) Prior Publication Data
US 2020/0024362 A1    Jan. 23, 2020

Related U.S. Application Data

(63) Continuation-in-part of application No. PCT/CN2017/119856, filed on Dec. 29, 2017, and a continuation of application No. PCT/CN2018/099638, filed on Aug. 9, 2018.

(30) Foreign Application Priority Data

Feb. 10, 2017   (CN) .......................... 201710073984.X

(51) Int. Cl.
*C07K 16/36*    (2006.01)
*A61P 7/04*    (2006.01)

(52) U.S. Cl.
CPC ................ *C07K 16/36* (2013.01); *A61P 7/04* (2018.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 2007/0282095 A1 | 12/2007 | Hosokawa et al. |
| 2011/0159006 A1 | 6/2011 | Hack |
| 2013/0171144 A1 | 6/2013 | Gruber et al. |
| 2015/0099298 A1 | 4/2015 | Wilmen et al. |
| 2017/0022292 A1 | 1/2017 | Eder et al. |

FOREIGN PATENT DOCUMENTS

| | | | |
|---|---|---|---|
| AU | 2016203944 | 7/2016 | |
| CA | 2872926 A1 * | 11/2013 | ................ A61P 7/02 |
| CN | 104684932 A | 6/2015 | |
| CN | 107922505 | 4/2018 | |
| CN | 108409863 | 8/2018 | |
| CN | 114478781 | 5/2022 | |
| RU | 2298416 | 5/2007 | |
| RU | 2372402 | 11/2009 | |
| WO | WO-9746100 A1 * | 12/1997 | ........... A61K 47/645 |
| WO | 2003007983 | 1/2003 | |
| WO | 2009067660 A2 | 5/2009 | |
| WO | 2009067660 A3 | 5/2009 | |
| WO | WO-2009154461 A1 * | 12/2009 | ................ A61P 7/02 |
| WO | WO-2010080623 A2 * | 7/2010 | ............. C07K 16/36 |
| WO | 2016207858 A1 | 12/2016 | |
| WO | WO-2017015619 A1 * | 1/2017 | ................ A61P 7/02 |
| WO | 2017162791 A1 | 9/2017 | |
| WO | 2018145533 A1 | 8/2018 | |

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al., J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Lescar, et al. Journal of Biological Chemistry 270.30 (1995): 18067-18076.*
Al-Horani, R. A. & Desai, U. R. Factor XIa inhibitors: A review of the patent literature. Expert Opin Ther Pat 26, 323-345 (2016).
Beck, A., Wurch, T., Bailly, C. &Corvaia, N. Strategies and challenges for the next generation of therapeutic antibodies. Nat Rev Immunol 10, 345-352 (2010).
Buller, H. R. et al. Factor XI antisense oligonucleotide for prevention of venous thrombosis. N Engl J Med 372, 232-240 (2015).
Chen, Z., Seiffert, D. & Hawes, B. Inhibition of Factor XI activity as a promising antithrombotic strategy. Drug Discov Today 19, 1435-1439 (2014).
Cheng, Q. et al. A role for factor XIIa-mediated factor XI activation in thrombus formation in vivo. Blood 116, 3981-3989 (2010).
Crosby, J. R. et al. Antithrombotic effect of antisense factor XI oligonucleotide treatment in primates. Arterioscler Thromb Vasc Biol 33, 1670-1678 (2013).
David, T. et al. Factor XIa-specific IgG and a reversal agent to probe factor XI function in thrombosis and hemostasis. Sci Transl Med 8, 353ra112 (2016).
Emsley et al., "Structure and function of factor XI" Blood 115(13): 2569-2577 (2010).
Gailani, D. & Gruber, A. Factor XI as a Therapeutic Target. Arterioscler Thromb Vasc Biol 36, 1316-1322 (2016).
Gailani, D., Lasky, N. M. &Broze, G. J., Jr. A murine model of factor XI deficiency. Blood Coagul Fibrinolysis 8, 134-144 (1997).
Gomez-Outes, A., et al. Discovery methods of coagulation-inhibiting drugs. Expert Opin Drug Discov 12, 1195-1205 (2017).

(Continued)

*Primary Examiner* — Michael Szperka
(74) *Attorney, Agent, or Firm* — Perkins Coie LLP

(57) ABSTRACT

Disclosed are antibodies thereof that bind to coagulation factor XI (FXI) and/or its activated form factor XIa (FXIa), or to fragments of FXI and/or FXIa, and compositions containing the antibodies. Also disclosed are methods of preparing the antibodies and use of the antibodies for treating and/or preventing coagulation associated conditions such as thrombosis and complications or conditions associated with thrombosis.

15 Claims, 21 Drawing Sheets

Specification includes a Sequence Listing.

(56) References Cited

OTHER PUBLICATIONS

He, R. et al. "Factor XI: Hemostasis, Thrombosis, and Antithrombosis" Thrombosisi Research, 2011, vol. 129. pp. 541-550.
Kleinschnitz, C. et al. Targeting coagulation factor XII provides protection from pathological thrombosis in cerebral ischemia without interfering with hemostasis. J Exp Med 203, 513-518 (2006).
Kouyama S, O. T., Hagio T, et al. Discovery of ONO-5450598, a highly orally bioavailable small molecule factor XIa inhibitor: the pharmacokinetic and pharmacological profiles. Res Pract Thromb Haemost 1 Suppl 1: PB 2139 (2017).
Kravtsov D.V. et al. Factor XI contributes to thrombin generation in the absence of factor XII. Blood 114, 452-458 (2009).
Liu, et al. "In vitro and in vivo modifications of recombinant and human IgG antibodies" mAbs, 2014, vol. 6, No. 5, pp. 1145-1154.
Liu, H. et al. "Coagulation Factor XI: A New Target for Antithrombotic Drug" Journal of Clinical and Pathological Research, 2016, vol. 36, No. 6, pp. 847-851. (English Abstract).
Matafonov, A. et al. "Evidence for Factor IX-Independent Roles for Factor IXa in Blood Coagulation" Journal of Thrombosis and Haemostasis, 2013, vol. 11, pp. 2118-2127.
Meijers J.C., Tekelenburg W.L., Bouma B.N., Bertina R.M., Rosendaal F.R. High levels of coagulation factor XI as a risk factor for venous thrombosis. N Engl J Med 342, 696-701 (2000).
Muller, F., Gailani, D. &Renne, T. Factor XI and XII as antithrombotic targets. Curr Opin Hematol 18, 349-355 (2011).
Peyvandi, F. et al. Coagulation factor activity and clinical bleeding severity in rare bleeding disorders: results from the European Network of Rare Bleeding Disorders. J Thromb Haemost 10, 615-621 (2012).
Preis, M. et al. Factor XI deficiency is associated with lower risk for cardiovascular and venous thromboembolism events. Blood 129, 1210-1215 (2017).
Puy, C., Rigg, R. A. & McCarty, O. J. The hemostatic role of factor XI. Thromb Res 141 Suppl 2, S8-S11 (2016).
Raskob, G. E. Thrombosis: a major contributor to global disease burden. Journal of Thrombosis and Haemostasis, pp. 1580-1590 (2014).
Salomon, O. &Seligsohn, U. New observations on factor XI deficiency. Haemophilia 10 Suppl 4, 184-187 (2004).
Seligsohn, U. Factor XI deficiency in humans. J Thromb Haemost 7 Suppl 1, 84-87 (2009).
Sun, Y.H. et al. "Identification of a Factor IX Binding Site on the Third Apple Domain of Activated Factor XI" The Journal of Biological Chemistry, 1996, vol. 271, No. 46, pp. 29023-29028.
Takahashi, M. et al. Inhibition of factor XI reduces thrombus formation in rabbit jugular vein under endothelial denudation and/or blood stasis. Thromb Res 125, 464-470 (2010).
Tucker, E. I. et al. Prevention of vascular graft occlusion and thrombus associated thrombin generation by inhibition of factor XI. Blood 113, 936-944 (2009).
Van Montfoort, M. L. et al. Two novel inhibitory anti-human factor XI antibodies prevent cessation of blood flow in a murine venous thrombosis model. Thromb Haemost 110, 1065-1073 (2013).
Wang et al., "Antibody Structure, Instability, and Formation" J. Pharm. Sciences 96(1): 1-26 (2007).
Wang, X. et al. Effects of factor IX or factor XI deficiency on ferric chloride induced carotid artery occlusion in mice. J Thromb Haemost 3, 695-702 (2005).
Wang, X. et al. Effects of factor XI deficiency on ferric chloride-induced vena cava thrombosis in mice. J Thromb Haemost 4, 1982-1988 (2006).
Wang, X. et al. Inhibition of Factor XIa Reduces the Frequency of Cerebral Microembolic Signals Derived from Carotid Arterial Thrombosis in Rabbits. J Pharmacol Exp Ther 360, 476-483 (2017).
Weitz, J. I. & Fredenburgh, J. C. Factors XI and XII as Targets for New Anticoagulants. Front Med (Lausanne) 4, 19 (2017).
Wong, P. C., et al. A small-molecule factor XIa inhibitor produces antithrombotic efficacy with minimal bleeding time prolongation in rabbits. J Thromb Thrombolysis 32, 129-137 (2011).
Wong, P. C. et al. In vitro, antithrombotic and bleeding time studies of BMS-654457, a small-molecule, reversible and direct inhibitor of factor XIa. J Thromb Thrombolysis 40, 416-423 (2015).
Yau, J. W. et al. Selective depletion of factor XI or factor XII with antisense oligonucleotides attenuates catheter thrombosis in rabbits. Blood 123, 2102-2107 (2014).
Younis, H. S. et al. Antisense inhibition of coagulation factor XI prolongs APTT without increased bleeding risk in cynomolgus monkeys. Blood 119, 2401-2408 (2012).
ISA, International Search Report and Written Opinion for International Patent Application No. PCT/CN2017/119856, dated Mar. 22, 2018. 15 pages with English translation.
ISA, International Search Report and Written Opinion for International Patent Application No. PCT/CN2018/099638, dated Apr. 30, 2019. 13 pages.
EPO, Partial Supplementary European Search Report for European Patent Application No. EP17895532.4, dated Nov. 4, 2020. 12 pages.
EPO, Extended European Search Report for European Patent Application No. EP17895532.4, dated Mar. 2, 2021. 10 pages.
Chen, C., et al., "Enhancement and destruction of antibody function by somatic mutation: unequal occurrence is controlled by V gene combinatorial associations," EMBO J. 14(12):2784-2794 (1995).
Pakula, A. A., "Genetic analysis of protein stability and function," Annu. Rev. Genet. 23:289-310 (1989).
Russian Patent Office, Second Office Action dated Feb. 17, 2022 for Russian Patent Application No. 2019128423, 7 pages with English translation.
Human Biology Knowledge Base, "Coagulation Factor XI (FXI, PTA)," humbio.ru/humbio/blood_dis/00115eb5.htm, Apr. 26, 2022, 4 pages.
Riott, Ivan, "Immunology," Mosby International Ltd, 1998, 9 pages.
Jabubke et al., "Amino Acids. Peptides. Proteins.," Moscow "Mir" 1985, 17 pages.

* cited by examiner

FIG. 13

```
MIFLYQVVHFILFTSVSGECVTQLLKDTCFEGGDITTVFTPSAKYCQVVCTYHPRCLLFT
FTAESPSEDPTRWFTCVLKDSVTETLPRVNRTAAISGYSFKQCSHQISACNKDIYVDLDM
KGINYNSSVAKSAQECQERCTDDVHCHFFTYATRQFPSLEHRNICLLKHTQTGTPTRITK
LDKVVSGFSLKSCALSNLACIRDIFPNTVFADSNIDSVMAPDAFVCGRICTHHPGCLFFT
FFSQEWPKESQRNLCLLKTSESGLPSTRIKKSKALSGFSLQSCRHSIPVFCHSSFYHDTD
FLGEELDIVAAKSHEACQKLCTNAVRCQFFTYTPAQASCNEGKGKCYLKLSSNGSPTKIL
HGRGGISGYTLRLCKMDNECTTKIKPRIVGGTASVRGEWPWQVTLHTTSPTQRHLCGGSI
IGNQWILTAAHCFYGVESPKILRVYSGILNQSEIKEDTSFFGVQEIIIHDQYKMAESGYD
IALLKLETTVNYTDSQRPICLPSKGDRNVIYTDCWVTGWGYRKLRDKIQNTLQKAKIPLV
TNEECQKRYRGHKITHKMICAGYREGGKDACKGDSGGPLSCKHNEVWHLVGITSWGEGCA
QRERPGVYTNVVEYVDWILEKTQAV
```

ANTI-COAGULATION FACTOR XI ANTIBODY

CROSS-REFERENCE TO RELATED APPLICATIONS

This application is a continuation in part of International Patent Application No. PCT/CN2017/119856, filed Dec. 29, 2017, which claims priority to Chinese Patent Application No. 201710073984.X, filed Feb. 10, 2017. This application is also a continuation of International Patent Application No. PCT/CN2018/099638, filed Aug. 9, 2018. The applications listed above are incorporated by reference in their entirety.

SEQUENCE LISTING

The instant application contains a Sequence Listing which has been submitted electronically in ASCII format and is hereby incorporated by reference in its entirety. Said ASCII copy, created on Aug. 9, 2019, is named 2019-08-09_CIP_Sequence_Listing_577838013 US and is 84,143 bytes in size.

TECHNICAL FIELD

This disclosure relates to antibodies capable of binding to the coagulation factor XI (FXI) and/or its activated form factor XIa (FXIa), and to fragments of FXI and/or FXIa, and uses thereof, including uses as anticoagulation agents for treating thrombosis that do not compromise hemostasis.

BACKGROUND

Thrombosis is a condition that involves blood clotting in a blood vessel, thereby blocking or obstructing blood flow in the affected area. This condition can lead to serious complications if the blood clots travel along the circulatory system to a crucial body part such as heart, brain, and lungs, causing heart attack, stroke, pulmonary embolism, etc. Thrombosis is the major cause of most strokes and myocardial infarctions, deep vein thrombosis (DVT), pulmonary embolism, and other cardiovascular events.[1,2] Thrombosis can be treated or prevented by anticoagulants such as low-molecular-weight heparin, warfarin, and Factor Xa direct inhibitors. The most common adverse effect of these currently available therapies is impairing haemostasis.[3-5] Therefore, these therapies are limited by the dose and patient compliance because patients are required to be closely monitored after the treatment.

There is a need for an effective thrombosis therapy or prophylaxis with minimal side effects. This disclosure satisfies the need in the art.

SUMMARY

Provided herein in certain embodiments are antibodies that bind to coagulation factor XI (FXI) and/or its activated form factor XIa (FXIa), and to fragments of FXI and/or FXIa. In some embodiments, the antibodies are monoclonal antibodies. In some embodiments, the antibodies are recombinant antibodies. In some embodiments, the antibodies are humanized antibodies. In some embodiments, the antibodies are immunologically active portions of immunoglobulin molecules, e.g., Fabs, Fvs, or scFvs. In some embodiments, the antibodies bind to the A3 domain of FXI and/or FXIa. In some embodiments, the antibodies include one or more CDRs consisting of or comprising the amino acid sequences of SEQ ID NOs: 11-16, 27-32, 43-48, 59-64, 75-80, 91-96, 107-112, 123-128, 139-144, 155-160, 171-176, and 187-192.

Provided herein is a pharmaceutical composition for treating and/or preventing thrombosis and/or complications or conditions associated with thrombosis. The pharmaceutical composition comprises one or more anti-FXI and/or anti-FXIa antibodies as disclosed herein. In some embodiments, the pharmaceutical composition further comprises one or more pharmaceutically acceptable adjuvants, carriers, excipients, preservatives, or a combination thereof.

Provided herein is a nucleic acid encoding an anti-FXI and/or anti-FXIa antibody as disclosed herein, or a functional fragment of either antibody, as well as a vector comprising the nucleic acid, and a host cell comprising the vector. In some embodiments, the vector is an expression vector that is capable of producing the antibody or a functional fragment thereof encoded by the nucleic acid in a host cell.

Provided herein is a kit comprising one or more anti-FXI and/or anti-FXIa antibodies as disclosed herein for use in treating and/or preventing thrombosis and/or complications or conditions associated with thrombosis. Alternatively, the kit comprises a pharmaceutical composition comprising one or more anti-FXI and/or anti-FXIa antibodies as disclosed herein for use in treating and/or preventing thrombosis and/or complications or conditions associated with thrombosis. In certain embodiments, the kit further comprises instructions for use.

Provided herein is a method of treating and/or preventing thrombosis and/or complications or conditions associated with thrombosis. The method includes administering to a subject in need thereof a therapeutically effective amount of one or more anti-FXI and/or anti-FXIa antibodies as disclosed herein. Alternatively, the method includes administering to a subject in need thereof a therapeutically effective amount of a pharmaceutical composition containing an anti-FXI antibody, an anti-FXIa antibody, or a functional fragment of either antibody.

Provided herein is a use of an anti-FXI and/or anti-FXIa antibody as disclosed herein formulating a medicament for treating and/or preventing thrombosis and/or complications or conditions associated with thrombosis.

Provided herein is a method of producing an anti-FXI and/or anti-FXIa antibody as disclosed herein. The method entails the steps of transforming a host cell with a vector comprising a nucleic acid encoding the antibody, and expressing the antibody in the host cell. The method can further include purifying the expressed antibody from the host cell. Additionally, the purified antibody can be subjected to modifications such that the modified recombinant antibody retains the activity of the corresponding human antibody. Alternatively, an antibody disclosed herein can be produced from culturing a hybridoma.

BRIEF DESCRIPTION OF THE DRAWINGS

FIGS. 4A-4C illustrate the concentration-response curves of antibodies h-19F6 (A), h-34F8 (B), and h-42A5 (C) inhibiting human FXIa from hydrolyzing S-2366.

FIG. 13 illustrates the amino acid sequence of human FXI (SEQ ID NO: 203).

FIG. 16A shows the effects of h-19F6 and h-42A5 on APTT in human plasma. FIG. 16B shows the effects of h-19F6 and h-42A5 on PT in human plasma.

FIG. 19A shows sensorgrams for h-19F6 captured on a sensor chip subjected to flows of indicated concentrations of FXI. FIG. 19B shows sensorgrams for h-42A5 captured on a sensor chip subjected to flows of indicated concentrations of FXI. FIG. 19C shows antibodies captured when test antibodies (5 µg/mL) flew through a sensor chip immobilized with equal amounts of 4 mutant FXIs in which the A1, A2, A3, or A4 domain was replaced with the corresponding domain from prekallikrein. A reported anti-FXI antibody, O1A6, was also tested a positive control. FIG. 19D shows that FXI was immobilized on a sensor chip. H-19F6 and h-42A5 (5 µg/ml) were successively injected into flow cells on the sensor surface at a flow rate of 30 µl/minute, and the response change was monitored. The experiment was performed twice, and a representative result is depicted.

FIG. 20A shows sensorgrams for h-19F6 captured on a sensor chip subjected to flows of indicated concentrations of FXIa. FIG. 20B shows sensorgrams for h-42A5 captured on a sensor chip subjected to flows of indicated concentrations of FXIa.

DETAILED DESCRIPTION

Figure 1A:
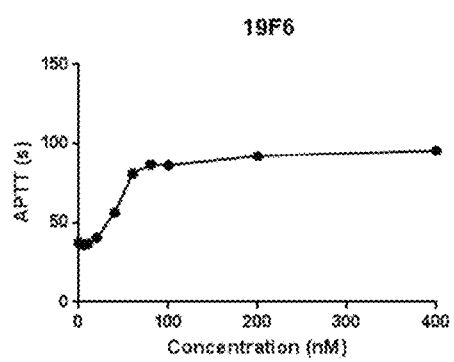
FIGS. 1A-1E illustrate the effects of five anti-FXI antibodies via APTT assay in human plasma. Human plasma supplemented with five different antibodies at a concentration ranging from 0 to 400 nM were tested in an APTT assay as described in Example 3. The five antibodies tested included 19F6 (A), 34F8 (B), 42A5 (C), 1A6 (D), and 14E11 (E). Antibodies 1A6 and 14E11 were used as positive controls in this experiment.
Figure 1B:
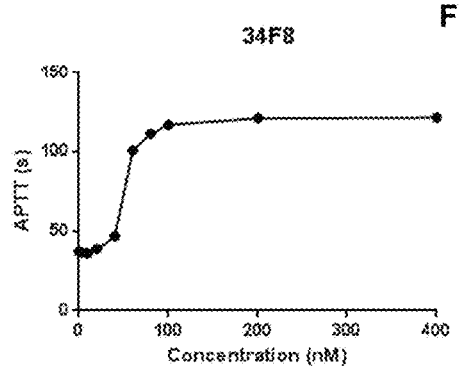
Figure 1D:
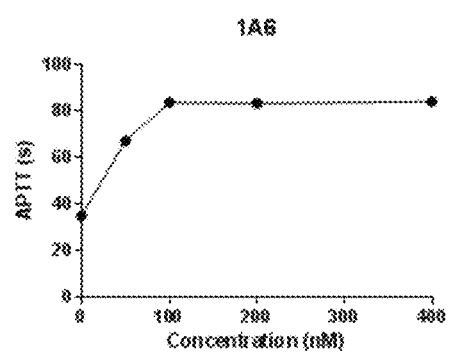
Figure 1C:
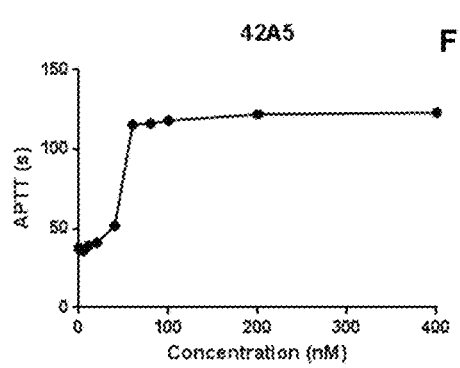
Figure 1E:
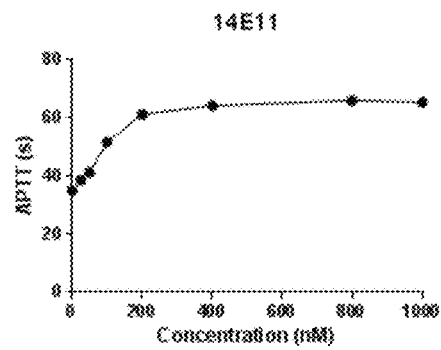

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Both intrinsic pathway and extrinsic pathway are involved in in vivo blood coagulation cascades. The intrinsic pathway, also called the contact activation pathway, is initiated by contact with a surface interface and results in activation of FXII. The intrinsic pathway also involves FXI, FIX and FVIII. The extrinsic pathway, also called the tissue factor (TF) pathway, is initiated by vascular injury and results in the formation of an activated complex of TF-FVIIa. These two pathways meet and activate the common pathway, leading to conversion of prothrombin to thrombin and eventually the formation of cross-linked fibrin clot. An ideal anticoagulant should be efficacious in preventing thrombosis without compromising haemostasis. Several lines of evidence suggest that the intrinsic coagulation pathway is important for the amplification phase of coagulation, whereas extrinsic and common pathways are more heavily involved in the initiation and propagation phases.[5-8] These findings indicate that the intrinsic pathway plays a minor role during normal haemostasis and that the inhibition of intrinsic pathway may provide antithrombotic benefits with low bleeding risk. FXI, a component of the intrinsic pathway, has recently become an attractive target, as it may have the potential to elicit anti-thrombosis effects without affecting bleeding.[3,5,6]

FXI can be activated by factor XIIa via the intrinsic pathway to FXIa, which in turn activates factor IX. Epidemiological studies have suggested that FXI deficiency in humans is associated with decreased risk of venous thromboembolism and stroke, whereas increased FXI levels are associated with increased risk.[9-11] In addition, FXI-deficient humans show a very low bleeding tendency.[12,13] Furthermore, mice deficient in FXI are protected against many types of thrombosis without increased bleeding.[14] Moreover, small-molecule inhibitors, antibodies and antisense oligonucleotides that inhibit FXI have demonstrated antithrombotic properties with no bleeding risk in many animal models of thrombosis.

The antibodies disclosed herein binds to FXI and/or FXIa and target the intrinsic pathway of blood coagulation. The structure of FXI and FXI's involvement in blood coagulation have been reported in various publications.[33]

Animal and clinical studies have suggested a robust association between FXI and thrombosis. FXI-deficient mice have been studied by many research teams and have displayed remarkable antithrombotic phenotypes in several models, including FeCl$_3$-induced arterial and deep vein thrombosis models, a pulmonary embolism model, and a cerebral artery occlusion del.[14,17,22,23] In human epidemiological studies, patients with congenital FXI deficiency are insusceptible to venous thromboembolism (VTE) orischaemic stroke, and subjects with higher levels of FXI are at greater risk for VTE and ischaemic stroke than those with lower levels.[9-11] For physiological haemostasis, the role of FXI appears dispensable. FXI-deficient mice do not show excessive bleeding, as their tail-bleeding times are comparable to those of wild-type animals.[23,24] In addition, severely FXI-deficient patients do not exhibit spontaneous bleeding, although they may display a variable bleeding tendency during surgical operations.[12,13] Combination of two or more anti-thrombotics are widely used clinically. A previous study showed that aspirin caused a similar bleeding tendency in wild-type and FXI-deficient mice, suggesting that targeting FXI might still be safe even in the presence of other anti-thrombotic therapies.[14]

All of the above-mentioned findings indicate that FXI/FXIa is a safe drug target for treating thrombosis-related diseases without compromising haemostasis. Thus, many approaches have been applied to target FXI/FXIa for developing therapeutics for treating thrombosis, such as antibodies, oligonucleotides, and small-molecule inhibitors.[5] As described herein, antibody-type blockers of FXI/FXIa were generated. The advantages of antibodies include fast-acting properties and a low frequency of dosing, and a major weakness of antibodies is their potential immunogenicity.[25] At least two test antibodies were humanized before conducting in vivo studies. Two humanized antibodies, h-19F6 and h-42A5, demonstrated very high affinity to human FXI/FXIa. Interestingly, they bind different regions but the same domain (A3) of FXI. Without bound by any theory, the antibodies might both inhibit FXIa activity but have no effect on FXI activation mediated by either FXIIa or thrombin.

Various types of FXI/FXIa inhibitors have prolonged APTT and exhibited antithrombotic effects in different models. Anti-FXI antibody 14E11 increased APTT by approximately 1.3-fold and reduced thrombosis in exteriorized femoral arteriovenous shunts in baboons.[17] An antisense oligonucleotide inhibiting FXI expression reduced plasma FXI levels by approximately 50% and decreased thrombus formation in baboons.[26,27] In addition, an orally bioavailable small-molecule FXIa inhibitor, ONO-5450598, significantly inhibited thrombosis formation in monkey models of thrombosis.[28] Furthermore, the antithrombotic effects of therapeutics targeting FXI/FXIa have also been confirmed in many non-primate animal models, such as mouse and rabbit thrombosis models.[19, 29-31] A recent clinical trial showed that an antisense oligonucleotide targeting FXI prevented venous thrombosis in patients undergoing knee arthroplasty.[32] As demonstrated in the working examples, two distinctive primate thrombosis models were used to evaluate the antithrombotic effects of h-19F6 and h-42A5. In the AV shunt thrombosis models, both antibodies decreased thrombosis formation in a dose-dependent manner. In FeCl$_3$-induced thrombosis models, both antibodies extended the time for thrombosis-led vessel occlusion. These results provide further evidence of the anti-thrombotic roles of FXI/FXIa inhibitors. The dose-dependent reduction of thrombosis formation for h-19F6 and h-42A5 in AV shunt thrombosis models suggest that thrombosis formation may negatively correlate with the degree of FXI inhibition, which can be indicated by APTT prolongation. Because h-42A5 is more potent than h-19F6 in prolonging APTT, the comparison of antithrombotic effects between h-42A5 and h-19F6 in the FeCl$_3$-induced thrombosis models could also lead to such an indication. Thus, more intense inhibition of FXI/FXIa, as indicated by a longer APTT, by FXI/FXIa inhibitors may result in better anti-thrombotic outcomes.

Bleeding risk is the most concerning issue in developing antithrombotic agents. As previously mentioned, FXI-deficient patients may show a bleeding tendency under surgical settings. It is unclear to what extent plasma FXI activity inhibition is still safe in terms of bleeding risk. As demonstrated in the working examples, the bleeding risk of intensive inhibition of FXI/FXIa by h-19F6 and h-42A5 was tested in the same monkeys used in thrombosis experiments. In AV shunt thrombosis animals, no bleeding tendency was observed as the treating dose of h-19F6 or h-42A5 escalated, suggesting that bleeding risk may be independent of the extent of FXI inhibition. In FeCl$_3$-induced thrombosis animals, neither h-19F6 nor h-42A5 treatment caused excessive bleeding. h-42A5 treatment resulted in an approximately 2-fold elevation of plasma APTT, which indicated more than 99% FXI inhibition. Previous studies have never evaluated bleeding risk under such intensive APTT-prolongation and high-FXI-inhibition conditions. The antisense oligonucleotide ISIS416856 only caused 30% elevation of APTT when its bleeding risk was evaluated.[26] In other bleeding risk-evaluation studies in primates, a high potent anti-FXI antibody, aXIMab, caused an approximately 1-fold increase in APTT (from 30.5 s to 65.6 s).[26] Thus, the results described herein demonstrate that intensive inhibition of FXI/FXIa does not increase bleeding risk in primates. Thus, FXI can be used as a drug target for thrombosis treatment.

Anti-FXI or Anti-FXIa Antibodies

Provided herein are antibodies that bind to FXI, FXIa, and/or a fragment of FXI or FXIa and inhibit the formation of blood clot. These antibodies are capable of binding to FXI, FXIa, and/or a fragment of FXI or FXIa (e.g., a fragment comprising the A3 domain) and exhibiting an inhibitory effect at a concentration that is much lower than the maximum safety dose. For example, in some embodiments a dose of the antibody between 0.1 mg/kg i.v. and 3 mg/kg i.v. exhibits an inhibitory effect on conversion of FXI to FXIa in cynomolgus monkeys. Moreover, the antibodies disclosed herein can be used as anticoagulation agents with superior safety due to their minimal risk of causing bleeding versus conventional anticoagulation agents such as heparin.

As demonstrated in the working examples, many anti-human FXI antibodies were generated by immunizing rats with human FXI to identify antibodies with anticoagulation properties. A dozen such antibodies were identified, and some of which were humanized for further development. The humanized rat anti-human FXI antibodies, such as h-19F6 and h-42A5 antibodies, were characterized in vitro and in vivo. In the in vitro studies, the humanized antibodies inhibited activated FXI (FXIa)-mediated hydrolysis of factor IX but not factor XIIa-induced FXI activation. The binding properties of the antibodies to FXI were determined, and the dissociation constants (KD) for h-19F6 and h-42A5 were 22 pM and 35 pM, respectively. These two antibodies bind different sites in the A3 domain of FXI. In the in vivo studies, two distinct primate thrombosis models were used to evaluate the anti-thrombotic effects and bleeding risks of the humanized antibodies. In arteriovenous (AV) shunt thrombosis models, both antibodies dose-dependently decreased thrombus formation without causing bleeding. In FeCl3-induced thrombosis models, both antibodies extended the time to thrombosis-mediated vessel occlusion, and neither antibody increased bleeding. The two antibodies showed anti-thrombotic efficacy without compromising haemostasis in primates, further confirming that targeting FXI can be used for treating thrombosis.

As used herein, the term "comprising" with regard to a composition or method means that the composition or method includes at least the recited elements. The term "consisting essentially of" means that the composition or method includes the recited elements, and may further include one or more additional elements that do not materially affect the novel and basic characteristics of the composition or method. For example, a composition consisting essentially of recited elements may include those recited elements plus one or more trace contaminants from the isolation and purification method, pharmaceutically acceptable carriers such as phosphate buffered saline, preservatives, and the like. The term "consisting of" means the composition or method includes only the recited elements. Embodiments defined by each of the transitional terms are within the scope of this invention.

The term "antibody" as used herein refers to an immunoglobulin molecule or an immunologically active portion thereof that specifically binds to, or is immunologically reactive with a particular antigen, for example, FXI, FXIa, or a particular domain or fragment of FXI or FXIa, e.g., the A3 domain. In certain embodiments an antibody for use in the present methods, compositions, and kits is a full-length immunoglobulin molecule, which comprises two heavy chains and two light chains, with each heavy and light chain containing three complementary determining regions (CDRs). The term "antibody," in addition to natural antibodies, also includes genetically engineered or otherwise modified forms of immunoglobulins, such as synthetic antibodies, intrabodies, chimeric antibodies, fully human antibodies, humanized antibodies, peptibodies and heteroconjugate antibodies (e.g., bispecific antibodies, multispecific antibodies, dual-specific antibodies, anti-idiotypic antibodies, diabodies, triabodies, and tetrabodies). The antibodies disclosed herein can be monoclonal antibodies or polyclonal antibodies. In those embodiments where an antibody is an immunologically active portion of an immunoglobulin molecule, the antibody may be, for example, a Fab, Fab', Fv, Fab' F(ab')$_2$, disulfide-linked Fv, single chain Fv antibody (scFv), single domain antibody (dAb), or diabody. The antibodies disclosed herein, including those that are immunologically active portion of an immunoglobulin molecule, retain the ability to bind a specific antigen, for example FXI or FXIa, or to bind a specific fragment of FXI or FXIa such as the A3 domain.

In some embodiments, the anti-FXI and/or anti-FXIa antibodies disclosed herein have undergone post-translational modifications such as phosphorylation, methylation, acetylation, ubiquitination, nitrosylation, glycosylation, or lipidation associated with expression in a mammalian cell line, including a human or a non-human host cell. Techniques for producing recombinant antibodies and for in vitro and in vivo modifications of recombinant antibodies are known in the art. See, e.g., Liu et al., *mAbs* 6(5): 1145-1154 (2014), the content of which is incorporated by reference.

Also disclosed are polynucleotides or nucleic acids encoding the anti-FXI and/or anti-FXIa antibodies disclosed herein. In some embodiments, the polynucleotide or nucleic acid includes DNA, mRNA, cDNA, plasmid DNA. The nucleic acid encoding the antibody or a functional fragment thereof disclosed herein can be cloned into a vector, such as a pTT5 mammalian expression vector, which may further include a promoter and/or other transcriptional or translational control elements such that the nucleic acid can be expressed to produce the antibody or the functional fragment thereof.

The nucleic acid (DNA) and/or amino acid (PRT) sequences, including the sequences of the VH and VL and CDRs, of some examples of the antibodies disclosed herein are listed in Table 1 below.

TABLE 1

| Description | SEQ ID NO | Type | Sequence |
|---|---|---|---|
| 3G12-VL | 1 | DNA | GACATTGTGCTGACCCAATCTCCAGCTTCTTTGGC TGTGTCTCTAGGGCAGAGGGCCACCATCTCCTGC AGAGCCAGCGAAAGTGTTGATAATTATGCCATTAG TTTTATGAACTGGTTCCAACAGAAACCAGGACAGC CACCCAAACTCCTCATCTATGCTGCATCAACCTA GGATCCGGGGTCCCTGCCAGGTTTAGTGGCAGTG GGTCTGGGACAGACTTCAGCCTCAACATCCATCCT ATGGAGGAGGATGATACTGCAATGTATTTCTGTCA GCAAGATAAGGAGGTTCCGTGGACGTTCGGTGGA GGCACCGAGCTGGAAATCAAA |
| 3G12-VH | 2 | DNA | CAGGTCACTCTGAAAGAGTCTGGCCCTGGGATATT GCAGCCCTCCCAGACCCTCAGTCTGACTTGTTCTT TCTCTGGGTTTTCACTGAACACTCCTGGTATGGGT GTGAGCTGGATTCGTCAGCCTTCAGGAAAGGGTC TGGAATGGCTGGCACACATTTACTGGGATGATGAC AAGCGCTTTAACCCATCCCTGAAGAGCCGACTCAC AATCTCCAAGGATACCTCAGAGATCAGGTATTCC TCATGATCACCAGTGTGGACACTGCAGATTCTGCC ACATACTTCTGTGCTCGAAAAGGCCGCGGGCCCT TTACTTACTGGGGCCAAGGGACTCTGGTCACTGTC TCTTCA |
| 3G12-CDR-L1 | 3 | DNA | AGAGCCAGCGAAAGTGTTGATAATTATGCCATTAG TTTTATGAAC |
| 3G12-CDR-L2 | 4 | DNA | GCTGCATCCAACCTAGGATCC |
| 3G12-CDR-L3 | 5 | DNA | CAGCAAGATAAGGAGGTTCCGTGGACG |
| 3G12-CDR-H1 | 6 | DNA | ACTCCTGGTATGGGTGTGAGC |
| 3G12-CDR-H2 | 7 | DNA | CACATTTACTGGGATGATGACAAGCGCTTTAACCC ATCCCTGAAGAGC |
| 3G12-CDR-H3 | 8 | DNA | AAAGGCCGCGGGCCCTTTACTTAC |
| 3G12-VL | 9 | PRT | DIVLTQSPASLAVSLGQRATISCRASESVDNYAISFM NWFQQKPGQPPKLLIYAASNLGSGVPARFSGSGSG TDFSLNIHPMEEDDTAMYFCQQDKEVPWTFGGGTE LEIK |
| 3G12-VH | 10 | PRT | QVTLKESGPGILQPSQTLSLTCSFSGFSLNTPGMGV SWIRQPSGKGLEWLAHIYWDDDKRFNPSLKSRLTIS KDTSRDQVFLMITSVDTADSATYFCARKGRGPFTYW GQGTLVTVSS |
| 3G12-CDR-L1 | 11 | PRT | RASESVDNYAISFMN |
| 3G12-CDR-L2 | 12 | PRT | AASNLGS |
| 3G12-CDR-L3 | 13 | PRT | QQDKEVPWT |
| 3G12-CDR-H1 | 14 | PRT | TPGMGVS |
| 3G12-CDR-H2 | 15 | PRT | HIYWDDDKRFNPSLKS |
| 3G12-CDR-H3 | 16 | PRT | KGRGPFTY |
| 5B2-VL | 17 | DNA | GACATTGTGCTGACCCAATCTCCAGCCTCTTTGGC TGTGTCTCTAGGGCAGAGGGCCACCATCTCCTGC AGAGCCAGCGAAAGTGTTGATAATTATGGCATTAG TTTTCTGAACTGGTTCCAACAGAAACCAGGACAGC CACCCAAACTCCTCATCTATGCTGCATCCAATCTA GGATCCGGGGTCCCTGCCAGGTTTAGTGGCAGTG GGTCTGGGACAGACTTCAGCCTCAACATCCATCCT ATGGAGGAGGATGATACTGCAATGTATTTCTGTCA GCAAGATAAGGGGGTTCCGTGGACGTTCGGTGGA GGCACCAAGCTGGAAATGAAA |
| 5B2-VH | 18 | DNA | CAGGTTACTCTGAAAGAGTCTGGCCCTGGGATATT GCAGCCCTCCCAGACCCTCAGTCTGACTTGTTCTT TCTCTGGGTTTTCACTGAACACTTCTGGTATGGGT GTGAGCTGGATTCGTCAGCCTTCAGGAAAGGGTC TGGAGTGGCTGGCACACATTTACTGGGATGATGA |

TABLE 1-continued

Antibody Sequences

| Description | SEQ ID NO | Type | Sequence |
|---|---|---|---|
| | | | CAAGCGCTATAAACCATCCCTGAAGAGCCGGCTC ACAATCTCCAAGGATACCTCCAGAAACCAGGTATT CCTCATGATCACCAGTGTGGACACTGCAGATACTG CCACATACTACTGTGTTCGAAAAGGCCGCGGGCC CTTTGCTAACTGGGGCCAAGGGACTCTGGTCACT GTCTCTGCA |
| 5B2-CDR-L1 | 19 | DNA | AGAGCCAGCGAAAGTGTTGATAATTATGGCATTAG TTTTCTGAAC |
| 5B2-CDR-L2 | 20 | DNA | GCTGCATCCAATCTAGGATCC |
| 5B2-CDR-L3 | 21 | DNA | CAGCAAGATAAGGGGGTTCCGTGGACG |
| 5B2-CDR-H1 | 22 | DNA | ACTTCTGGTATGGGTGTGAGC |
| 5B2-CDR-H2 | 23 | DNA | CACATTTACTGGGATGATGACAAGCGCTATAAACC ATCCCTGAAGAGC |
| 5B2-CDR-H3 | 24 | DNA | AAAGGCCGCGGGCCCTTTGCTAAC |
| 5B2-VL | 25 | PRT | DIVLTQSPASLAVSLGQRATISCRASESVDNYGISFL NWFQQKPGQPPKLLIYAASNLGSGVPARFSGSGSGT DFSLNIHPMEEDDTAMYFCQQDKGVPWTFGGGTKLE MK |
| 5B2-VH | 26 | PRT | QVTLKESGPGILQPSQTLSLTCSFSGFSLNTSGMGV SWIRQPSGKGLEWLAHIYWDDDKRYKPSLKSRLTIS KDTSRNQVFLMITSVDTADTATYYCVRKGRGPFANW GQGTLVTVSA |
| 5B2-CDR-L1 | 27 | PRT | RASESVDNYGISFLN |
| 5B2-CDR-L2 | 28 | PRT | AASNLGS |
| 5B2-CDR-L3 | 29 | PRT | QQDKGVPWT |
| 5B2-CDR-H1 | 30 | PRT | TSGMGVS |
| 5B2-CDR-H2 | 31 | PRT | HIYWDDDKRYKPSLKS |
| 5B2-CDR-H3 | 32 | PRT | KGRGPFAN |
| 7C9-VL | 33 | DNA | GACATCCAGATGACCCAGTCTCCATCCTCCTTATC TGCCTCTCTGGGAGAAAGAGTCAGTCTCACTTGTC GGGCAAGTCAGGACATTGATATTCGCTTAAACTGG CTTCGACAGGAACCAGATGGAACTATTAAACGCCT GATCTACGCCACATCCAGTTTAGATTCTGGTGTCC CCAAAAGGTTCAGTGGCAGTAGGTCTGGGTCAGA TTATTCTCTCACCATCAGCAGCCTTGAGTCTGAAG ATTTTGTTGACTATTACTGTCTACAATATGCTAGTT CTCCATTCACGTTCGGCTCGGGGACAAAGTTGGA AATAAAA |
| 7C9-VH | 34 | DNA | CAGATCCAGTTGGTGCAGTCTGGACCTGAACTGA AGAAGCCTGGAGAGACCGTCAAGATCTCCTGCAA GGCTTCTGGGTATATTTTCACAGACTATGGAATGA ACTGGGTGAAGCAGGCTCCAGGAAAGGGTTTAAA GTGGATGGGCTGGATAAACACCTACACTGGAGAG CCAACATATGCTGATGACTTCAAGGGACGGTTTGT CTTCTCTTTGGAAACCTCTGCCAGCACTGCCTATT TACAGATCAACAACCTCAAAAATGAGGACACGGCT ACATTTTTCTGTGCAAGAAGGAGGATGGGTTATGC TGTGGACTACTGGGGTCAAGGAACCTCAGTCACC GTCTCCTCA |
| 7C9-CDR-L1 | 35 | DNA | CGGGCAAGTCAGGACATTGATATTCGCTTAAAC |
| 7C9-CDR-L2 | 36 | DNA | GCCACATCCAGTTTAGATTCT |
| 7C9-CDR-L3 | 37 | DNA | CTACAATATGCTAGTTCTCCATTCACG |
| 7C9-CDR-H1 | 38 | DNA | GACTATGGAATGAAC |

TABLE 1-continued

Antibody Sequences

| Description | SEQ ID NO | Type | Sequence |
|---|---|---|---|
| 7C9-CDR-H2 | 39 | DNA | TGGATAAACACCTACACTGGAGAGCCAACATATGC TGATGACTTCAAGGGA |
| 7C9-CDR-H3 | 40 | DNA | AGGAGGATGGGTTATGCTGTGGACTAC |
| 7C9-VL | 41 | PRT | DIQMTQSPSSLSASLGERVSLTCRASQDIDIRLNWLR QEPDGTIKRLIYATSSLDSGVPKRFSGSRSGSDYSLT ISSLESEDFVDYYCLQYASSPFTFGSGTKLEIK |
| 7C9-VH | 42 | PRT | QIQLVQSGPELKKPGETVKISCKASGYIFTDYGMNW VKQAPGKGLKWMGWINTYTGEPTYADDFKGRFVFS LETSASTAYLQINNLKNEDTATFFCARRRMGYAVDY WGQGTSVTVSS |
| 7C9-CDR-L1 | 43 | PRT | RASQDIDIRLN |
| 7C9-CDR-L2 | 44 | PRT | ATSSLDS |
| 7C9-CDR-L3 | 45 | PRT | LQYASSPFT |
| 7C9-CDR-H1 | 46 | PRT | DYGMN |
| 7C9-CDR-H2 | 47 | PRT | WINTYTGEPTYADDFKG |
| 7C9-CDR-H3 | 48 | PRT | RRMGYAVDY |
| 7F1-VL | 49 | DNA | GACATTGTGCTGACCCAATCTCCAGCTTCTTTGGC TGTGTCTCTAGGGCAGAGGGCCACCATCTCCTGC AGAGCCAGCGAAAGTGTTGATAATTATGCCATTAG TTTTATGAATTGGTTCCAACAGAAACCAGGACAGC CACCCAAACTCCTCATCTATGCTGCATCCAACCTA GGATCCGGGGTCCCTGCCAGGTTTAGTGGCAGTG GGTCTGGGACAGACTTCAGCCTCAACATCCATCCT ATGGAGGAGGATGATACTGCAATGTATTTCTGTCA GCAAGATAAGGAGGTTCCGTGGACGTTCGGTGGA GGCACCAAGCTGGAGCTGAAA |
| 7F1-VH | 50 | DNA | CAGGTTACTCTGAAAGAGTCTGGCCCTGGGATAG TGCAGCCCTCCCAGACCCTCAATCTGACTTGTTCT TTCTCTGGATTTTCACTGAGCACTTCTGGTATGGG TGTGAGCTGGATTCGTCAGCCTTCAGGAAAGGGT CTGGATTGGCTGGCACACATTTACTGGGATGATGA CAAGCGCTATAACCCATCCCTGATGAGCCGGCTC ACAATCTCCAAGGATACCTCCAGAAACCAGGTATT CCTCATGATCACCAGTGTGGACACTGCAGATACTG CCACATACTACTGTGCTCGAAAAGGCCGCGGGCC CTTTGCTTACTGGGGCCAAGGGACTCTGGTCACT GTCTCTTCA |
| 7F1-CDR-L1 | 51 | DNA | AGAGCCAGCGAAAGTGTTGATAATTATGCCATTAG TTTTATGAAT |
| 7F1-CDR-L2 | 52 | DNA | GCTGCATCCAACCTAGGATCC |
| 7F1-CDR-L3 | 53 | DNA | CAGCAAGATAAGGAGGTTCCGTGGACG |
| 7F1-CDR-H1 | 54 | DNA | ACTTCTGGTATGGGTGTGAGC |
| 7F1-CDR-H2 | 55 | DNA | CACATTTACTGGGATGATGACAAGCGCTATAACCC ATCCCTGATGAGC |
| 7F1-CDR-H3 | 56 | DNA | AAAGGCCGCGGGCCCTTTGCTTAC |
| 7F1-VL | 57 | PRT | DIVLTQSPASLAVSLGQRATISCRASESVDNYAISFM NWFQQKPGQPPKLLIYAASNLGSGVPARFSGSGSG TDFSLNIHPMEEDDTAMYFCQQDKEVPWTFGGGTK LELK |
| 7F1-VH | 58 | PRT | QVTLKESGPGIVQPSQTLNLTCSFSGFSLSTSGMGV SWIRQPSGKGLDWLAHIYWDDDKRYNPSLMSRLTIS KDTSRNQVFLMITSVDTADTATYYCARKGRGPFAYW GQGTLVTVSS |
| 7F1-CDR-L1 | 59 | PRT | RASESVDNYAISFMN |

TABLE 1-continued

Antibody Sequences

| Description | SEQ ID NO | Type | Sequence |
|---|---|---|---|
| 7F1-CDR-L2 | 60 | PRT | AASNLGS |
| 7F1-CDR-L3 | 61 | PRT | QQDKEVPWT |
| 7F1-CDR-H1 | 62 | PRT | TSGMGVS |
| 7F1-CDR-H2 | 63 | PRT | HIYWDDDKRYNPSLMS |
| 7F1-CDR-H3 | 64 | PRT | KGRGPFAY |
| 13F4-VL | 65 | DNA | CAGTTCACGCTGACTCAACCAAAGTCCGTGTCAG GATCTTTAAGAAGCACTATCACCATTCCCTGTGAG CGCAGCAGTGGTGACATTGGAGATAGCTATGTGA GCTGGTACCAACAACACTTGGGAAGACCCCCCAT CAATGTGATCTATGCTGATGATCAAAGACCATCTG AAGTGTCTGCTCGGTTCTCGGGCTCCATCGACAG CTCCTCTAACTCAGCCTCACTGACCATCACTAATC TACAGATGGATGATGAGGCCGACTACTTCTGTCAG TCTTACGATACTTATATGGATGTTGTGTTCGGTGG TGGAACCAAGCTCAATGTCCTA |
| 13F4-VH | 66 | DNA | GAGGTGCAGCTGAAGGAATCAGGACCTGGTCTGG TGCAGCCCTCACAGACCCTGTCCCTCACCTGCAC TGTCTCTGGATTCTCATTAACGGACTACAGTGTAC ACTGGGTTCGCCAGCCTCCAGGAAAAGGTCTGGA GTGGATGGGAGTAATGTGGAGTGGTGGAAGCACA GCATATAATCCAGCTCTCACATCCCGACTGACCAT TAGCAGGGACACCTCCAAGAGCCAAGTTTTCTTAA AAATGAACAGTCTGCAAACTGAAGATACAGCCATT TACTACTGTACCAGAGCACCTTTTAACAACTGGGG CAATTGGCTTCCTTACTGGGGCCAAGGCACTCTG GTCACTGTCTCTTCA |
| 13F4-CDR-L1 | 67 | DNA | GAGCGCAGCAGTGGTGACATTGGAGATAGCTATG TGAGC |
| 13F4-CDR-L2 | 68 | DNA | GCTGATGATCAAAGACCATCT |
| 13F4-CDR-L3 | 69 | DNA | CAGTCTTACGATACTTATATGGATGTTGTG |
| 13F4-CDR-H1 | 70 | DNA | GACTACAGTGTACAC |
| 13F4-CDR-H2 | 71 | DNA | GTAATGTGGAGTGGTGGAAGCACAGCATATAATCC AGCTCTCACATCC |
| 13F4-CDR-H3 | 72 | DNA | GCACCTTTTAACAACTGGGGCAATTGGCTTCCTTA C |
| 13F4-VL | 73 | PRT | QFTLTQPKSVSGSLRSTITIPCERSSGDIGDSYVSWY QQHLGRPPINVIYADDQRPSEVSARFSGSIDSSSNSA SLTITNLQMDDEADYFCQSYDTYMDVVFGGGTKLNV L |
| 13F4-VH | 74 | PRT | EVQLKESGPGLVQPSQTLSLTCTVSGFSLTDYSVHW VRQPPGKGLEWMGVMWSGGSTAYNPALTSRLTISR DTSKSQVFLKMNSLQTEDTAIYYCTRAPFNNWGNW LPYWGQGTLVTVSS |
| 13F4-CDR-L1 | 75 | PRT | ERSSGDIGDSYVS |
| 13F4-CDR-L2 | 76 | PRT | ADDQRPS |
| 13F4-CDR-L3 | 77 | PRT | QSYDTYMDVV |
| 13F4-CDR-H1 | 78 | PRT | DYSVH |
| 13F4-CDR-H2 | 79 | PRT | VMWSGGSTAYNPALTS |
| 13F4-CDR-H3 | 80 | PRT | APFNNWGNWLPY |
| 19F6-VL | 81 | DNA | CAATTCACGCTGACTCAACCAAAGTCCGTGTCAGG CTCTTTAAGAAGCACTATCACCATTCCCTGTGAGC GCAGCAGTGGTGACATTGGAGATAGCTATGTGAG CTGGTACCAGCAACACTTGGGAAGACCCCCCATC AATGTGATCTATGCTGATGATCAAAGACCATCTGA |

TABLE 1-continued

Antibody Sequences

| Description | SEQ ID NO | Type | Sequence |
|---|---|---|---|
| | | | AGTGTCTGATCGGTTCTCGGGCTCCATCGACACCT<br>CCTCTAACTCAGCCTCACTGACCATCACTAATCTG<br>CAGATGGATGATGCGGCCGACTACTTCTGTCAGT<br>CTTACGATAGTAATATTGATTTTAACCCTGTTTTCG<br>GTGGTGGAACCAAGCTCACTGTCCTA |
| 19F6-VH | 82 | DNA | GAGGTGCAGCTGGTGGAGTCTGGTGGAGGCTTAG<br>TGCAGCCTGGAAGGTCTCTGAGACTCTCCTGTACA<br>GCCTCAGGATTCACTTTCAGTAAATATGTCATGGC<br>CTGGGTCCGCCAGGCTCCAACGAAGGGGCTGGA<br>GTGGGTCGCATCCATTAATTATGATGGTAGTACCA<br>CTTACTATCGAGACTCCGTGCAGGGCCGGTTCAC<br>TCTCTCCAGAGATAATGCAAAAACCACCCTATACC<br>TGCAAATGGACAGTCTGAGGTCTGAGGACACGGC<br>CACTTATTACTGTGCAAGGCACCCTTTTAACAACTT<br>CGGGATTTGGTTTGCTTACTGGGGCCAAGGCACT<br>CTGGTCACTGTCTCTTCA |
| 19F6-CDR-L1 | 83 | DNA | GAGCGCAGCAGTGGTGACATTGGAGATAGCTATG<br>TGAGC |
| 19F6-CDR-L2 | 84 | DNA | GCTGATGATCAAAGACCATCT |
| 19F6-CDR-L3 | 85 | DNA | CAGTCTTACGATAGTAATATTGATTTTAACCCTGTT |
| 19F6-CDR-H1 | 86 | DNA | AAATATGTCATGGCC |
| 19F6-CDR-H2 | 87 | DNA | TCCATTAATTATGATGGTAGTACCACTTACTATCGA<br>GACTCCGTGCAGGGC |
| 19F6-CDR-H3 | 88 | DNA | CACCCTTTTAACAACTTCGGGATTTGGTTTGCTTAC |
| 19F6-VL | 89 | PRT | QFTLTQPKSVSGSLRSTITIPCERSSGDIGDSYVSWY<br>QQHLGRPPINVIYADDQRPSEVSDRFSGSIDTSSNSA<br>SLTITNLQMDDAADYFCQSYDSNIDFNPVFGGGTKLT<br>VL |
| 19F6-VH | 90 | PRT | EVQLVESGGGLVQPGRSLRLSCTASGFTFSKYVMA<br>WVRQAPTKGLEWVASINYDGSTTYYRDSVQGRFTL<br>SRDNAKTTLYLQMDSLRSEDTATYYCARHPFNNFGI<br>WFAYWGQGTLVTVSS |
| 19F6-CDR-L1 | 91 | PRT | ERSSGDIGDSYVS |
| 19F6-CDR-L2 | 92 | PRT | ADDQRPS |
| 19F6-CDR-L3 | 93 | PRT | QSYDSNIDFNPV |
| 19F6-CDR-H1 | 94 | PRT | KYVMA |
| 19F6-CDR-H2 | 95 | PRT | SINYDGSTTYYRDSVQG |
| 19F6-CDR-H3 | 96 | PRT | HPFNNFGIWFAY |
| 21F12-VL | 97 | DNA | GATGTCCGGATGACACAGTCTCCAGCTTCCCTGTC<br>TGCATCTCTGGGAGAAACTGTCAACATCGAATGTC<br>TAGCAAGTGAGGACATTTACAGTGATTTAGCATGG<br>TATCAGCAGAAGCCAGGGAAATCTCCTCAGCTCCT<br>GATCTATAATGCAAATAGTCTACAAAATGGGGTCC<br>CTTCACGGTTTAGTGGCAGTGGTTCTGGCACGCA<br>GTATTCTCTAAAAATATCCACCCTGCAATCTGAAGA<br>TGTCGCGACTTATTTCTGTCAACAATATAGCAATTA<br>TCGTCGGACGTTCGGTGGAGGCACCAAGCTGGAA<br>ATCAAT |
| 21F12-VH | 98 | DNA | GAGGTGCAACTGGTGGAGTCTGGGGGAGGCCTA<br>GTGCAGCCTGGAAGGTCTCTGAAACTATCCTGTGT<br>AGCCTCTGGATTCACATTCAACAACCACTGGATGA<br>CCTGGATCCGCCAGGCTCCAGGGAAGGGGCTGG<br>AGTGGGTTGCATCCATTACTGATAATGGTGGTAGC<br>ACTTACTATCCAGACTCTGTGAAGGGCCGATTCAC<br>TATCTCCAGAGATAATGCAAAAAGCACCCTATACC<br>TGCACATGAACAGTCTGAGGTCTGAGGACACGGC<br>CACTTATTACTGTACAAGAGATCGGTATGACTCTG<br>ATGGTTATTATTACGTGAGGTACTATGTTGTGGAC |

TABLE 1-continued

Antibody Sequences

| Description | SEQ ID NO | Type | Sequence |
|---|---|---|---|
| | | | GCCTGGGGTCAAGGAGCTTCAGTCACTGTCTCCTCA |
| 21F12-CDR-L1 | 99 | DNA | CTAGCAAGTGAGGACATTTACAGTGATTTAGCA |
| 21F12-CDR-L2 | 100 | DNA | AATGCAAATAGTCTACAAAAT |
| 21F12-CDR-L3 | 101 | DNA | CAACAATATAGCAATTATCGTCGGACG |
| 21F12-CDR-H1 | 102 | DNA | AACCACTGGATGACC |
| 21F12-CDR-H2 | 103 | DNA | TCCATTACTGATAATGGTGGTAGCACTTACTATCCAGACTCTGTGAAGGGC |
| 21F12-CDR-H3 | 104 | DNA | GATCGGTATGACTCTGATGGTTATTATTACGTGAGGTACTATGTTGTGGACGCC |
| 21F12-VL | 105 | PRT | DVRMTQSPASLSASLGETVNIECLASEDIYSDLAWYQQKPGKSPQLLIYNANSLQNGVPSRFSGSGSGTQYSLKISTLQSEDVATYFCQQYSNYRRTFGGGTKLEIN |
| 21F12-VH | 106 | PRT | EVQLVESGGGLVQPGRSLKLSCVASGFTFNNHWMTWIRQAPGKGLEWVASITDNGGSTYYPDSVKGRFTISRDNAKSTLYLHMNSLRSEDTATYYCTRDRYDSDGYYYVRYYVVDAWGQGASVTVSS |
| 21F12-CDR-L1 | 107 | PRT | LASEDIYSDLA |
| 21F12-CDR-L2 | 108 | PRT | NANSLQN |
| 21F12-CDR-L3 | 109 | PRT | QQYSNYRRT |
| 21F12-CDR-H1 | 110 | PRT | NHWMT |
| 21F12-CDR-H2 | 111 | PRT | SITDNGGSTYYPDSVKG |
| 21F12-CDR-H3 | 112 | PRT | DRYDSDGYYYVRYYVVDA |
| 34F8-VL | 113 | DNA | GATGTTGTGTTGACACAGACTCCAGGTTCCCTGTCTGTCACACTTGGACAGCAAGTTTCTATATCCTGTAGGTCTAGTCAGAGCCTGGAAAGTCGTGATGGGAACACTTATTTGGAATGGTACCTACAGAAGCCAGGCCAGTCTCCACAGGTCCTCCTCTATGGAGTTTCCAACCGATTGTCTGGGGTCCCAGACAGGTTCCTTGGCAGAGGGTCAGGGGCAGATTTCACCCTCAAGATCAGCAGAGTAGAGCCTGAGGACTTGGGAGTTTATTACTGCTTCCAAGCTACACATGGTCCATTCACGTTCGGCTCAGGGACGAAGTTGGAAATGAAA |
| 34F8-VH | 114 | DNA | CAGGTGCAGCTGAAGGAGTCAGGACCTGGCCTGGTGCAGCCCTCACAGACCCTGTCTCTCACCTGCACTGTCTCTGGGTTCTCATTAACCACCTATCATGTGCACTGGGTTCGACAGCCTCCAGGAAAAGGTCTGGAGTGGATGGGAATAATGTGGAGAGATGGAGACACATCATATAATTCAGTTCTCAAATCTCGACTGAGCATCAGCAGGGACATCTCCAAGAGCCAAGTTTTCTTAAAAATGAGCAGTCTGCAAACTGAAGACACAGCCACTTACTTCTGTGCCAGAGGGGGGACTCTTACAACTCCCTTTACTTACTGGGGCCAAGGCACTCTGGTCACTGTCTCTTCA |
| 34F8-CDR-L1 | 115 | DNA | AGGTCTAGTCAGAGCCTGGAAAGTCGTGATGGGAACACTTATTTGGAA |
| 34F8-CDR-L2 | 116 | DNA | GGAGTTTCCAACCGATTGTCT |
| 34F8-CDR-L3 | 117 | DNA | TTCCAAGCTACACATGGTCCATTCACG |
| 34F8-CDR-H1 | 118 | DNA | ACCTATCATGTGCAC |
| 34F8-CDR-H2 | 119 | DNA | ATAATGTGGAGAGATGGAGACACATCATATAATTCAGTTCTCAAATCT |
| 34F8-CDR-H3 | 120 | DNA | GGGGGGACTCTTACAACTCCCTTTACTTAC |

TABLE 1-continued

Antibody Sequences

| Description | SEQ ID NO | Type | Sequence |
|---|---|---|---|
| 34F8-VL | 121 | PRT | DVVLTQTPGSLSVTLGQQVSISCRSSQSLESRDGNTYLEWYLQKPGQSPQVLLYGVSNRLSGVPDRFLGRGSGADFTLKISRVEPEDLGVYYCFQATHGPFTFGSGTKLEMK |
| 34F8-VH | 122 | PRT | QVQLKESGPGLVQPSQTLSLTCTVSGFSLTTYHVHWVRQPPGKGLEWMGIMWRDGDTSYNSVLKSRLSISRDISKSQVFLKMSSLQTEDTATYFCARGGTLTTPFTYWGQGTLVTVSS |
| 34F8-CDR-L1 | 123 | PRT | RSSQSLESRDGNTYLE |
| 34F8-CDR-L2 | 124 | PRT | GVSNRLS |
| 34F8-CDR-L3 | 125 | PRT | FQATHGPFT |
| 34F8-CDR-H1 | 126 | PRT | TYHVH |
| 34F8-CDR-H2 | 127 | PRT | IMWRDGDTSYNSVLKS |
| 34F8-CDR-H3 | 128 | PRT | GGTLTTPFTY |
| 38E4-VL | 129 | DNA | GATATCCGGATGACACAGTCTCCAGCTTCCCTGTCTGCATCTCTGGGAGAAACTGTCAACATCGAATGTCTAGCAAGTGAGGACATTTACAGTGATTTAGCATGGTATCAGCAGAAGCCAGGGAAATCTCCACAACTCCTGATCTATAATGCAAATAGCGTGCAAAATGGGGTCCCTTCACGGTTTAGTGGCAGTGGATCTGGCACACAGTATTCTCTAAAAATAAACAGCCTGCAATCTGAAGATGTCGCGACTTATTTCTGTCAACAGTTTAACAGTTATCCGAACACGTTTGGAGCTGGGACCAAGCTGGAAATCAAA |
| 38E4-VH | 130 | DNA | GAGGTGCAACTTCAGGAGTCAGGACCTGGCCTTGTGAAACCCTCACAGTCACTCTCCCTCACCTGTTCTGTCTCTGGTTTCTCCATCACTAATAATTACTGGGGCTGGATCCGGAAGTTCCCAAGAAATAAAATGGAGTGGATTGGACACATAAGCTACAGTGGTAGCACTAACTACAACCCATCTCTCAAAAGTCGCATCTCCATTACTAGAGACTCATCGAAGAGTCAGTTCTTCCTGCAGTTGAACTCTTTAACTACTGAGGACACAGCCACATATTACTGTGCAAGAGGATCTTATTACTATAGCGCATCGGGCTACTTTGATTATTGGGGCCAAGGAATCACGGTCACAGTCTCCTCA |
| 38E4-CDR-L1 | 131 | DNA | CTAGCAAGTGAGGACATTTACAGTGATTTAGCA |
| 38E4-CDR-L2 | 132 | DNA | AATGCAAATAGCGTGCAAAAT |
| 38E4-CDR-L3 | 133 | DNA | CAACAGTTTAACAGTTATCCGAACACG |
| 38E4-CDR-H1 | 134 | DNA | AATAATTACTGGGGC |
| 38E4-CDR-H2 | 135 | DNA | CACATAAGCTACAGTGGTAGCACTAACTACAACCCATCTCTCAAAAGT |
| 38E4-CDR-H3 | 136 | DNA | GGATCTTATTACTATAGCGCATCGGGCTACTTTGATTAT |
| 38E4-VL | 137 | PRT | DIRMTQSPASLSASLGETVNIECLASEDIYSDLAWYQQKPGKSPQLLIYNANSVQNGVPSRFSGSGSGTQYSLKINSLQSEDVATYFCQQFNSYPNTFGAGTKLEIK |
| 38E4-VH | 138 | PRT | EVQLQESGPGLVKPSQSLSLTCSVSGFSITNNYWGWIRKFPRNKMEWIGHISYSGSTNYNPSLKSRISITRDSSKSQFFLQLNSLTTEDTATYYCARGSYYYSASGYFDYWGQGITVTVSS |
| 38E4-CDR-L1 | 139 | PRT | LASEDIYSDLA |
| 38E4-CDR-L2 | 140 | PRT | NANSVQN |
| 38E4-CDR-L3 | 141 | PRT | QQFNSYPNT |
| 38E4-CDR-H1 | 142 | PRT | NNYWG |

TABLE 1-continued

Antibody Sequences

| Description | SEQ ID NO | Type | Sequence |
|---|---|---|---|
| 38E4-CDR-H2 | 143 | PRT | HISYSGSTNYNPSLKS |
| 38E4-CDR-H3 | 144 | PRT | GSYYYSASGYFDY |
| 42A5-VL | 145 | DNA | GACGTGGTCTTGACCCAAACCCCTGGATCACTTAG CGTGACACTGGGCGATCCAGCATCAATGTCCTGC AGAAGCTCCCAGTCCTTGGAGAGTAGCGACGGCA ACACATACCTCGAGTGGTATCTGCAGAAATCCGG GCAGTCCCCACAGCTGCTGATCTACGGCGTGAGT AACAGGTTCAGCGGGGTGCCTGATAGGTTCGCCG GCAGCGGGTCCGGGACAGATTTTACTCTCAAGATT AGCCGCGTCGAACCCGAGGACCTGGGCGTGTACT ACTGTTTTCAGGCCACTCGGGACCCCTTTACTTTC GGGAGCGGGACAAAGCTGGAGATTAAT |
| 42A5-VH | 146 | DNA | CAGGTCCAGCTTAAAGAGTCCGGACCTGGACTTG TGCAGCCATCCCAGACCTTGTCCTTGACCTGCACC GTGTCAGGGTTCTCTCTCACCAGTTACCACCTGCA TTGGATCAGGCAGCCTCCCGGCAAGGGGCTGGAA TGGATGGGGCTGATGTGGAGAGATGGGGATACAT CTTACAACAGCAGGCTGAAGAGCCGGCTGAGCAT TACACGGGACACCAGCAAGTCCCAGGTGTTCCTC AAGATGAGCGGGCTCCAAACTGAGGACACAGCTA CATACTACTGTGCACGCGGCATGACACTCGCCAC TCCCTTTCTGTATTGGGGCCAGGGCACTCTGGTCA CTGTGTCCTCA |
| 42A5-CDR-L1 | 147 | DNA | AGAAGCTCCCAGTCCTTGGAGAGTAGCGACGGCA ACACATACCTCGAG |
| 42A5-CDR-L2 | 148 | DNA | GGCGTGAGTAACAGGTTCAGC |
| 42A5-CDR-L3 | 149 | DNA | TTTCAGGCCACTCGGGACCCCTTTACT |
| 42A5-CDR-H1 | 150 | DNA | AGTTACCACCTGCAT |
| 42A5-CDR-H2 | 151 | DNA | CTGATGTGGAGAGATGGGGATACATCTTACAACAG CAGGCTGAAGAGC |
| 42A5-CDR-H3 | 152 | DNA | GGCATGACACTCGCCACTCCCTTTCTGTAT |
| 42A5-VL | 153 | PRT | DVVLTQTPGSLSVTLGDPASMSCRSSQSLESSDGNT YLEWYLQKSGQSPQLLIYGVSNRFSGVPDRFAGSG SGTDFTLKISRVEPEDLGVYYCFQATRDPFTFGSGT KLEIN |
| 42A5-VH | 154 | PRT | QVQLKESGPGLVQPSQTLSLTCTVSGFSLTSYHLHW IRQPPGKGLEWMGLMWRDGDTSYNSRLKSRLSITR DTSKSQVFLKMSGLQTEDTATYYCARGMTLATPFLY WGQGTLVTVSS |
| 42A5-CDR-L1 | 155 | PRT | RSSQSLESSDGNTYLE |
| 42A5-CDR-L2 | 156 | PRT | GVSNRFS |
| 42A5-CDR-L3 | 157 | PRT | FQATRDPFT |
| 42A5-CDR-H1 | 158 | PRT | SYHLH |
| 42A5-CDR-H2 | 159 | PRT | LMWRDGDTSYNSRLKS |
| 42A5-CDR-H3 | 160 | PRT | GMTLATPFLY |
| 42F4-VL | 161 | DNA | GATATCCGGATGACACAGTCGCCAGCTTCCCTGT CTGCATCTCTGGGAGAAACTGTCAACATCGAATGT CTAGCAAGTGAGGACATTCACAGTGATTTAGCATG GTATCAGCAGAAGCCAGGGAAATCTCCTCAGCTC CTGATCTATAATGCAAATAGCTTGCAAAATGGGGT CCCTTCACGGTTCAGTGGCAGTGGATCTGGCACA CAGTATTCTCTAAAAATAACCAGCCTGCAATCTGA AGATGTCGCGACTTATTTCTGTCAACAATATACCAA CTATCCGAACACGTTTGGAGCGGGGACCAAGCTG GAAATCAAT |

TABLE 1-continued

Antibody Sequences

| Description | SEQ ID NO | Type | Sequence |
|---|---|---|---|
| 42F4-VH | 162 | DNA | GAGGTGCAGCTTCAGGAGTCAGGACCTGGCCTTG TGAAACCCTCACAGTCACTCTCCCTCACCTGTTCT GTCACTGGTTACTCCATCACTAATCATTACTGGGG CTGGATCCGGAAATTCCCAGGAAATAAAATGGAGT GGATTGGACACATAAGCAACAGTGGTGGCACTAA CTACAACCCATCACTCAAAAGTCGAATCTCCATTA CTAGAGACACATCGAAGAATCAGTTCTTCCTGCAG TTGAAGTCTGTAACTACTGAGGACACAGCCACATA TTACTGTACAAGAGGATCTTATTACTATAGCGCATC GGGCTACTTTGATTACTGGGGCCAAGGAGTCCTG GTCACAGTCTCCTCC |
| 42F4-CDR-L1 | 163 | DNA | CTAGCAAGTGAGGACATTCACAGTGATTTAGCA |
| 42F4-CDR-L2 | 164 | DNA | AATGCAAATAGCTTGCAAAAT |
| 42F4-CDR-L3 | 165 | DNA | CAACAATATACCAACTATCCGAACACG |
| 42F4-CDR-H1 | 166 | DNA | AATCATTACTGGGC |
| 42F4-CDR-H2 | 167 | DNA | CACATAAGCAACAGTGGTGGCACTAACTACAACCC ATCACTCAAAAGT |
| 42F4-CDR-H3 | 168 | DNA | GGATCTTATTACTATAGCGCATCGGGCTACTTTGA TTAC |
| 42F4-VL | 169 | PRT | DIRMTQSPASLSASLGETVNIECLASEDIHSDLAWYQ QKPGKSPQLLIYNANSLQNGVPSRFSGSGSGTQYSL KITSLQSEDVATYFCQQYTNYPNTFGAGTKLEIN |
| 42F4-VH | 170 | PRT | EVQLQESGPGLVKPSQSLSLTCSVTGYSITNHYWG WIRKFPGNKMEWIGHISNSGGTNYNPSLKSRISITRD TSKNQFFLQLKSVTTEDTATYYCTRGSYYYSASGYF DYWGQGVLVTVSS |
| 42F4-CDR-L1 | 171 | PRT | LASEDIHSDLA |
| 42F4-CDR-L2 | 172 | PRT | NANSLQN |
| 42F4-CDR-L3 | 173 | PRT | QQYTNYPNT |
| 42F4-CDR-H1 | 174 | PRT | NHYWG |
| 42F4-CDR-H2 | 175 | PRT | HISNSGGTNYNPSLKS |
| 42F4-CDR-H3 | 176 | PRT | GSYYYSASGYFDY |
| 45H1-VL | 177 | DNA | GATATCCGGATGACACAGTCTCCAGCTTCCCTGTC TGCATCTCTGGGAGAAACTGTCAACATCGGATGTC TAGCAAGTGAGGACATTTACAGTGATTTAGCATGG TATCAGCAGAAGCCAGGGAAGTCTCCTCAGCTCC TGATCTATAATGCAAATAACTTGCAAAATGGGGTC CCTTCACGGTTTAGTGGCAGTGGATCTGGCACAC AATATTCTCTAAAAATAAACAGCCTGCAATCTGAAG ATGTCGCGACTTATTTCTGTCAACAATATAACAGTT ATCCGAACACGTTTGGAGCTGGGACCAAGCTGGA AATAAAA |
| 45H1-VH | 178 | DNA | GAGGTGCAGCTTCAGGAGTCAGGACCTGGCCTTG TGAAACCCTCACAGTCACTCTCCCTCATTTGTTCT GTCACTGGTTACTCCATCACTACAACTTACTGGGG CTGGATCCGGAAGTTCCCAGGAAATAAAATGGAGT GGATTGGACACATAAGTAACAGTGGTAGTACTAAT TACAACCCATCTCTCAAAAGTCGAATCTCCGTTAC TAGAGACACATCGACGAATCAGTTCTTCCTGCAGT TGAACTCTGTAACTACTGAGGACACAGCCACATAT TACTGTGCAAGAGGATCTTATTACTATAGCGCGTC GGGCTACTTTGATTACTGGGGCCACGGAGTCATG GTCACAGTCTCCTCA |
| 45H1-CDR-L1 | 179 | DNA | CTAGCAAGTGAGGACATTTACAGTGATTTAGCA |
| 45H1-CDR-L2 | 180 | DNA | AATGCAAATAACTTGCAAAAT |
| 45H1-CDR-L3 | 181 | DNA | CAACAATATAACAGTTATCCGAACACG |

TABLE 1-continued

Antibody Sequences

| Description | SEQ ID NO | Type | Sequence |
|---|---|---|---|
| 45H1-CDR-H1 | 182 | DNA | ACAACTTACTGGGGC |
| 45H1-CDR-H2 | 183 | DNA | CACATAAGTAACAGTGGTAGTACTAATTACAACCC ATCTCTCAAAAGT |
| 45H1-CDR-H3 | 184 | DNA | GGATCTTATTACTATAGCGCGTCGGGCTACTTTGA TTAC |
| 45H1-VL | 185 | PRT | DIRMTQSPASLSASLGETVNIGCLASEDIYSDLAWYQ QKPGKSPQLLIYNANNLQNGVPSRFSGSGSGTQYSL KINSLQSEDVATYFCQQYNSYPNTFGAGTKLEIK |
| 45H1-VH | 186 | PRT | EVQLQESGPGLVKPSQSLSLICSVTGYSITTTYWGWI RKFPGNKMEWIGHISNSGSTNYNPSLKSRISVTRDT STNQFFLQLNSVTTEDTATYYCARGSYYYSASGYFD YWGHGVMVTVSS |
| 45H1-CDR-L1 | 187 | PRT | LASEDIYSDLA |
| 45H1-CDR-L2 | 188 | PRT | NANNLQN |
| 45H1-CDR-L3 | 189 | PRT | QQYNSYPNT |
| 45H1-CDR-H1 | 190 | PRT | TTYWG |
| 45H1-CDR-H2 | 191 | PRT | HISNSGSTNYNPSLKS |
| 45H1-CDR-H3 | 192 | PRT | GSYYYSASGYFDY |
| 14E11-VL (control) | 193 | PRT | DIVMTQSHKFMSTSVGDRVSITCKASQDVSTAVAWY QQKPGQSPKLLIYLTSYRNTGVPDRFTGSGSGTDFT FTISSVQAEDLAVYYCQQHYKTPYSFGGGTKLERLR |
| 14E11-VH (control) | 194 | PRT | QVQLEESGPGLVAPSQSLSITCTVSGFSLTGYGIYW VRQPPGKGLEWLGMIWGDGRTDYNSALKSRLSISK DNSKSQVFLKMNSLQTDDTARYYCARDYYGSKDYW GQGTTLTVS |
| 1A6-VL (control) | 195 | PRT | DIVLTQSPASLAVSLGQRATISCKASQSVDYDGDSYL NWYQQKPGQPPKLLIYAASNLESGIPARFSGSGSGT DFTLNIHPVEEEDAATYYCQQSNGDPWTFGGGTKLE IK |
| 1A6-VH (control) | 196 | PRT | QVTLKESGPGILKPSQTLSLTCSFSGFSLSTSGMGV GWIRQPSGKGLEWLAHIWWDDDKYYNPSLKSQLTIS KDTSRNQVFLKITSVDAADTATYYCARKRSSVVAHY YAMDYWGQGTSVTVS |

Provided in certain embodiments herein are humanized anti-FXI and/or anti-FXIa antibodies. Various techniques are known in the art for humanizing antibodies from non-human species such that the antibodies are modified to increase their similarity to antibodies naturally occurring in humans. Six CDRs are present in each antigen binding domain of a natural antibody. These CDRs are short, non-contiguous sequences of amino acids that are specifically positioned to form the antigen binding domain as the antibody assumes its three dimensional configuration. The remainder of the amino acids in the antigen binding domains, referred to as "framework" regions, show less inter-molecular variability and form a scaffold to allow correct positioning of the CDRs. In some embodiments, the antibodies or fragments disclosed herein have conserved sequences for CDR3 regions.

For example, humanization of the antibodies disclosed herein can be accomplished by CDR grafting of monoclonal antibodies produced by immunizing mice or rats. The CDRs of a mouse monoclonal antibody can be grafted into a human framework, which is subsequently joined to a human constant region to obtain a humanized antibody. Briefly, the human germline antibody sequence database, the protein data bank (PDB), the INN (International Nonproprietary Names) database, and other suitable databases can be searched and the most similar frameworks to the antibodies can be identified by the search. In addition, some back mutations to the donor residues are made in the human acceptor frameworks. In some embodiments, the variable regions are linked to a human IgG constant region. For example, human IgG1, IgG2, IgG3 and IgG4 Fc domains can be used. It is within the purview of one of ordinary skill in the art to humanize a monoclonal antibody produced by a non-human species based on the existing technology.

The sequences of the variable regions of several example humanized antibodies are shown in Table 2 below.

TABLE 2

Sequences of humanized antibodies

| Description | SEQ ID NO | Type | Sequence (with mutations highlighted in bold and underlined, and CDRs highlighted in italic) |
|---|---|---|---|
| h-19F6-VL | 197 | PRT | QFQLTQPSSVSASVGDRVTITC*E RSSGDIGDSYVSW*YQQKPGQPPK NVIYIY*ADDQRPS*GVPDRFSGSIDG SGNSASLTISSLQAEDAADYFC*Q SYDSNIDFNPV*FGGGTKLEVK |
| h-19F6-VH | 198 | PRT | EVQLVESGGGLVQPGRSLRLSCT ASGFTFS*KYAMSW*VRQAPGKGLE WV*SA*INYDGSTTYY*A*DS*VK*GRFT LSRDNSKNTLYLQMNSLRAEDTA VYYCAR*HPFNNFGIW*FAYWGCIG TLVTVS |
| h-34F8-VL | 199 | PRT | DVVLTQTPLSLPVTPGEPASISC RSSQSLES*R*DGNTYLEWYLQKPG QSPQVLLY*GV*SNRLSGVPDRFSG SGSGTDFTLKISRVEAEDVGVYY C*FQ*ATHGPFTFGQGTKLEIKRT |
| h-34F8-VH | 200 | PRT | QVQLQESGPGLVKPSETLSLTCT VSG*F*SLTTYHVHWVRQPPGKGLE WIG*IMW*RDGDTYYNSSLKSRVTI SRDTSKNQVSLKLSSVTAADTAV YFC*ARGGTLTTPFTY*WGQGTLVT VSS |
| h-42A5-VL | 201 | PRT | DVVLTQTPLSLSVTPGQPASISC RSSQSLESSDGNTYLEWYLQKPG QSPQLLIY*GV*SNRFSGVPDRFSG SGSGTDFTLKISRVEAEDLGVYY C*FQ*ATRDPFTFGQGTKLEIKRT |
| h-42A5-VH | 202 | PRT | QVTLKESGPVLVKPTETLTLTCT VSGFSLT*SYHLHW*IRQPPGKALE W*MG*L*MW*RDGDTSYNSRLKS*RL*TI SRDTSKSQVVLTMTNMDPVDTAT YYCAR*GMTLATPFLY*WGQGTLVT VS |

The antibodies provided herein include variants of the sequences disclosed herein that contain one or more mutations in their amino acid sequences while retaining binding affinity for FXI, FXIa, and/or a fragment thereof (e.g., a fragment comprising the A3 domain). In some embodiments, the antibodies include a variable region having an amino acid sequence that is at least 85%, at least 90%, at least 95%, at least 98%, or at least 99% identical to a sequence selected from the group consisting of SEQ ID NOs: 9, 10, 25, 26, 41, 42, 57, 58, 73, 74, 89, 90, 105, 106, 121, 122, 137, 138, 153, 154, 169, 170, 185, 186, and 197-209, or a fragment thereof that retains binding affinity for FXI, FXIa, and/or a fragment thereof.

Also included in this disclosure are variants of nucleic acids encoding antibodies that bind to FXI, FXIa, and/or a fragment thereof (e.g., a fragment comprising the A3 domain). In some embodiments, the nucleic acids encoding the antibodies include a variable region having a nucleic acid sequence that is at least 85%, at least 90%, at least 95%, at least 98%, or at least 99% identical to a sequence selected from the group consisting of SEQ ID NOs: 1, 2, 17, 18, 33, 34, 49, 50, 65, 66, 81, 82, 97, 98, 113, 114, 129, 130, 145, 146, 161, 162, 177, and 178, or a fragment thereof that encodes a polypeptide with binding affinity for FXI, FXIa, and/or a fragment thereof.

In some embodiments, the antibodies are further subjected to a strategic Chemistry, Manufacturing, and Control (CMC) development such that the novel antibodies such as monoclonal antibodies or humanized monoclonal antibodies disclosed herein are advanced from discovery to human clinical trials, and then to the pharmaceutical market. The modifications further improve the properties of the antibodies without compromising the immunological functions of the antibodies. In certain embodiments, a CMC modified antibody is more stable under various temperatures (e.g., 4° C., 25° C., and 37° C.) for an extended period of time (e.g., 3 days, 7 days, 14 days and 28 days) and under repeated freeze/thaw cycles (e.g., −40° C./25° C. for up to 5 cycles) comparing to the unmodified antibody. Additionally, the CMC modified antibodies have an acceptable solubility. For example, for a given sequence of a light chain or a heavy chain, certain amino acids can be potential oxidation and glycosylation sites. These amino acid residues at the potential oxidation, deamidation, or glycosylation sites may be mutated and additional residues in the proximity can also be mutated and/or optimized to maintain the 3D structure and function of a particular antibody. In some embodiments, one or more amino acid residues in a CDR region having the potential of oxidation, deamidation, or glycosylation are mutated to improve the stability of the antibody or a fragment thereof without compromising the immunological functions. In some embodiments, one or more Met residues in a CDR region having the potential of oxidation are mutated. In some embodiments, one or more Asn residues in a CDR region having the potential of deamidation are mutated.

The sequences of the variable regions of several example CMC optimized, humanized antibodies are shown in Table 3 below.

TABLE 3

Sequences of CMC optimized, humanized antibodies

| Description | SEQ ID NO | Type | Sequence (with mutations highlighted in bold and underlined, and with CDRs highlighted in italic) |
|---|---|---|---|
| h-42A5-VL | 204 | PRT | DIVMTQTPLSLSVTPGQPASISC RSSQSLESSDGNTYLEWYLQKPG QSPQLLIY*GV*SNRFSGVPDRFSG SGSGTDFTLKISRVEAEDVGVYY C*FQ*ATRDPFTFGQGTKLEIKRT |
| h-42A5-VH | 205 | PRT | QVTLKESGPVLVKPTETLTLTCT VSGFSLSSYSVAWIRQPPGKALE WLAEIWRDGDTSYNSRLKSRLTI SKDTSKSQVVLTMTNMDPVDTAT YYCAR*GMTLATPFLY*WGQGTLVT VSS |
| h-34F8-VL | 206 | PRT | DVVLTQTPLSLPVTPGEPASISC RSSQSLESRDGNTYLEWYLQKPG QSPQVLLYGVSNRLSGVPDRFSG SGSGTDFTLKISRVEAEDVGVYY C*FQ*ATHGPFTFGQGTKLEIKRT |
| h-34F8-VH | 207 | PRT | QVQLQESGPGLVKPSETLSLTCT VSGYSISTYHVHWVRQPPGKGLE WIG*IMW*RDGDTYYNPKLKSRVTI SVDTSKNQVSLKLSSVTAADTAV YFCAR*GGTLTTPF*TYWGQGTLVT VSS |
| h-19F6-VL | 208 | PRT | QFQLTQPSSVSASVGDRVTITC*E RSSGDIGDSYVSW*YQQKPGQPPK NVIYIY*ADDQRPSG*VPDRFSGSIDG SGNSASLTISSLQAEDAADYFC*Q SYDSNIDFNPV*FGGGTKLTVL |

TABLE 3-continued

Sequences of CMC optimized, humanized antibodies

| Description | SEQ ID NO | Type | Sequence (with mutations highlighted in bold and underlined, and with CDRs highlighted in italic) |
|---|---|---|---|
| h-19F6-VH | 209 | PRT | EVQLVESGGGLVQPGRSLRLSCT ASGFTFS*KYAMS*WVRQAPGKGLE WV*SAINYDGSTTYYADSVK*GRFT LSRDNSKNTLYLQMNSLRAEDTA VYYCAR*HPFNNFGIWFAYW*GQGT LVTVS |

Pharmaceutical Compositions

The antibodies disclosed herein can be formulated into pharmaceutical compositions. The pharmaceutical compositions may further comprise one or more pharmaceutically acceptable carriers, excipients, preservatives, or a combination thereof. The pharmaceutical compositions can have various formulations, e.g., injectable formulations, lyophilized formulations, liquid formulations, etc. Depending on the formulation and administration route, one would select suitable additives, such as adjuvants, carriers, excipients, preservatives.[34]

The pharmaceutical composition can be included in a kit with an instruction for using the composition.

Methods of Treatment

Provided herein is a method of treating and/or preventing thrombosis in a subject suffering from thrombosis and/or at an elevated risk of developing thrombosis. Also provided is a method of inhibiting the formation of blood clots in a subject. These methods entail administering a therapeutically effective amount of an anti-FXI and/or FXIa antibody provided herein to intervene in the intrinsic pathway. In some embodiments, these methods comprise administering a pharmaceutical composition comprising an anti-FXI and/or anti-FXIa antibody as provided herein to the subject.

The methods disclosed herein can be used to prevent and/or treat complications or conditions associated with thrombosis in a subject in need thereof. Thrombosis causes or is associated with a number of complications or conditions, such as embolic stroke, venous thrombosis such as venous thromboembolism (VTE), deep vein thrombosis (DVT), and pulmonary embolism (PE), arterial thrombosis such as acute coronary syndrome (ACS), coronary artery disease (CAD), and peripheral artery disease (PAD). Other conditions associated with thrombosis include, for example, high risk of VTE in surgical patients, immobilized patients, patients with cancer, patients with heart failure, pregnant patients, or patients having other medical conditions that may cause thrombosis. The methods disclosed herein relate to a preventive anticoagulant therapy, that is, thromboprophylaxis. These methods entail administering to a subject suffering from a thrombosis-related complication disclosed above a therapeutically effective amount of an anti-FXI and/or FXIa antibody as disclosed herein or a therapeutically effective amount of a pharmaceutical composition comprising the anti-FXI and/or FXIa antibody. The antibody or pharmaceutical composition can be administered either alone or in combination with any other therapy for treating or preventing the thrombosis-related complications or conditions.

Also provided is a method of treating and/or preventing sepsis in a subject in need thereof. It was attempted to administer anticoagulants to sepsis patients to improve mortality or morbidity. However, the attempt was unsuccessful due to the undesired bleeding caused by anticoagulants. The antibodies disclosed herein can be used as a secondary therapy in combination with other therapeutic agents for treating sepsis, such as antibiotics.

As used herein, the term "subject" refers to mammalian subject, preferably a human. A "subject in need thereof" refers to a subject who has been diagnosed with thrombosis or complications or conditions associated with thrombosis, or is at an elevated risk of developing thrombosis or complications or conditions associated with thrombosis. The phrases "subject" and "patient" are used interchangeably herein.

The terms "treat," "treating," and "treatment" as used herein with regard to a condition refers to alleviating the condition partially or entirely, preventing the condition, decreasing the likelihood of occurrence or recurrence of the condition, slowing the progression or development of the condition, or eliminating, reducing, or slowing the development of one or more symptoms associated with the condition. With regard to thrombosis and/or complications or conditions associated with thrombosis, "treating" may refer to preventing or slowing the existing blood clot from growing larger, and/or preventing or slowing the formation of blood clot. In some embodiments, the term "treat," "treating," or "treatment" means that the subject has a reduced number or size of blood clots comparing to a subject without being administered with the antibodies or functional fragments thereof. In some embodiments, the term "treat," "treating," or "treatment" means that one or more symptoms of thrombosis and/or thrombosis-related conditions or complications are alleviated in a subject receiving an antibody or pharmaceutical composition as disclosed herein comparing to a subject who does not receive such treatment.

A "therapeutically effective amount" of an antibody or pharmaceutical composition as used herein is an amount of the antibody or pharmaceutical composition that produces a desired therapeutic effect in a subject, such as treating and/or preventing thrombosis. In certain embodiments, the therapeutically effective amount is an amount of the antibody or pharmaceutical composition that yields maximum therapeutic effect. In other embodiments, the therapeutically effective amount yields a therapeutic effect that is less than the maximum therapeutic effect. For example, a therapeutically effective amount may be an amount that produces a therapeutic effect while avoiding one or more side effects associated with a dosage that yields maximum therapeutic effect. A therapeutically effective amount for a particular composition will vary based on a variety of factors, including but not limited to the characteristics of the therapeutic composition (e.g., activity, pharmacokinetics, pharmacodynamics, and bioavailability), the physiological condition of the subject (e.g., age, body weight, sex, disease type and stage, medical history, general physical condition, responsiveness to a given dosage, and other present medications), the nature of any pharmaceutically acceptable carriers, excipients, and preservatives in the composition, and the route of administration. One skilled in the clinical and pharmacological arts will be able to determine a therapeutically effective amount through routine experimentation, namely by monitoring a subject's response to administration of the antibody or the pharmaceutical composition and adjusting the dosage accordingly. For additional guidance, see, e.g., Remington: The Science and Practice of Pharmacy, 22$^{nd}$ Edition, Pharmaceutical Press, London, 2012, and Goodman & Gilman's The Pharmacological Basis of Therapeutics, 12$^{th}$ Edition, McGraw-Hill, New York, N.Y., 2011, the entire disclosures of which are incorporated by reference herein.

In some embodiments, a therapeutically effective amount of an antibody disclosed herein is in the range from about 0.01 mg/kg to about 30 mg/kg, from about 0.1 mg/kg to about 10 mg/kg, from about 1 mg/kg to about 5 mg/kg.

It is within the purview of one of ordinary skill in the art to select a suitable administration route, such as subcutaneous administration, intravenous administration, intramuscular administration, intradermal administration, intrathecal administration, or intraperitoneal administration. For treating a subject in need thereof, the antibody or pharmaceutical composition can be administered continuously or intermittently, for an immediate release, controlled release or sustained release. Additionally, the antibody or pharmaceutical composition can be administered three times a day, twice a day, or once a day for a period of 3 days, 5 days, 7 days, 10 days, 2 weeks, 3 weeks, or 4 weeks. The antibody or pharmaceutical composition may be administered over a pre-determined time period. Alternatively, the antibody or pharmaceutical composition may be administered until a particular therapeutic benchmark is reached. In certain embodiments, the methods provided herein include a step of evaluating one or more therapeutic benchmarks to determine whether to continue administration of the antibody or pharmaceutical composition.

Method of Producing Antibodies

Also provided herein are methods of producing the anti-FXI and/or anti-FXIa antibodies disclosed herein. In certain embodiments, these methods entail the steps of cloning a nucleic acid encoding an anti-FXI and/or anti-FXIa antibody into a vector, transforming a host cell with the vector, and culturing the host cell to express the antibody. The expressed antibody can be purified from the host cell using any known technique. Various expression vectors such as pTT5 vector, and pcDNA3 vector, as well as various host cell lines such as CHO cells (e.g. CHO-K1 and ExpiCHO), and HEK193T cells, can be used.

Also encompassed by this disclosure are antibodies produced by the method disclosed above. The antibodies may have been subjected to one or more post-translational modifications.

The following examples are provided to better illustrate the embodiments and are not to be interpreted as limiting the scope of any claimed embodiment. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Materials and Methods

Materials.

Human FXI (Cat No. HFXI 1111), FXIa (Cat No. HFXIa 1111a), FXIIa (HFXIIa 1212a), and FIX (Cat No. HFIX 1009) were purchased from Enzyme Research Laboratory (IN, USA).

Antibody Preparation.

Animal immunization and hybridoma screening were performed at Genscript Inc. (Nanjing, China), and the procedures that were applied to animals in this protocol were approved by the Genscript Institutional Animal Care and Use Committee. The experiment was performed in accordance with the approved guidelines. Wistar rats were immunized with human FXI, and splenocytes from animals with a good immune response were collected for the preparation of hybridomas, which were subjected to subcloning by limiting dilution. Finally, several monoclonal hybridoma clones expressing the desired anti-FXI antibodies, including 19F6, h-34F8 and 42A5, were obtained by using ELISA and functional screening. After determining the amino acid sequences of their variable regions, 19F6, h-34F8 and 42A5 were subjected to humanization, resulting in three humanized antibodies, h-19F6, h-34F8 and h-42A5, in an IgG4 form. These three humanized antibodies were produced in a transient mammalian expression system and purified by Protein G chromatography.

Activated Partial Thromboplastin Time (APTT) and Prothrombin Time (PT).

Standard human plasma purchased from Symens Inc. was mixed with equal volume of various antibodies at various concentrations from 0 to 400 nM for 5 minutes before being tested on a CA600 analyzer. In the APTT assay, 50 µL of the plasma-antibody mixture and 25 µL of APTT reagent (SMN 10445709, Symens Inc.) were mixed at 37° C. for 4 min. Then 25 µL of CaCl$_2$) Solution (25 mM, SMN 10446232, Symens Inc.) was added and time to clot formation was determined. In the PT assay, 50 µL of the plasma-antibody mixture was mixed with an equal volume of PT reagent (SMN 10446442, Symens Inc.) at 37° C. and time to clot formation was determined.

The effects of the antibodies on APTT and PT in monkey plasma were also evaluated using the same methods applied to human plasma. In these assays, monkey plasma diluted with an equal volume of phosphate-buffered saline (PBS) was used instead of the above mentioned human plasma-antibody mixture.

FXI Activation by FXIIa.

Human FXI (500 nM) was pre-incubated at room temperature with 1 µM control IgG4 or h-19F6 or h-34F8 or h-42A5 in PBS for 5 minutes. At time zero, FXIIa, HK, and kaolin were added so that the final concentrations were FXI (250 nM), FXIIa (50 nM), HK(100 nM), and kaolin (0.5 mg/mL). At 0, 30, 60, 120 min intervals, 50-µL samples were collected into dodecyl sulfate sample buffer. Samples were size-fractionated on 10% non-reducing gels and transferred to polyvinylidene fluoride membranes. Western blotting was performed to determine the FXI as well as FXIa-light chain levels using a mouse anti-human FXI IgG (105, an in-house made antibody binding the C-terminal of FXI). The image results were acquired using a ChemiDocMP Imaging System with Image Lab Software (Bio-Rad).

FXIa-Mediated FIX Activation.

Human FIX (200 nM) was incubated with FXIa (5 nM) in PBS containing 5 mM CaCl$_2$) at room temperature in the presence of 1 µM control IgG4, h-19F6, h-34F8, or h-42A5. At intervals of 0, 15, 30, 45, and 60 min, 50-µL samples were collected into dodecyl sulfate sample buffer. Samples were size-fractionated on 10% non-reducing gels and transferred to polyvinylidene fluoride membranes. Western blotting was performed to determine the FIX as well as FIXa levels using goat anti-human FIX IgG (Affinity Biologicals). The image results were acquired using a ChemiDocMP Imaging System with Image Lab Software (Bio-Rad).

Surface Plasmon Resonance (SPR).

The interaction of the antibodies with FXI was determined by the SPR assay on a Biacore T200 system (Biacore, GE Healthcare). Briefly, human IgG capture antibody (Biacore, GE Healthcare) was pre-immobilized on a CM5 sensor chip (GE Healthcare), and test antibodies were captured by flowing through the chip. The final amount of the test antibodies captured was adjusted to an equal amount of 15 response units (RU) by adjusting the capture time. Then, antigen FXI was allowed to flow through the chip for 180 s for association and then for 1200 s for dissociation. FXI was tested at concentrations of 0.063, 0.313, 0.625, 1.25, 3.125 and 6.25 nM. The data were collected and the affinities between the test antibodies and FXI were analyzed using the Biacore Evaluation Software.

To determine the binding sites of test antibodies on FXI, four mutants of FXI tagged with 6×His at the C terminal were first generated by replacing each apple domain (A1, A2, A3, and A4) with the corresponding domains from human prekallikrein. Equal amounts of each mutant were immobilized on a CM5 sensor chip, and test antibodies (33.3 nM) were allowed to flow through the chip for 180 s for association and then for 1200 s for dissociation. The amounts of each antibody captured were recorded in response units (RU) using the Biacore Evaluation Software.

Epitope binding results of the test antibodies were also analyzed using the Biacore T200 system. Briefly, wild-type FXI with 6×His tag was pre-immobilized on a CM5 sensor chip (GE Healthcare), and h-19F6, h-34F8, or h-42A5 (5 µg/ml) was successively injected into flow cells on the sensor surface at a flow rate of 30 µl/minute to monitor the change in response.

Pharmacodynamics in Cynomolgus Monkeys.

This animal experiment and the following AV thrombosis experiment were performed at Wincon Inc. (Nanning, China), and the procedures applied to animals in this protocol were approved by the Wincon Institutional Animal Care and Use Committee. The experiments were performed in accordance with the approved guidelines. Animals received an intravenous bolus injection of different doses of h-19F6, h-34 F8, or h-42A5. Two mL of blood from the superficial veins of upper limb was collected into a collection tube containing 3.2% sodium citrate at pre-dose (time 0) and at 0.5 h, 1 h, 3 h, 6 h, 12 h, and 24 h post-dose. Then, tubes were mixed by gentle inversion ten times at room temperature. Plasma was collected in labelled tubes and stored at −20° C. until clotting time analysis. Plasma samples were diluted with an equal volume of phosphate buffered saline (pH 7.4) and then subjected to APTT and PT analysis on an automatic analyser (CA660, Sysmex Inc.).

AV Shunt Thrombosis and Bleeding Time Test.

A 30-min post-test antibody treatment was administered via intravenous bolus in cynomolgus monkeys. A tail vein bleeding time test was then performed, followed by thrombosis induction. Thrombosis was induced by connecting a shunt device between the femoral arterial and femoral venous cannulas containing a pre-weighed 10-cm-long thread. Blood was allowed to flow through the shunt for 10 min. The thrombus formed on the thread was weighed. Immediately after the removal of the shunt, blood samples were collected, and the next higher level of test antibody was administered. This bleeding/thrombosis process was carried out four times to dose the vehicle and three escalating levels (0.1, 0.3, 1 mg/kg) of test antibody in the same animal.

For bleeding time evaluation, a 2-mL syringe was inserted into the tail vein of the animals. When the volume of blood in the syringe stopped increasing, the elapsed time was recorded manually as the bleeding time.

Ferric Chloride ($FeCl_3$)-Induced Thrombosis and Bleeding Time Test.

This animal experiment was performed at PharmaLegacy Laboratories Inc. (Shanghai, China), and the procedures that were applied to animals in this protocol were approved by the PharmaLegacy Institutional Animal Care and Use Committee. The experiment was performed in accordance with the approved guidelines. Cynomolgus monkeys were pre-anaesthetized with 1.5 mg/kg of Zoletil, intubated, and ventilated with a respirator. Anaesthesia was maintained with isoflurane. Blood pressure, heart rate, and body temperature were monitored throughout the entire procedure. The vehicle or 0.3 mg/kg of h-19F6, h-34F8, or h-42A5 was administered through a limb vein 2 hours before $FeCl_3$ application. The left femoral artery was exposed and isolated via blunt dissection. A Doppler flow probe was set up on the artery, and blood flow was continuously recorded. Before applying $FeCl_3$, blood flow was measured for at least 5 minutes. Then, two pieces of filter paper pre-soaked with 40% $FeCl_3$ were applied to the adventitial surface of the vessel upstream of the probe for 10 minutes. After the filter paper was removed, the site of application was washed with saline. Blood flow was continuously measured until it decreased to 0. The time to 80% occlusion (blood flow reduced to 20% of the baseline blood flow) and the time to 100% occlusion (blood flow reduced to 0) were recorded. In the same animals, haemostasis was evaluated using the Surgicutt device and bleeding time was manually recorded at pre-dose and 1-hour post-dose. At the end of the study (approximately 3 hours post-dose), blood samples were collected.

The binding specificity of test antibodies to human FXI in plasma.

Test Antibodies (h-19F6, h-42A5, and 14E11) were First Biotinylated Using EZ-Link™ Sulfo-NHS-LC-Biotinylation Kit (Cat No. 21435, Thermo Fisher Inc.). These antibodies (25 µg each) were incubated with 200 µL of human standard plasma (Siemens Inc.) or FXI-deficient plasma (Hyphen Biomed Inc.) for 1 h. Then 50 µL of Streptavidin-coated beads (Dynabeads™ M-280 Streptavidin, Thermo Fisher Inc.) were added to the mixture to extract the biotin-containing antigen-antibody complex. After washing with PBS for 3 times, the antigen-antibody complex was then eluted and subjected to Western blotting using a mouse anti-human FXI IgG (1C5, an in-house made antibody binding the C-terminal of FXI) as the primary antibody. The image results were acquired using a Chemi-DocMP Imaging System with Image Lab Software (Bio-Rad). In Western blotting, 10 µL of human standard plasma and FXI-deficient plasma served as FXI-positive and FXI-negative controls, respectively.

Statistical Analysis.

Numerical data from multiple experiments are presented as means±standard error of mean (SEM). One-way ANOVA followed by Dunnett's multiple comparisons test was used for the statistical analysis of thrombus weight in the AV shunt experiment and both bleeding time tests. The Kruskal-Wallis rank test was performed for the statistical analysis of occlusion times in the $FeCl_3$-induced thrombosis experiment. A value of $P<0.05$ was considered statistically significant.

Example 2: Generation and Sequencing of Anti-FXI Antibodies

BALB/c mice and Wistar rats were immunized with human FXI, and splenocytes from the animals with good immune response were collected for the preparation of hybridomas, which were subjected to subcloning by limiting dilution. Twelve monoclonal hybridoma clones expressing desired anti-FXI antibodies 3G12, 5B2, 7C9, 7F1, 13F4, 19F6, 21F12, 34F8, 38E4, 42A5, 42F4, and 45H1 were obtained by using capture ELISA and functional screening.

To determine the amino acid and nucleotide sequences of the variable region of the light ($V_L$) and heavy chain ($V_H$) of these antibodies, cDNAs encoding $V_L$ and $V_H$ were cloned from the corresponding hybridoma cells by standard RT-PCR procedures. The $V_L$ and $V_H$ sequences of exemplary antibodies, including the sequences of CDRs, are shown in Table 1.

Example 3: Determination of Anti-Coagulation Activity in Human Plasma Using Activated Partial Thromboplastin Time (APTT) Assay and Prothrombin Time (PT) Assay APTT assay measures the activity of the intrinsic and common pathways of coagulation; whereas PT assay measures the activity of the extrinsic and common pathways of coagulation. The antibodies tested in these experiments were 19F6, 34F8, 42A5, 1A6 and 14E11. Antibodies 1A6 and 14E11 were used as positive controls in this experiment. The sequences of the variable regions of the control antibodies were obtained from U.S. Pat. No. 8,388,959 and U.S. Patent Application Publication No. 2013/0171144 and reformatted to IgG4. These antibodies were then expressed using ExpiCHO cell system. The APTT assay and PT assay were performed as described above.

As shown in FIG. 1, all antibodies tested increased APTT in a concentration-dependent manner at a relatively low concentration, for example, up to 100 nM (or up to 200 nM for 14E11); whereas none of these antibodies had a significant effect on PT (data not shown). These results indicate that all of the antibodies tested inhibited the intrinsic pathway of coagulation but not the extrinsic pathway.

Figure 2A:
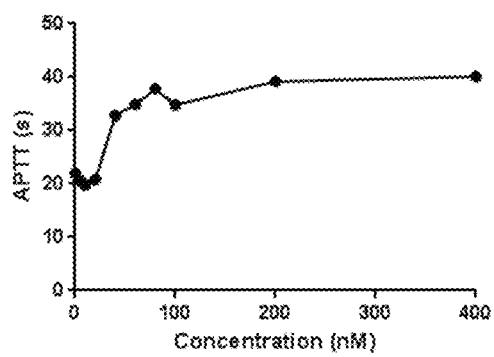
FIGS. 2A-2C illustrate the effects of antibodies 19F6 (A), 34F8 (B), and 42A5 (C) on the APTT assay in monkey plasma. The monkey plasma supplemented with three different antibodies at a concentration ranging from 0 to 400 nM were tested in an APTT assay as described in Example 4.
Figure 2B:
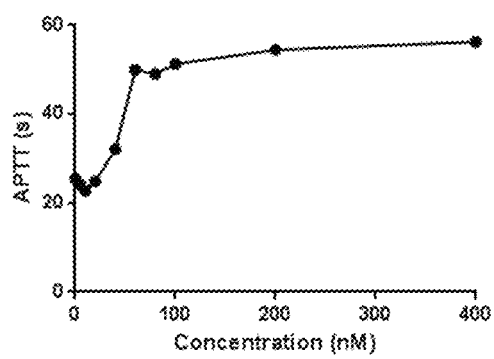
Figure 2C:
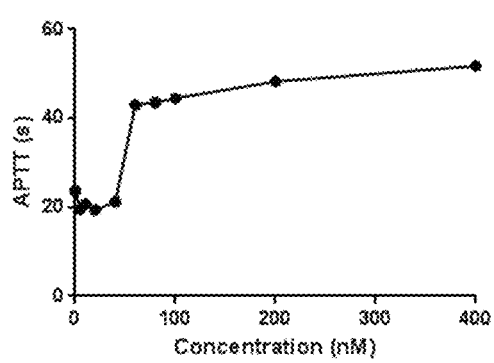
Figure 3A:
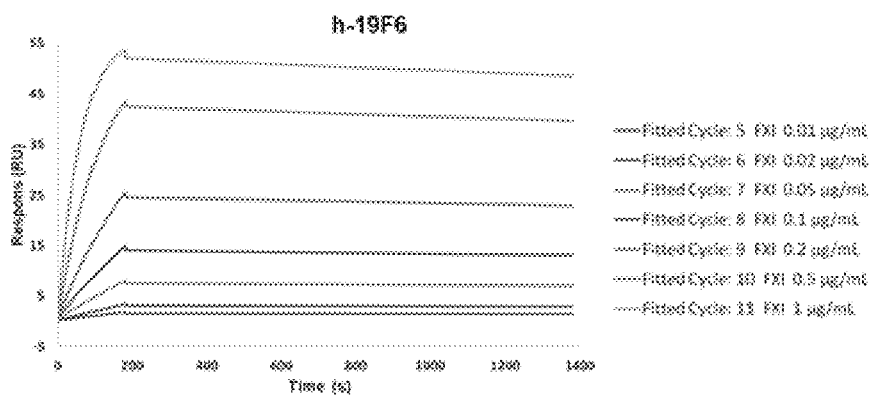
FIGS. 3A-3F illustrates SPR sensorgrams for FXI binding to immobilized h-19F6 (A), h-34F8 (B), and h-42A5 (C), as well as SPR sensorgrams for FXIa binding to immobilized h-19F6 (D), h-34F8 (E), and h-42A5 (F). Data were fit with 1:1 binding model, and curve fits at test concentrations of FXI (0.005-1 ng/mL) are shown overlaid on the sensorgrams. Each curve indicates a different test concentration of FXI or FXIa.
Figure 3B:
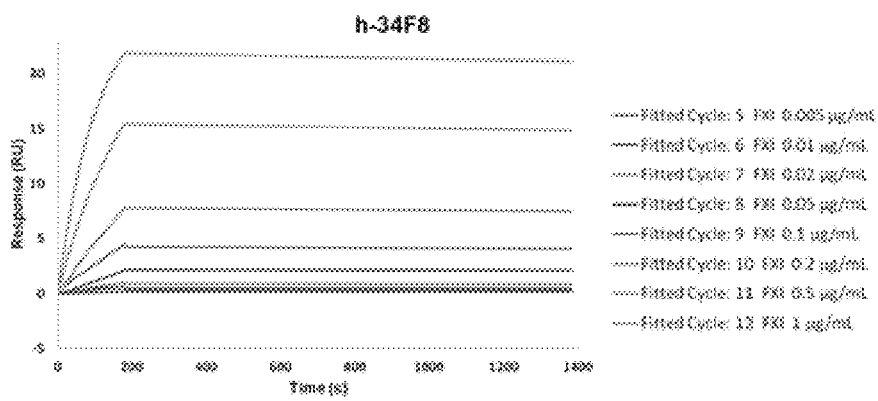
Figure 3C:
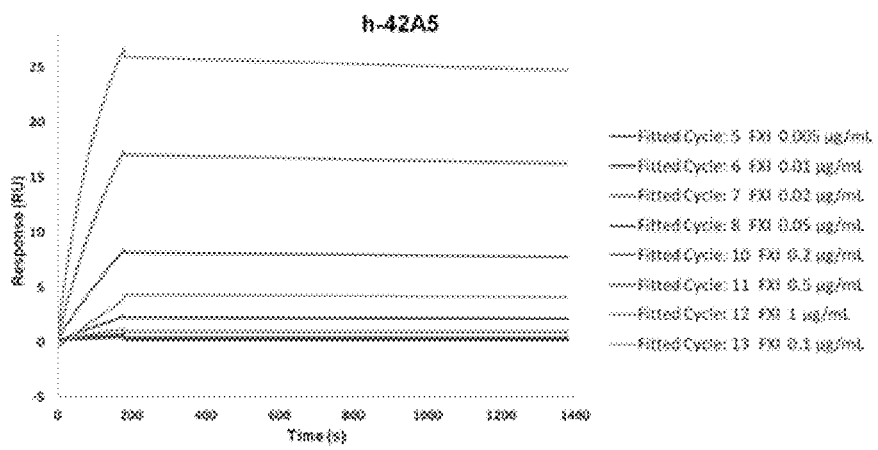
Figure 3D:
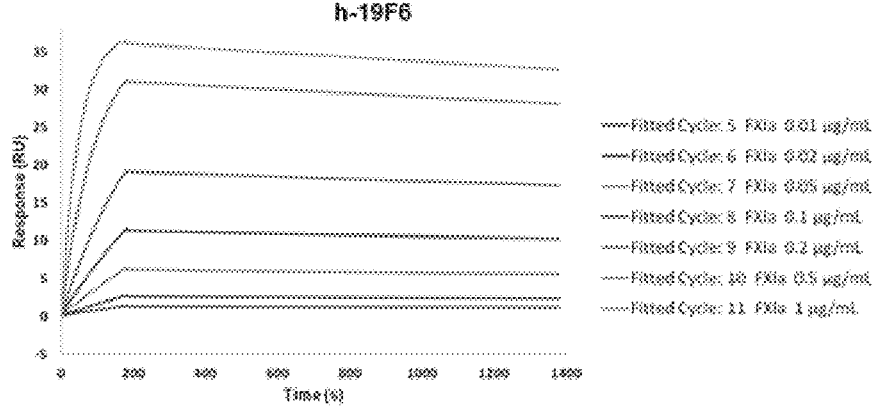
Figure 3E:
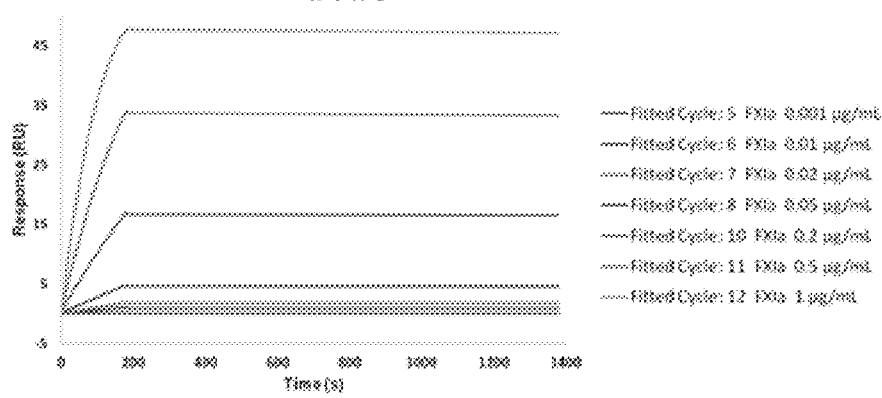
Figure 3F:
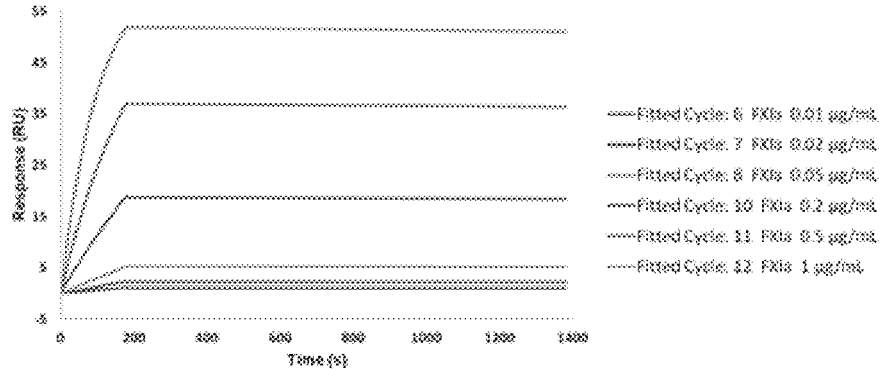

Example 4: Determination of the Anti-Coagulation Activity in the Plasma of Non-Human Species Using Activated Partial Thromboplastin Time (APTT) Assay Effects of various antibodies, including 19F6, 34F8 and 42A5, on coagulation were assessed in the mouse, rat, and monkey plasma using the same method as described in Example 3. None of the antibodies tested had any effect on APTT in the mouse and rat plasma, but all of them, at a relatively low concentration, concentration-dependently, increased APTT in the monkey plasma as shown in FIG. 2, indicating that the antibodies tested had cross-activity with monkey FXI/FXIa, but not with mouse or rat FXI/FXIa.

Example 5: Humanization of Anti-FXI Antibodies

The use of murine monoclonal antibodies directly as therapeutics has been hindered by the short half-life and the elicitation of the human anti-murine antibody responses. One solution to this problem is to humanize the murine antibodies. Some antibodies were subjected to humanization by CDR grafting. Suitable human acceptor frameworks for both $V_L$ and $V_H$ of each murine antibody were identified and varying numbers of back mutations were introduced at the selected human frameworks to maintain the structure and/or function of the resulting antibody. If the affinity and function of these humanized antibodies were not substantially inferior to the corresponding unmodified antibodies, the modified antibodies were considered successfully humanized. Three humanized $V_H$ and $V_L$ sequences of 19F6, 34F8 and 42A5, described as h-19F6, h-34F8, and h-42A5, respectively, are shown in Table 2.

Example 6: Determination of the Affinity of Anti-FXI Antibodies to Human FXI

The affinity of anti-FXI/FXIa antibodies to FXI/FXIa were determined using surface plasmon resonance (SPR) technology performed on the BIAcore T200 instrument. The humanized antibodies were constructed by linking the variable regions of the antibodies disclosed herein to human IgG4 Fc domain and the recombinants were expressed in CHO cells. These antibodies were captured onto a Biacore CM5 sensor chip that was pre-immobilized with an anti-human IgG antibody.

Then different concentrations of the purified antigen FXI or FXIa (0.005-1 μg/mL) were allowed to flow through the CM5 chip for 180 s for association with the anti-FXI/FXIa antibody, followed by a time of 1800 s for dissociation. The binding data was collected and the affinity between FXI/FXIa and the test antibodies was analyzed using the Biacore Evaluation Software provided by GE Healthcare. The SPR sensorgrams of FXI/FXIa binding to immobilized h-19F6, h-34F8, and h-42A5 are shown in FIG. 3. As shown in FIG. 3, the response (RU) for each antibody became higher with escalating concentrations of FXI or FXIa. The dissociation constants ($K_D$) of h-19F6, h-34F8, and h-42A5 to FXI and FXIa were calculated and detailed in Table 4. The affinities of each antibody to FXI and FXIa are considered to be the same since the difference between them is less than 10 times.

TABLE 4

$K_D$ values of the antibodies to FXI and FXIa

| | $K_D$ (pM) | |
|---|---|---|
| Antibody | FXI | FXIa |
| h-19F6 | 22.2 | 25.8 |
| h-34F8 | 19.5 | 3.85 |
| h-42A5 | 35.7 | 8.14 |

Example 7: Determination of the Binding Site of Anti-FXI Antibodies on FXI

The binding sites of 19F6 and 42A5 on FXI were determined using the SPR technology. Briefly, human IgG capture antibody was pre-immobilized on a Biacore CM5 sensor chip, and recombinant h-19F6 or h-42A5 was captured by flowing through the chip. An equal amount (15 relative units) of h-19F6 and h-42A5 was captured through adjustment of the antibody flowing time. Then wild type FXI or chimeric FXI in which individual apple domain was replaced with the corresponding domain from the human prekallikrein (FXI/PK chimeras) was allowed to flow through the chip for 180 seconds for association with h-19F6 or h-42A5, followed by a time period of 1800 seconds for dissociation. The binding data was analyzed in a high performance kinetic mode as only one concentration of FXI, wild-type or chimeric, was tested in the SPR assay. Results showed that both h-19F6 and h-42A5 bound FXI as well as FXI/PK chimeras except when the A3 domain of FXI was replaced with the corresponding PK domain, indicating that part or the complete epitope of h-19F6 and h-42A5 on FXI is located in the A3 domain.

Example 8: Functional Neutralization of FXIa by the Antibodies

Human FXIa activity was determined by measuring the cleavage of a specific, chromogenic substrate, S-2366 (Diapharma Inc.). For testing the inhibitory activity of the antibodies, antibodies h-19F6, h-34F8 and h-42A5 were pre-incubated for 5 minutes at room temperature with a final concentration of 5 nM of FXIa in PBS (phosphate buffer saline). Then an equal volume of 1 mM of S-2366 was added to initiate the FXIa cleavage reaction and changes in absorbance at 405 nm was monitored continuously using a M5$^e$ plate reader (Molecular Devices Inc.). Data were analyzed using the GraphPad Prism software and are shown in FIG. 4. The calculated apparent Ki for h-19F6, h-34F8, and h-42A5 are 0.67, 2.08, and 1.43 nM, respectively. Therefore, all three antibodies tested exhibited satisfying inhibitory effects on FXIa at a relatively low concentration.

Example 9: Inhibition of FXIa-Mediated FIX Activation by the Antibodies

Figure 5A:
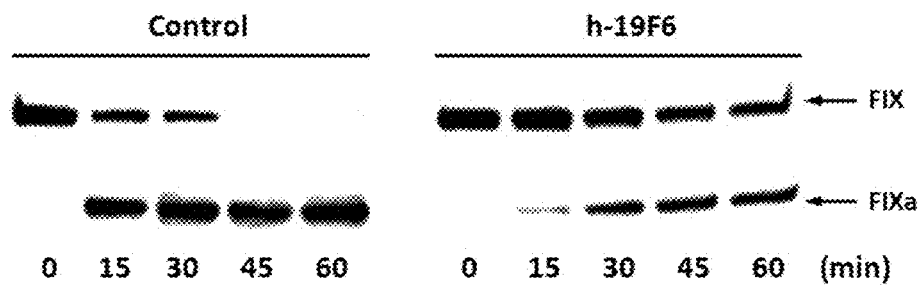
FIGS. 5A-5B illustrate the inhibitory effects of antibodies h-19F6 (A) and h-42A5 (B) on FXIa-mediated activation of FIX to FIXa. Human FIX (200 nM) was incubated with FXIa (5 nM) in PBS with 5 mM $CaCl_2$) at room temperature with 1 µM h-19F6 or h-42A5. At the indicated intervals, samples were collected and the FIX as well as FIXa was determined by Western blots using goat anti-human FIX IgG (Affinity Biologicals).
Figure 5B:
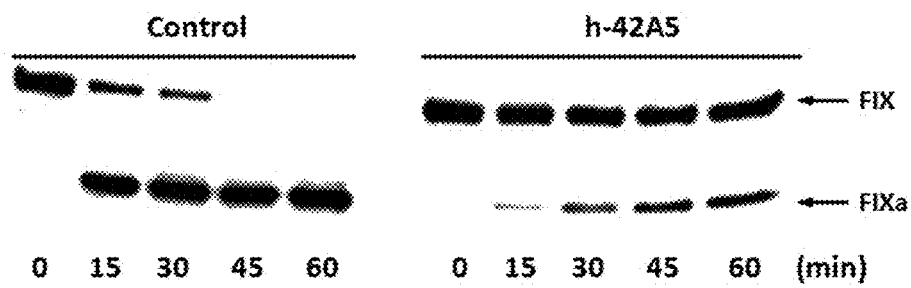
Figure 5C:
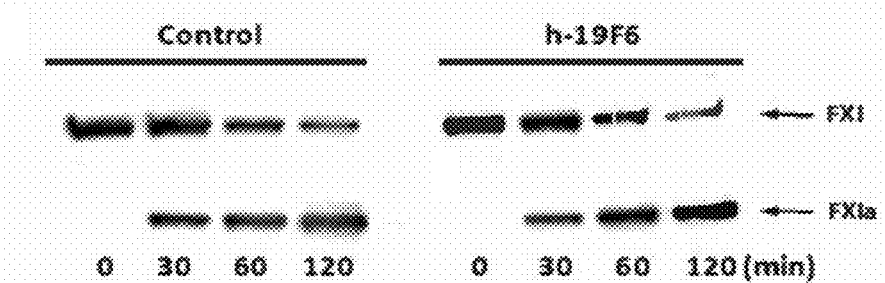
FIGS. 5C-5D illustrate the inhibitory effects of antibodies h-19F6 (C) and h-42A5 (D) on FXIIa-mediated activation of FXI to FXIa. Human FXI (500 nM) was incubated with FXIIa (50 nM) in the presence of 1 µM of h-19F6 or h-42A5. FXI, as well as FXIa light chain, which represents FXIa production, at indicated time points was determined by Western blots. A human IgG4 (1 µM) was used as the control.
Figure 5D:
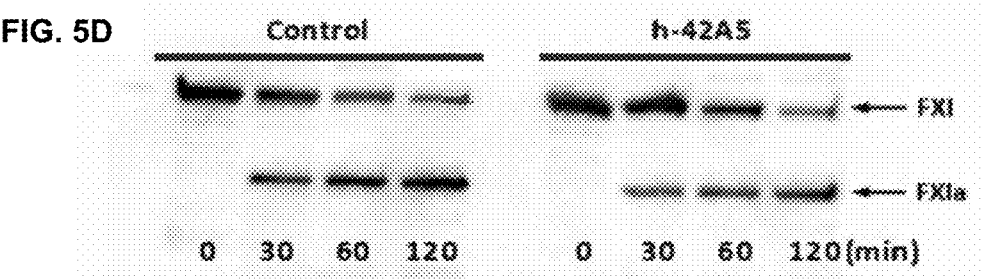

The FXIa-mediated FIX activation was performed as described above. Anti-FXI antibodies may modulate the intrinsic pathway by inhibiting FXI activation and/or by inhibiting FXIa activity. First the effects of the two antibodies h-19F6 and h-42A5 on FXIIa-mediated activation of FXI were tested and it was found that neither h-19F6 nor h-42A5 prevented the conversion of FXI to FXIa mediated by FXIIa (FIGS. 5C and 5D). Then, the effect of these two antibodies on FXIa activity was tested using FIX as the substrate. As shown in FIGS. 5A and 5B, both h-19F6 and h-42A5 reduced FIX activation in a concentration-dependent manner. The inhibitory effect of these two antibodies on FXIa activity was further confirmed by using a chromogenic substrate of FXIa, S-2366. Both antibodies concentration-dependently inhibited the hydrolysis of S-2366 (FIG. 4).

Figure 6A:
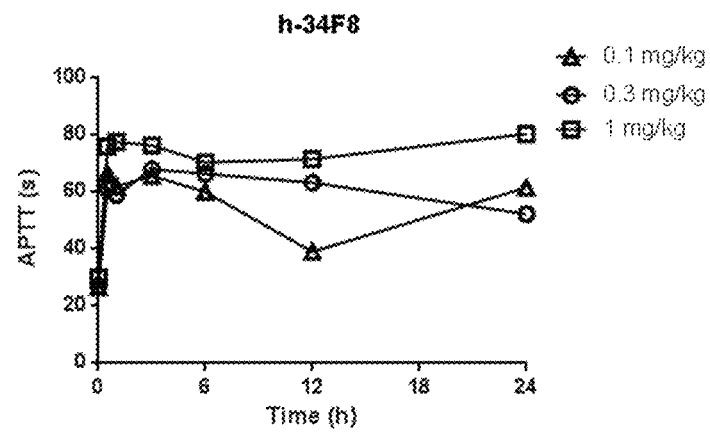
FIGS. 6A-6C illustrate the effects of antibodies h-34F8, h-19F6, and h-42A5 on APTT in cynomolgus monkeys. The monkeys were intravenously administered with indicated doses of h-34F8 (A), h-19F6 (B), and h-42A5 (C). Ex vivo clotting time APTT was determined at pre-dose (time 0), and 0.5, 1, 3, 6, 12, and 24 hours post-dose.

Example 10: Evaluation of the Effects of Anti-FXI Antibodies on Clotting Time in Cynomolgus Monkeys To find proper animal species for in vivo experiments, the cross-reactivity of the antibodies for mouse, rat, and monkey FXI was tested by the APTT assay. The antibodies prolonged APTT in monkey plasma but not in mouse or rat plasma (data not shown). Thus, monkey models were chosen for evaluating the pharmacodynamic effects of the three antibodies on clotting times prior to efficacy studies on thrombosis in vivo. Cynomolgus monkeys were intravenously administered with indicated doses of various antibodies. Blood from the superficial veins of the upper limb was collected at pre-dose and at 0.5, 1, 3, 6, 12, and 24 hours post-dose, and citrated plasma was prepared for APTT and PT determination. In the APTT test, 50 µL of diluted plasma sample and 25 µL of APTT reagent (SMN 10445709, Symens Inc.) were mixed and incubated at 37° C. for 4 min. Then 25 µL of CaCl$_2$) Solution (25 mM, SMN 10446232, Symens Inc.) was added and time to clot formation was determined. In the PT test, 50 µL of diluted plasma sample was mixed with equal volume of PT reagent (SMN 10446442, Symens Inc.) and incubated at 37° C. and time to clot formation was determined. All three antibodies tested demonstrated dose-dependently increased APTT as shown in FIG. 6 and none of them affected PT as shown in FIG. 7.

Figure 6B:
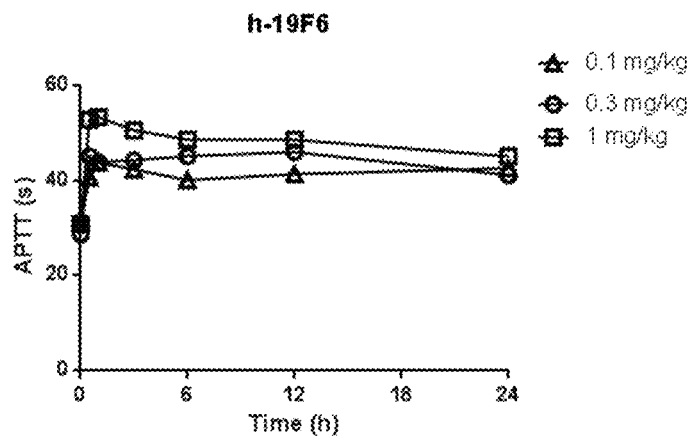
Figure 6C:
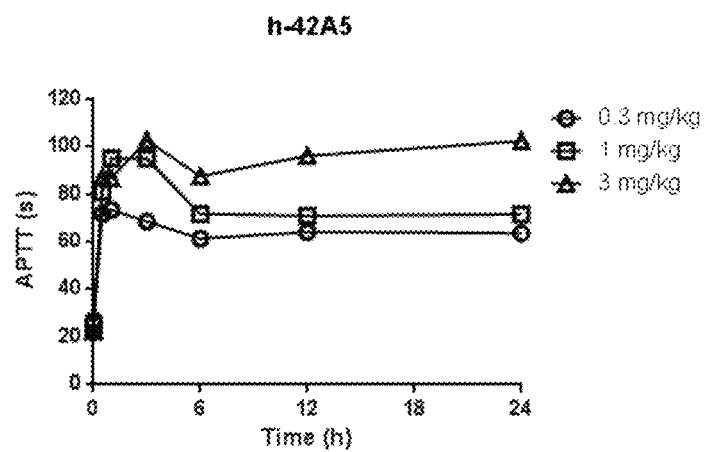
Figure 7A:
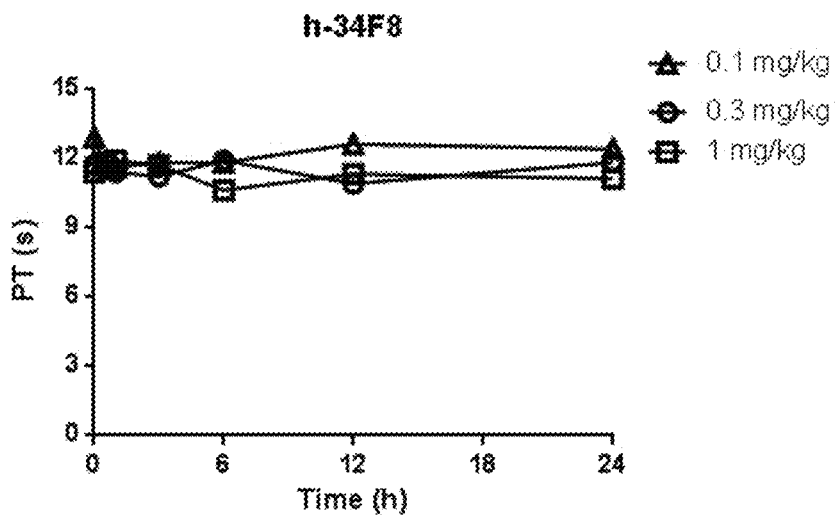
FIGS. 7A-7C illustrate the effects of antibodies h-34F8, h-19F6, and h-42A5 on PT in cynomolgus monkeys. Monkeys were intravenously administered with the indicated doses of h-34F8 (A), h-19F6 (B), and h-42A5 (C). Ex vivo clotting time PT was determined at pre-dose (time 0), and 0.5, 1, 3, 6, 12, and 24 hours post-dose.
Figure 7B:
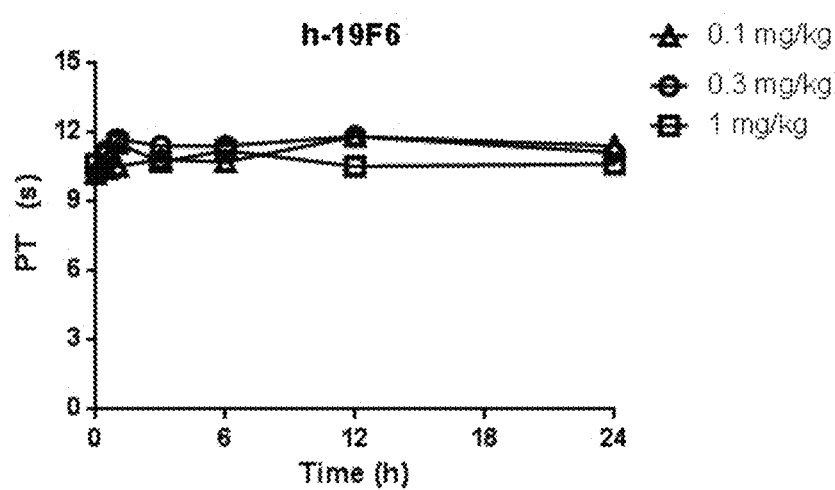
Figure 7C:
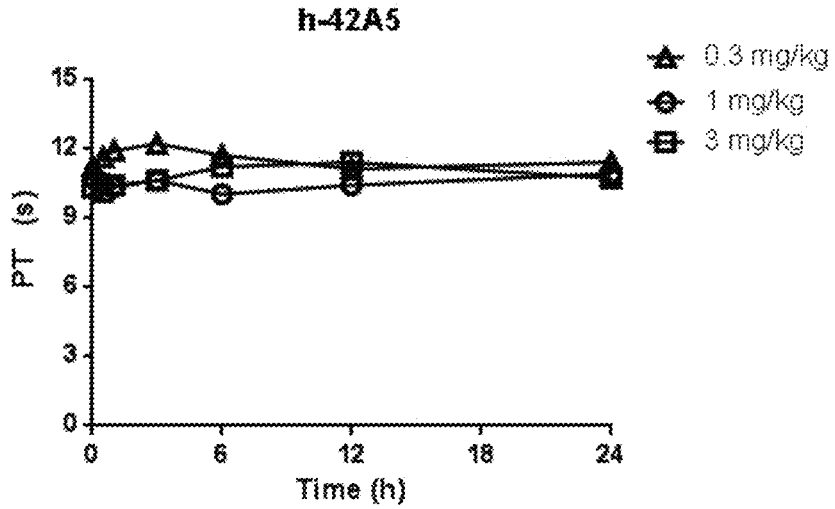
Figure 16A:
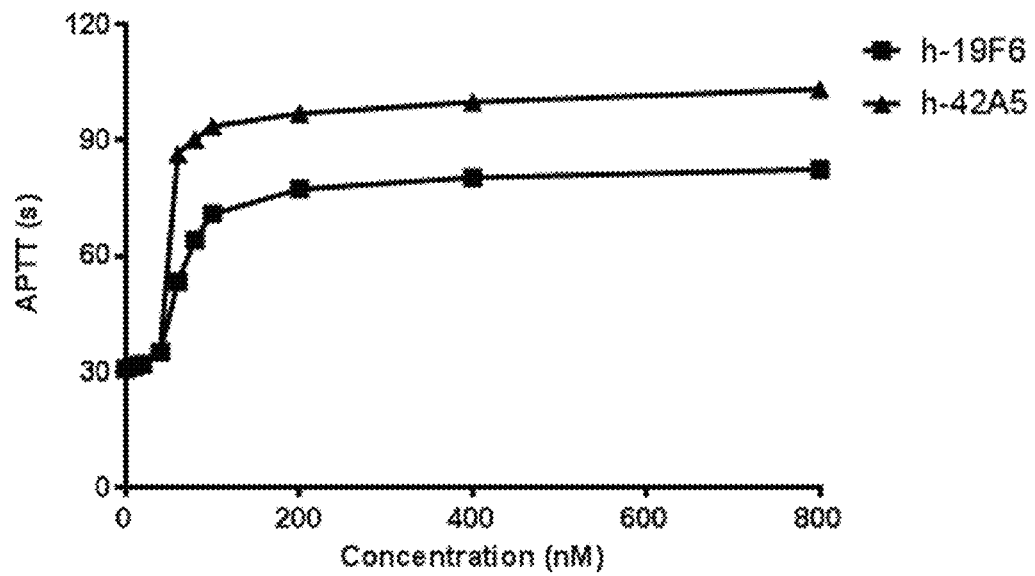
FIGS. 16A-16B illustrate the effects of h-19F6 and h-42A5 on APTT and PT in human plasma.

Both h-19F6 and h-42A5 dose-dependently prolonged APTT (FIGS. 6B and 6C). Notably, h-42A5 increased APTT more strongly than h-19F6 did at the same dose levels (0.3 and 1 mg/kg), consistent with the antibodies' in vitro effects on human APTT (FIG. 16A). In addition, neither antibody affected the PT in vivo (FIGS. 7B and 7C).

Example 11: Evaluation of the Effects of Anti-FXI Antibodies in Arteriovenous (AV) Shunt Thrombosis and Tail Vein Bleeding Models in Cynomolgus Monkeys Both thrombosis and bleeding time were assessed in the same animal for multiple doses of each antibody tested. The antibodies included in this experiment were h-34F8, h-19F6, and h42A5. Briefly, bleeding time and thrombosis were sequentially evaluated at pre-dose and 30 minutes following each administration of the antibody. The bleeding/thrombosis assessments were conducted four times: pre-dose and post-dose at three escalating dose levels (0.1, 0.3 and 1 mg/kg).

For AV shunt thrombosis, a shunt device containing a pre-weighed 10-cm long silk thread was applied to connecting the femoral arterial and femoral venous cannulae, and blood was allowed to flow through the shunt for 10 minutes. Then the thread was removed from the shunt and weighed again. Clot weight on the thread was calculated as the difference of the thread weight before and after blood flow.

For bleeding time evaluation, a 2-mL syringe was inserted into the tail vein of the animals. When the volume of blood in the syringe stopped increasing, the elapsed time was recorded manually as the bleeding time.

Figure 8A:
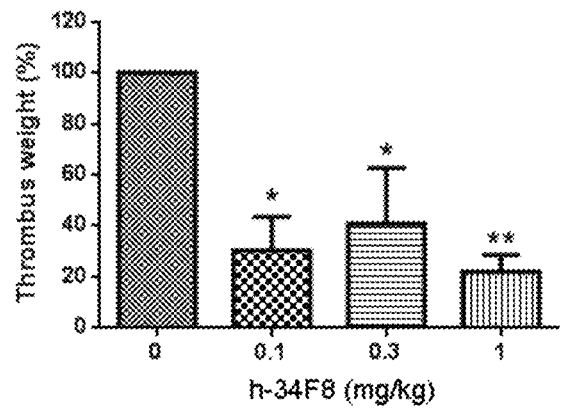
FIGS. 8A-8C illustrate the effects of antibodies h-34F8, h-19F6, and h-42A5 on AV shunt thrombosis in cynomolgus monkeys. Escalating levels of h-34F8 (A), h-19F6 (B), or h-42A5 (C) were intravenously administered to monkeys (n=3 for h-34F8 and h-19F6; n=4 for h-42A5), changes of clot weight from pre-dose were determined in monkey model of AV shunt thrombosis. *$P<0.05$, $P<0.01$ and *$P<0.001$ vs. Vehicle.
Figure 8B:
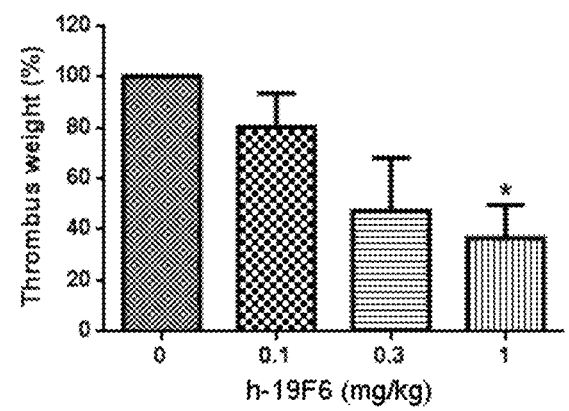
Figure 8C:
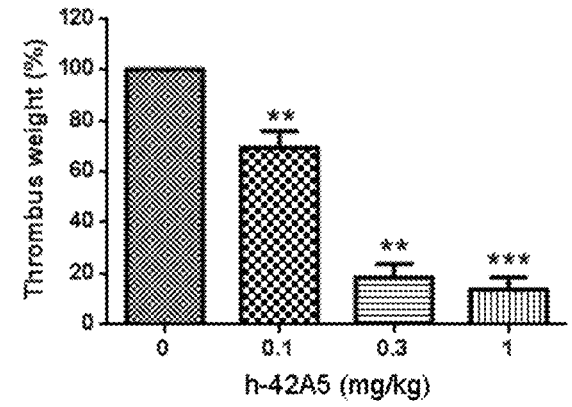
Figure 9A:
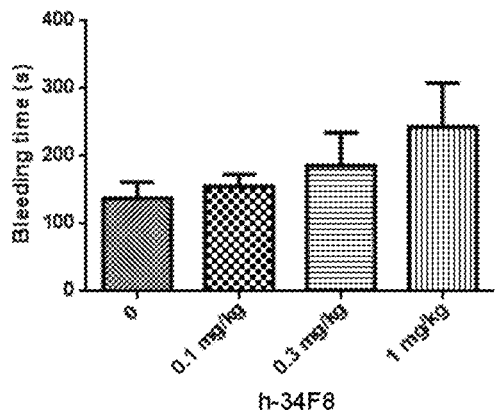
FIGS. 9A-9C illustrate the effects of antibodies h-34F8, h-19F6, and h-42A5 on bleeding time in cynomolgus monkeys. Escalating levels of h-34F8 (A), h-19F6 (B), or h-42A5 (C) were intravenously administered to monkeys (n=3 for 34F8 and h-19F6; n=4 for h-42A5), bleeding time was assessed at pre-dose and at 30 min post each dose.
Figure 9B:
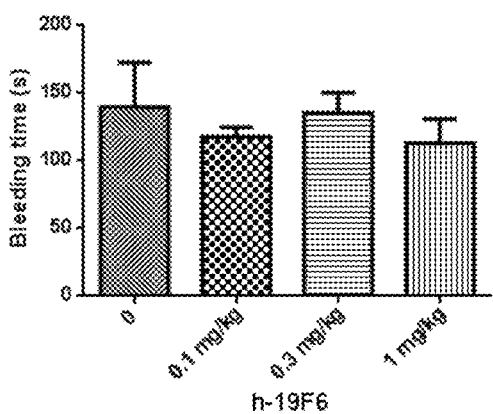
Figure 9C:
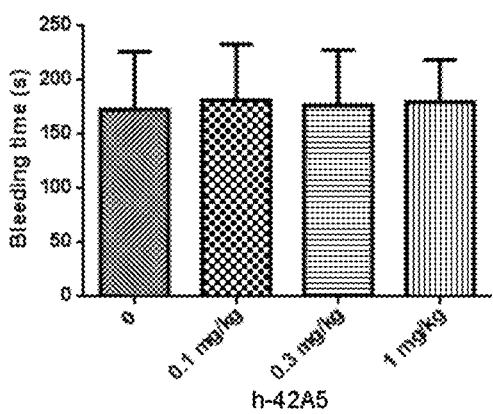

All antibodies dose-dependently reduced the thrombus weight as shown in FIG. 8 and none of them prolonged the tail vein bleeding time as shown in FIG. 9. Effects of h-19F6 and h-42A5 on thrombosis and haemostasis were evaluated in monkey models of AV shunt thrombosis and tail vein bleeding. Intravenous injection of h-19F6 resulted in a dose-dependent reduction of clot weight, and a significant reduction was observed at 1 mg/kg dose (FIG. 8B). Regarding h-42A5-treated animals, clot weight was significantly reduced at all test dose levels in a dose-dependent manner (FIG. 8C). No significant change in bleeding time was noted following treatment with h-19F6 or h-42A5 (FIGS. 9B and 9C).

Example 12: Evaluation of the Effects of Anti-FXI Antibodies on Ferric Chloride-Induced Artery Thrombosis and Template Bleeding Time in Cynomolgus Monkeys Cynomolgus monkeys were pre-anesthetized with 1.5 mg/kg of Zoletil, intubated, and ventilated with a respirator. Anesthesia was maintained with isoflurane. The blood pressure, heart rate, and body temperature were monitored throughout the entire procedure. The antibodies tested, including h-34F8, h-19F6, and h-42A5, or the vehicle control were administered through limb vein by injection 2 hours before FeCl$_3$ application. The left femoral artery was exposed and isolated via blunt dissection. A Doppler flow probe was set up on the artery and the blood flow was continuously recorded. Before applying FeCl$_3$, the blood flow was measured for at least 5 minutes. Then two pieces of filter paper pre-soaked with FeCl$_3$ were applied to the adventitial surface of the vessel upstream from the probe for 10 minutes. After the filter paper was removed, the site of application was washed with saline. Blood flow was continuously measured until it decreased to 0. The time to 80% occlusion (blood flow reduced to 20% of the baseline blood flow) and the time to 100% occlusion (blood flow reduced to 0) were recorded. In the same animal, template bleeding time was assessed at pre-dose and 1 hour post-dose.

Figure 10A:
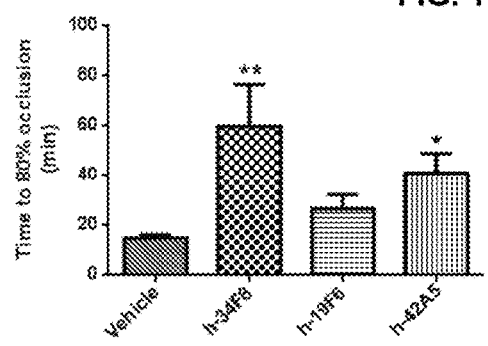
FIGS. 10A-10B illustrate the antithrombotic effects of antibodies h-34F8, h-19F6, and h-42A5. Four groups of monkeys (n=5) were intravenously administered with the vehicle, 0.3 mg/kg of h-34F8, h-19F6, or h-42A5, for 2 hours, and $FeCl_3$ was applied on the left femoral artery of each animal to induce thrombosis. The time to 80% thrombotic occlusion (A) and to 100% thrombotic occlusion (B) were determined by monitoring the blood flow velocity. *$P<0.05$ and **$P<0.01$ vs. vehicle.
Figure 10B:
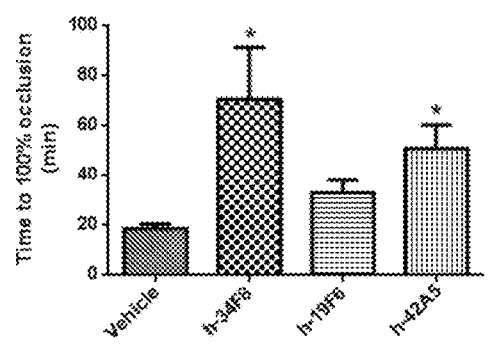

The effects of all three antibodies on $FeCl_3$-induced arterial thrombosis were investigated. Four groups of monkeys were treated with the vehicle control, h-34F8, h-19F6, or h-42A5 for 2 hours, respectively, and $FeCl_3$ was applied on the left femoral artery of each animal to induce thrombosis. Downstream blood flow velocity was monitored. The time to 80% and to 100% thrombotic occlusion in the vehicle control group was 14.66±1.30 min and 18.50±1.76 min, respectively. Pretreatment with 0.3 mg/kg of h-34F8 or h-42A5 significantly delayed the time to 80% occlusion to 59.53±16.95 min and 40.80±7.94 min, and the time to 100% occlusion to 70.40±20.76 min and 50.61±9.48 min, respectively, as shown in FIG. 10. Prolongation of the time to 80% occlusion (26.43±5.72 min) and to 100% occlusion (32.78±5.09 min) was also observed in monkeys treated with h-19F6, although there was no statistically significant difference when compared to the vehicle control group as shown in FIG. 10.

Figure 11A:
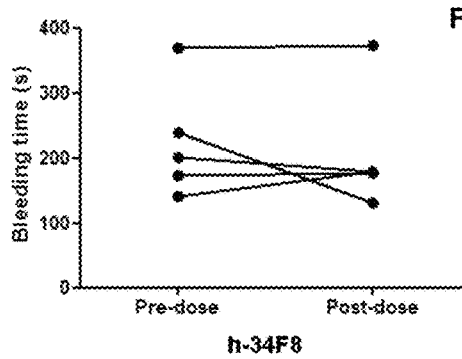
FIGS. 11A-11D illustrate that the treatment with antibodies h-34F8, h-19F6, or h-42A5 did not prolong the bleeding time in monkeys. Four groups of monkeys (n=5) were intravenously administered with the vehicle, 0.3 mg/kg of h-34F8, h-19F6, or h-42A5, and template bleeding time was measured pre-dose and 1 hour post-dose. The individual bleeding time in h-34F8, h-19F6, and h-42A5 treated group is shown in (A), (B) and (C), respectively. The bleed time change upon vehicle, h-34F8, h-19F6, or h-42A5 treatment is shown in (D).
Figure 11B:
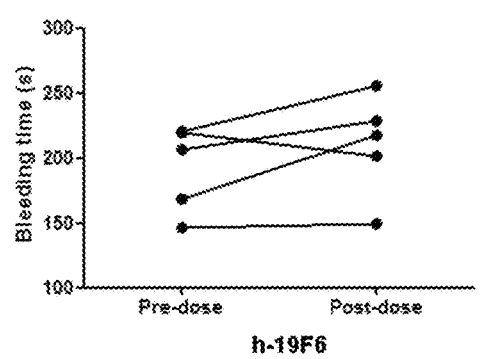
Figure 11C:
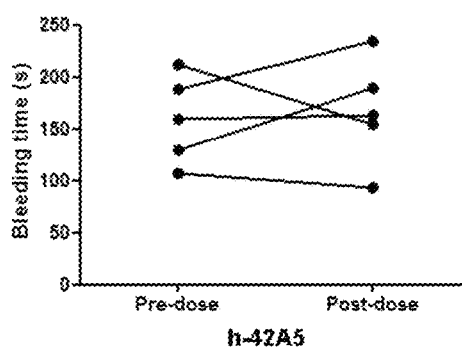
Figure 11D:
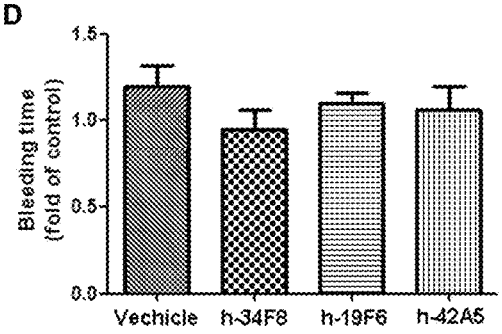

The effects of the antibodies on haemostasis was assessed in terms of template bleeding time. No significant difference was noted between pre-dose and 1 hour post-dose for each test article (FIGS. 11A, 11B, and 11C). The bleeding time change following h-34F8, h-19F6, and h-42A5 treatment was not different from that following the vehicle control treatment (FIG. 11D).

Figure 18:
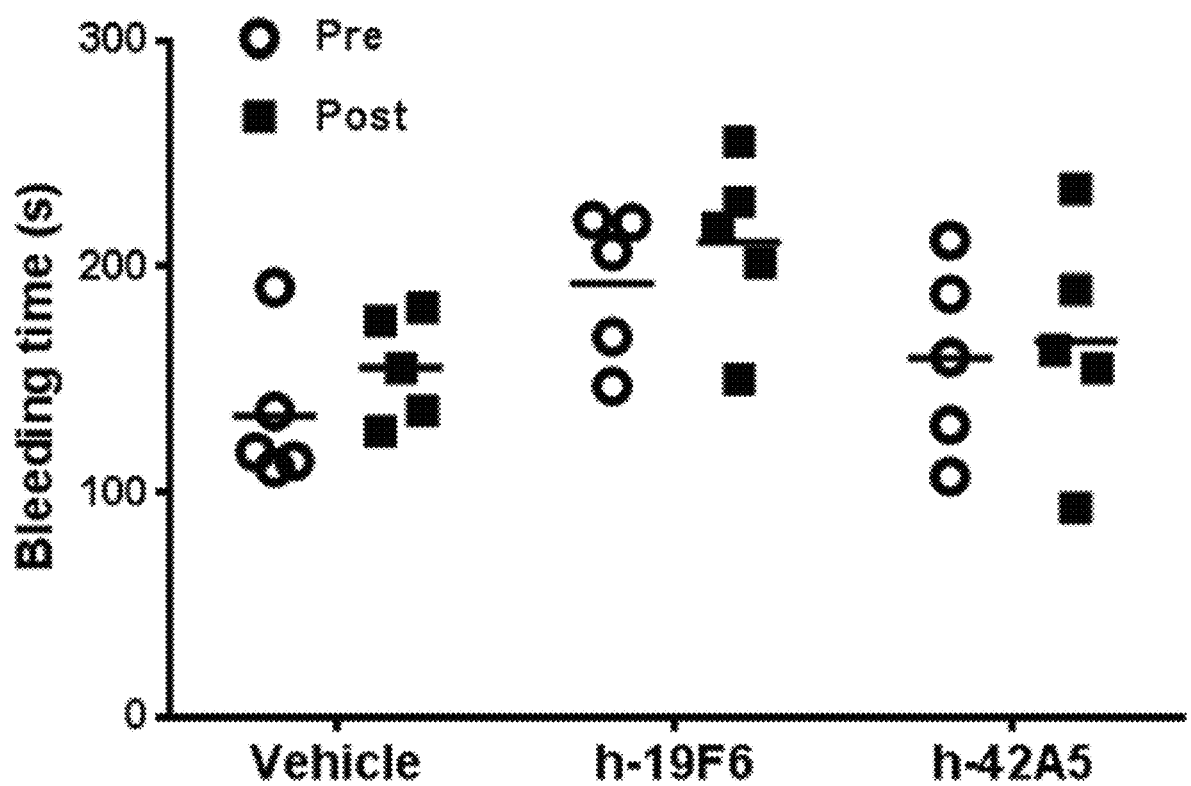
FIG. 18 shows the effects of h-19F6 and h-42A5 in AV shunt thrombosis models on bleeding times recorded at pre-dose and 1-hour post-dose.

The effects of h-19F6 and h-42A5 antibodies on haemostasis were assessed by a skin laceration-caused bleeding test in the same animals with $FeCl_3$-induced arterial thrombosis (n=5 per group). The bleeding times were recorded at pre-dose and 1-hour post-dose. No significant difference in bleeding time was observed between the pre-dose and 1-hour post-dose for either antibody or among the three groups 1-hour post-dose (FIG. 18).

Figure 12A:
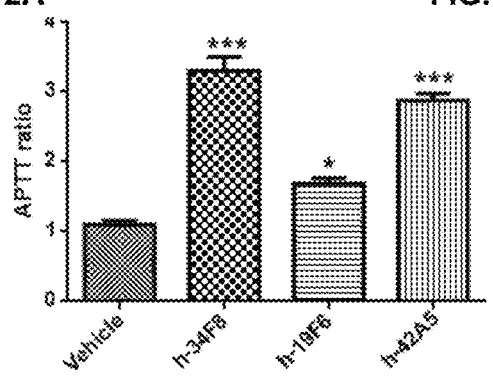
FIGS. 12A-12B illustrate the effects of antibodies h-34F8, h-19F6, and h-42A5 on clotting times of monkey plasma. Four groups of monkeys (n=5) were intravenously administered with the vehicle, 0.3 mg/kg of h-34F8, h-19F6, and h-42A5, respectively, and blood was collected pre-dose and about 3 hours post-dose for plasma preparation and clotting time APTT and PT determination. The APTT changes and PT changes are shown in (A) and (B), respectively. $P<0.01$ and *$P<0.001$ vs. vehicle.
Figure 12B:
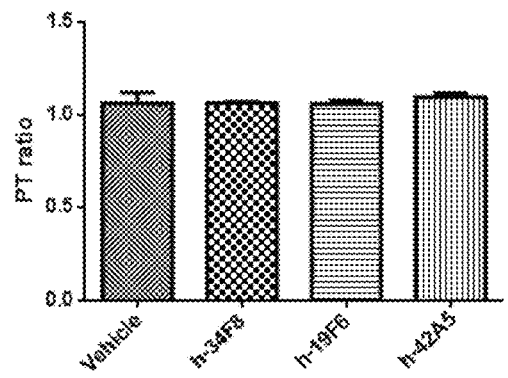

The effects of the antibodies on ex vivo clotting times of monkey plasma were also evaluated. As expected, treatments with 0.3 mg/kg of h-34F8, h-19F6, and h-42A5 significantly prolonged APTT by 3.29±0.20, 1.67±0.09, and 2.87±0.10 fold, respectively, while no increase in APTT was observed upon vehicle control treatment, as shown in FIG. 12A. In addition, treatments with h-34F8, h-19F6, or h-42A5 had no effect on PT as shown in FIG. 12B.

Thus, it was unexpectedly discovered that the antibodies disclosed herein did not have any adverse effects of prolonged bleeding while effectively inhibiting the intrinsic pathway of coagulation.

Figure 14A:
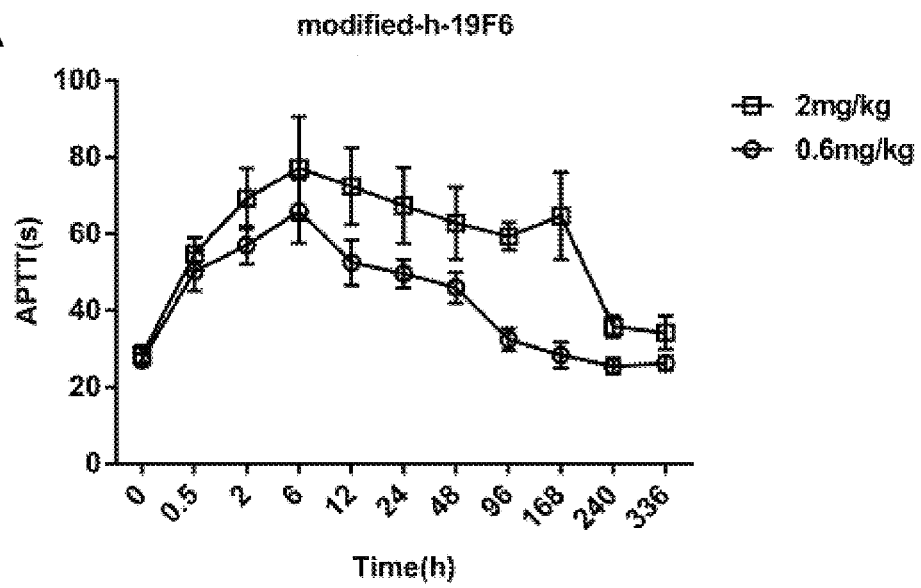
FIGS. 14A-14B illustrate the effects of modified antibodies h-19F6 (A), and h-42A5 (B) on APTT in cynomolgus monkeys. The monkeys were intravenously administered with indicated doses of modified h-19F6 and h-42A5. Ex vivo clotting time APTT was determined at pre-dose (time 0), and 0.5, 2, 6, 12, 24, 48, 96, 168, 240, and 336 hours post-dose.
Figure 14B:
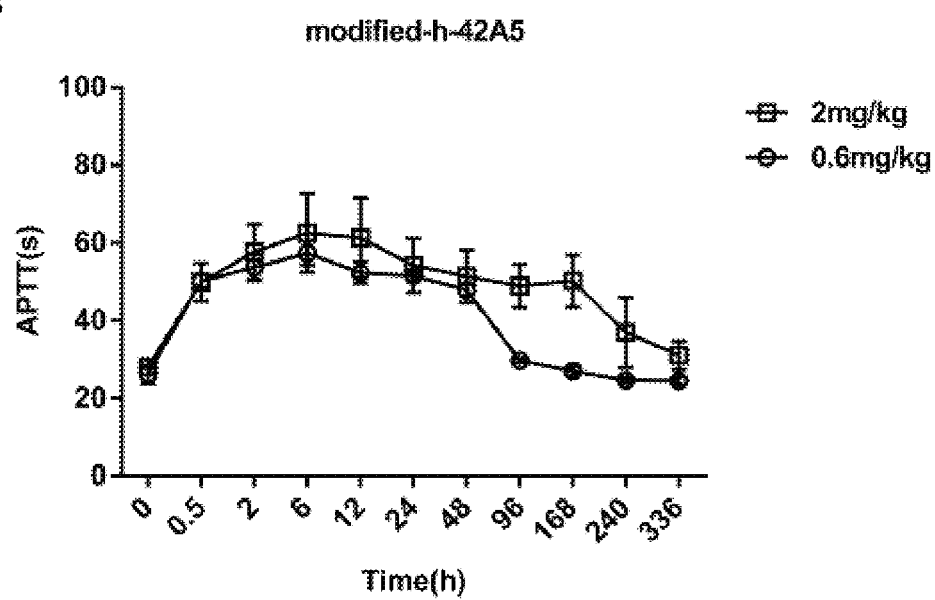
Figure 15A:
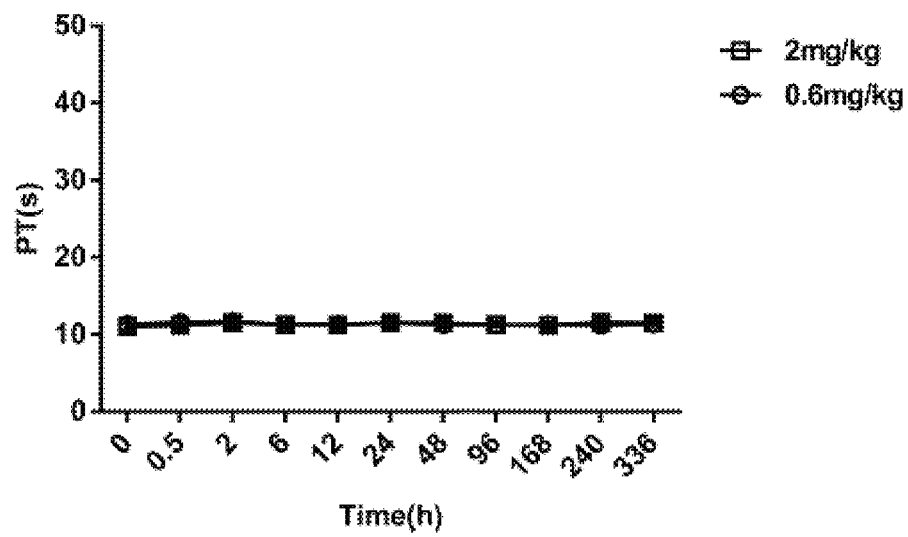
FIGS. 15A-15B illustrate the effects of modified antibodies h-19F6 (A), and h-42A5 (B) on PT in cynomolgus monkeys. Monkeys were intravenously administered with the indicated doses of modified h-19F6 and h-42A5. Ex vivo clotting time PT was determined at pre-dose (time 0), and 0.5, 2, 6, 12, 24, 48, 96, 168, 240, and 336 hours post-dose.
Figure 15B:
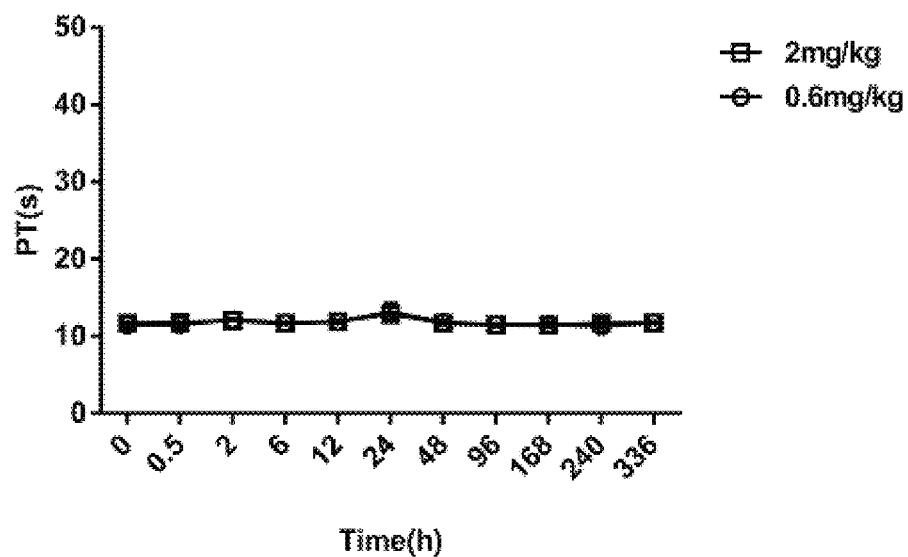

Example 13: Evaluation of the Effects of Modified Anti-FXI Antibodies on Clotting Time in Cynomolgus Monkeys for an Extended Period of Time Two additional CMC optimized, humanized anti-FXI antibodies, shown in FIGS. 14 and 15 as "modified h-19F6" and "modified h-42A5," were evaluated for their effects on clotting time in cynomolgus monkeys for an extended period of time, e.g., for up to 14 days, by APTT and PT assays as described in Example 10. The heavy chain and light chain sequences of these two antibodies are shown in Table 3. Cynomolgus monkeys were intravenously administered with 0.6 mg/kg or 2.0 mg/kg of the tested antibodies. Blood from the superficial veins of the upper limb was collected at pre-dose and at 0.5 hour, 2 hours, 6 hours, 12 hours, 24 hours, 48 hours, 96 hours, 168 hours, 240 hours, 336 hours post-dose. Both modified antibodies tested demonstrated dose-dependently increased APTT as shown in FIG. 14 and none of them affected PT as shown in FIG. 15. Both modified antibodies demonstrated efficacy for an extended period, up to 7 days, up to 10 days, or up to 14 days.

Thus, it was unexpectedly discovered that the modified antibodies disclosed herein did not show any adverse effects of prolonged bleeding while effectively inhibiting the intrinsic pathway of coagulation for an extended period of time, up to 14 days.

Example 14: Effects on Clotting Times of Standard Human Plasma

Figure 16B:
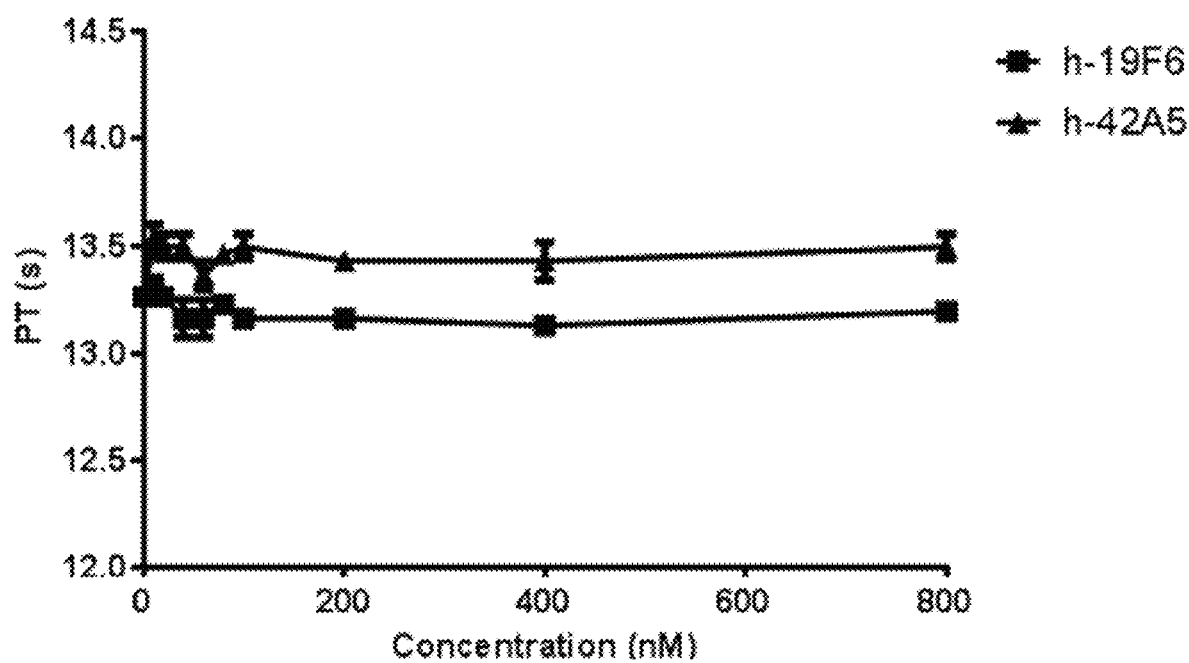

Antibodies h-19F6 and h-42A5 were added to normal human plasma, after which the APTT (FIG. 16A) and PT (FIG. 16B) were determined (N=3). Both h-19F6 and h-42A5 antibodies prolonged the activated partial thromboplastin time (APTT) of standard human plasma in a concentration-dependent manner (FIG. 16A). The maximum levels of inhibition of FXI activity in the plasma for h-19F6 and h-42A5 were approximately 97% and 99.5%, respectively, based on the correlation curve between plasma FXI level and APTT established (data not shown). Neither antibody affected the PT of human plasma (FIG. 16B).

Example 15: Binding Properties of h-19F6 and h-42A5 to FXI

Figure 17:
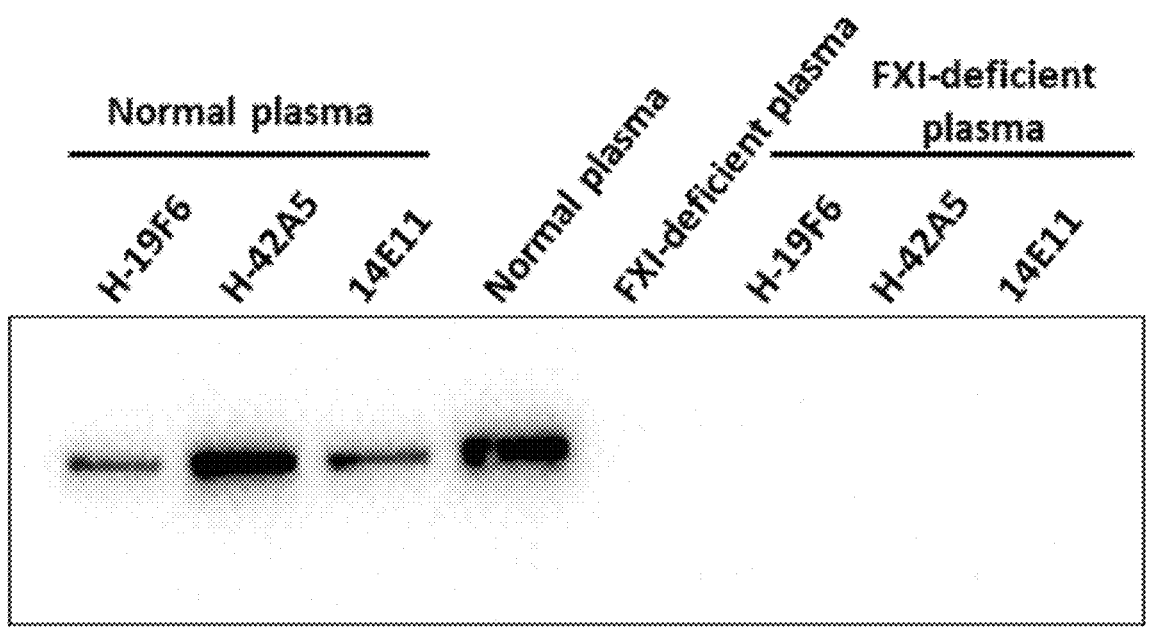
FIG. 17 shows the binding specificity of test antibodies to human FXI. In Western blotting, 10 µL of human standard plasma or FXI-deficient plasma were served as FXI-positive and FXI-negative controls.

The binding specificity of h-19F6 and h-42A5 to FXI were first verified as they reacted with FXI in standard human plasma and no reaction was detected in human FXI-deficient plasma (FIG. 17). Biotinylated test antibodies were incubated with human normal plasma or FXI-deficient plasma. The FXI-antibody complex in the plasma was eluted and subject to Western blotting using a mouse anti-human FXI IgG as the primary antibody. In Western blotting, 10 μL of human standard plasma or FXI-deficient plasma were served as FXI-positive and FXI-negative controls. A previously reported anti-FXI antibody, 14E11[17], showed the same binding profile as the two antibodies did (FIG. 17).

Figure 19A:
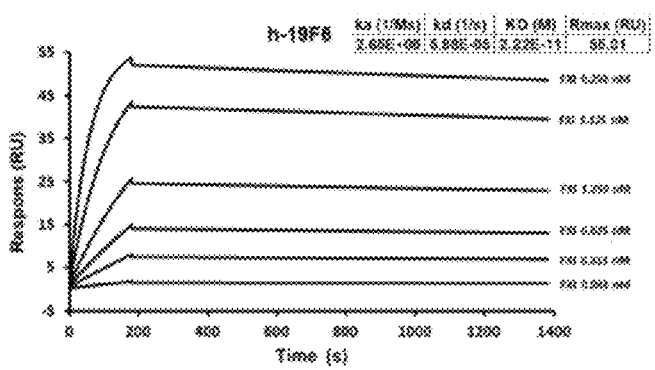
FIGS. 19A-19D show the binding properties of h-19F6 and h-42A5 to human FXI.
Figure 19B:
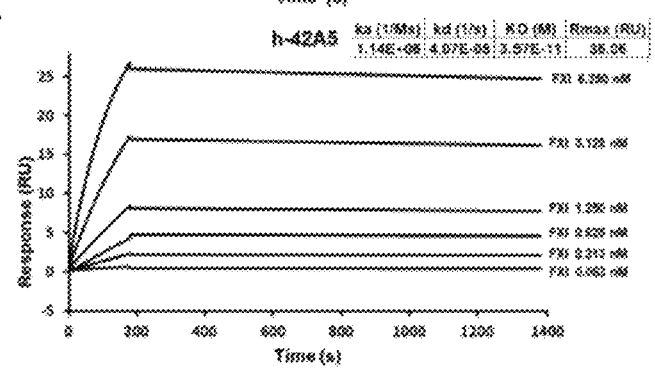

The affinities of h-19F6 and h-42A5 to FXI were determined using surface plasmon resonance (SPR) technology. The test antibodies were captured on a sensor chip, and then indicated concentrations of FXI were allowed to flow through the chip. Sensorgrams for h-19F6 (FIG. 19A) and h-42A5 (FIG. 19B) were obtained. The dissociation constants for h-19F6 and h-42A5 were 22 and 36 μM, respectively (FIGS. 19A and 19B).

Figure 19C:
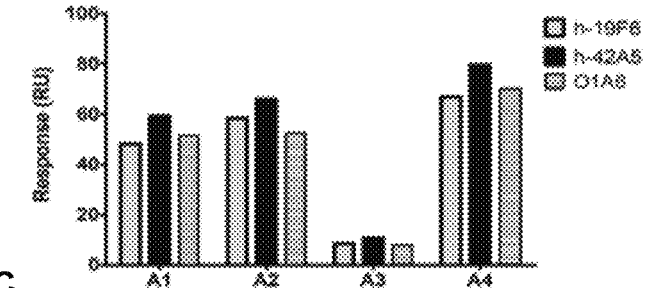
Figure 19D:
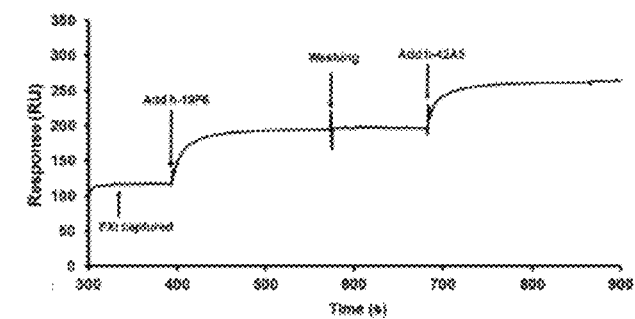

The binding sites of these two antibodies on FXI were then determined. FXI is a homodimer consisting of 4 tandem apple domains (A1-4) and a catalytic domain. Four mutants of FXI were generated by replacing each apple domain with corresponding domains from human prekallikrein and tested the binding properties of h-19F6 or h-42A5 to the 4 mutants of FXI using SPR. Equal amounts of the 4 mutant FXIs in which the A1, A2, A3, or A4 domain was replaced with the corresponding domain from prekallikrein were immobilized on a sensor chip, and test antibodies (5 μg/mL) were allowed to flow through the chip for association. The amounts of each antibody captured were recorded. The experiment was performed twice, and a representative result is depicted. Unexpectedly, both antibodies predominantly bound to the A3 domain of FXI, as replacement of the A3 domain resulted in much less binding of either antibody compared with the replacement of the other 3 apple domains (FIG. 19C). Another antibody, O1A6, a reported anti-FXI antibody used as a positive control, also specifically bound to the A3 domain of FXI, consistent with a previous study.[21] However, it was hypothesized that h-19F6 and h-42A5 bind different sites of FXI because they have comparable affinities to FXI but quite different inhibitory potencies with respect to FXI activity, as indicated in FIG. 16. This hypothesis was tested by epitope binding using a Biacore T200 system. Indeed, the binding of h-19F6 to FXI did not prevent the following binding of h-42A5 to FXI, indicating that the two antibodies bind different sites in the A3 domain of FXI (FIG. 19D). Then the flowing order of these two antibodies were changed and it was found that binding of h-42A5 to FXI did not prevent the following binding of h-19F6 to FXI (data not shown).

Example 16: Binding Properties of h-19F6 and h-42A5 to FXIa

Figure 20A:
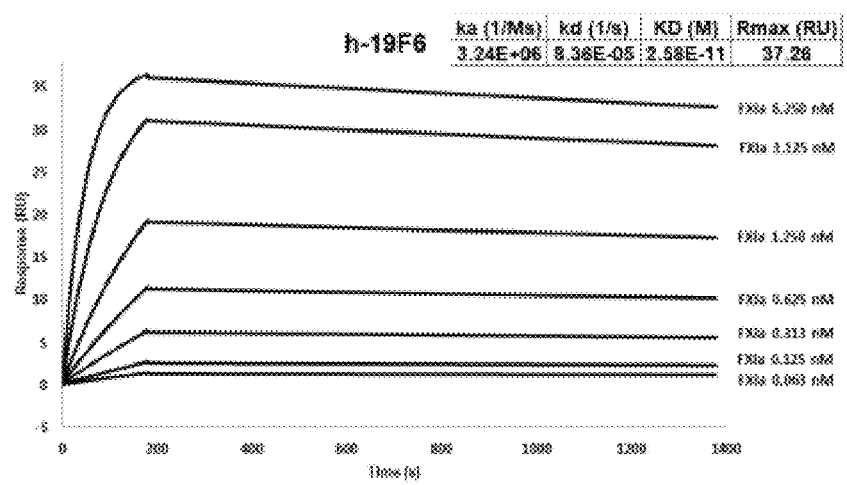
FIGS. 20A-20B show the binding properties of h-19F6 and h-42A5 to human FXIa.
Figure 20B:
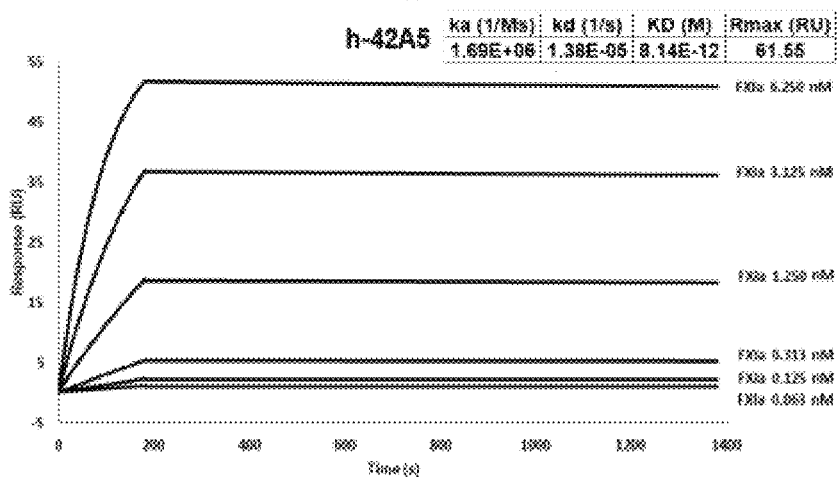

The antibodies bound to FXIa with the good affinities with which they bound to FXI (FIGS. 20A and 20B). The affinities of h-19F6 and h-42A5 to FXI were determined using surface plasmon resonance (SPR) technology. The dissociation constants for h-19F6 and h-42A5 were 26 and 81 µM, respectively (FIGS. 20A and 20B). The test antibodies were captured on a sensor chip, and then indicated concentrations of FXIa were allowed to flow through the chip. Sensorgrams for h-19F6 (FIG. 20A) and h-42A5 (FIG. 20B) were obtained.

REFERENCES

The references, patents and published patent applications listed below, and all references cited in the specification above are hereby incorporated by reference in their entirety, as if fully set forth herein.

1 Raskob, G. E. et al. Thrombosis: a major contributor to global disease burden. Arterioscler Thromb VascBiol 34, 2363-2371 (2014).
2 Gomez-Outes, A., Garcia-Fuentes, M. & Suarez-Gea, M. L. Discovery methods of coagulation-inhibiting drugs. Expert Opin Drug Discov 12, 1195-1205 (2017).
3 Weitz, J. I. & Fredenburgh, J. C. Factors XI and XII as Targets for New Anticoagulants. Front Med (Lausanne) 4, 19 (2017).
4 Muller, F., Gailani, D. & Renne, T. Factor XI and XII as antithrombotic targets. Curr Opin Hematol 18, 349-355 (2011).
5 Al-Horani, R. A. & Desai, U. R. Factor XIa inhibitors: A review of the patent literature. Expert Opin Ther Pat 26, 323-345 (2016).
6 Chen, Z., Seiffert, D. & Hawes, B. Inhibition of Factor XI activity as a promising antithrombotic strategy. Drug Discov Today 19, 1435-1439 (2014).
7 Gailani, D. & Gruber, A. Factor XI as a Therapeutic Target. Arterioscler Thromb Vasc Biol 36, 1316-1322 (2016).
8 Puy, C., Rigg, R. A. & McCarty, 0. J. The hemostatic role of factor XI. Thromb Res 141 Suppl 2, S8-S11 (2016).
9 Seligsohn, U. Factor XI deficiency in humans. J Thromb Haemost 7 Suppl 1, 84-87 (2009).
10 Preis, M. et al. Factor XI deficiency is associated with lower risk for cardiovascular and venous thromboembolism events. Blood 129, 1210-1215 (2017).
11 Meijers J. C., Tekelenburg W. L., Bouma B. N., Bertina R. M., Rosendaal F. R. High levels of coagulation factor XI as a risk factor for venous thrombosis. N Engl J Med 342, 696-701 (2000).
12 Peyvandi, F. et al. Coagulation factor activity and clinical bleeding severity in rare bleeding disorders: results from the European Network of Rare Bleeding Disorders. J Thromb Haemost 10, 615-621 (2012).
13 Salomon, O. & Seligsohn, U. New observations on factor XI deficiency. Haemophilia 10 Suppl 4, 184-187 (2004).
14 Wang, X. et al. Effects of factor IX or factor XI deficiency on ferric chloride-induced carotid artery occlusion in mice. J Thromb Haemost 3, 695-702 (2005).
15 Wang, X. et al. Inhibition of Factor XIa Reduces the Frequency of Cerebral Microembolic Signals Derived from Carotid Arterial Thrombosis in Rabbits. J Pharmacol Exp Ther 360, 476-483 (2017).
16 Wong, P. C., Crain, E. J., Watson, C. A. & Schumacher, W. A. A small-molecule factor XIa inhibitor produces antithrombotic efficacy with minimal bleeding time prolongation in rabbits. J Thromb Thrombolysis32, 129-137 (2011).
17 Cheng, Q. et al. A role for factor XIIa-mediated factor XI activation in thrombus formation in vivo. Blood 116, 3981-3989 (2010).
18 Takahashi, M. et al. Inhibition of factor XI reduces thrombus formation in rabbit jugular vein under endothelial denudation and/or blood stasis. Thromb Res 125, 464-470 (2010).
19 Yau, J. W. et al. Selective depletion of factor XI or factor XII with antisense oligonucleotides attenuates catheter thrombosis in rabbits. Blood 123, 2102-2107 (2014).
20 Crosby, J. R. et al. Antithrombotic effect of antisense factor XI oligonucleotide treatment in primates. Arterioscler Thromb Vasc Biol 33, 1670-1678 (2013).
21 Kravtsov D. V. et al. Factor XI contributes to thrombin generation in the absence of factor XII. Blood 114, 452-458 (2009).
22 Wang, X. et al. Effects of factor XI deficiency on ferric chloride-induced vena cava thrombosis in mice. J Thromb Haemost 4, 1982-1988 (2006).
23 Kleinschnitz, C. et al. Targeting coagulation factor XII provides protection from pathological thrombosis in cerebral ischemia without interfering with hemostasis. J Exp Med 203, 513-518 (2006).
24 Gailani, D., Lasky, N. M. & Broze, G. J., Jr. A murine model of factor XI deficiency. Blood Coagul Fibrinolysis 8, 134-144 (1997).
25 Beck, A., Wurch, T., Bailly, C. & Corvaia, N. Strategies and challenges for the next generation of therapeutic antibodies. Nat Rev Immunol 10, 345-352 (2010).
26 Tucker, E. I. et al. Prevention of vascular graft occlusion and thrombus-associated thrombin generation by inhibition of factor XI. Blood 113, 936-944 (2009).
27 Younis, H. S. et al. Antisense inhibition of coagulation factor XI prolongs APTT without increased bleeding risk in cynomolgus monkeys. Blood 119, 2401-2408 (2012).
28 Kouyama S, O. T., Hagio T, et al. Discovery of ONO-5450598, a highly orally bioavailable small molecule factor XIa inhibitor: the pharmacokinetic and pharmacological profiles. Res Pract Thromb Haemost 1 Suppl 1: PB 2139 (2017).

29. Wong, P. C. et al. In vitro, antithrombotic and bleeding time studies of BMS-654457, a small-molecule, reversible and direct inhibitor of factor XIa. J Thromb Thrombolysis 40, 416-423 (2015).
30. David, T. et al. Factor XIa-specific IgG and a reversal agent to probe factor XI function in thrombosis and hemostasis. Sci Transl Med 8, 353ra112 (2016).
31. van Montfoort, M. L. et al. Two novel inhibitory anti-human factor XI antibodies prevent cessation of blood flow in a murine venous thrombosis model. Thromb Haemost 110, 1065-1073 (2013).
32. Buller, H. R. et al. Factor XI antisense oligonucleotide for prevention of venous thrombosis. N Engl J Med 372, 232-240 (2015).
33. Emsley et al., *Blood* 115(13): 2569-2577 (2010).
34. Wang et al., *J. Pharm. Sciences* 96(1): 1-26 (2007).

What is claimed is:

1. An isolated anti-FXI or anti-FXIa antibody that specifically binds to human FXI or FXIa or immunologically active portion thereof wherein the antibody or portion thereof, comprises a combination of CDR selected from the group consisting of combinations a) to l):
   combination a) CDRs of SEQ ID NOs: 11-16;
   combination b) CDRs of SEQ ID NOs: 27-32;
   combination c) CDRs of SEQ ID NOs: 43-48;
   combination d) CDRs of SEQ ID NOs: 59-64;
   combination e) CDRs of SEQ ID NOs: 75-80;
   combination f) CDRs of SEQ ID NOs: 91-96;
   combination g) CDRs of SEQ ID NOs: 107-112;
   combination h) CDRs of SEQ ID NOs: 123-128;
   combination i) CDRs of SEQ ID NOs: 139-144;
   combination j) CDRs of SEQ ID NOs: 155-160;
   combination k) CDRs of SEQ ID NOs: 171-176; and
   combination l) CDRs of SEQ ID NOs: 187-192.

2. The antibody or immunologically active portion thereof according to claim 1, wherein the antibody specifically binds to the A3 domain of the human FXI or FXIa.

3. An isolated anti-FXI or anti-FXIa antibody that specifically binds to human FXI or FXIa or immunologically active portion thereof, wherein the antibody comprises a pair of sequences selected from the group consisting of SEQ ID NOs: 9-10, SEQ ID NOs: 25-26, SEQ ID NOs: 41-42, SEQ ID NOs: 57-58, SEQ ID NOs: 73-74, SEQ ID NOs: 89-90, SEQ ID NOs: 105-106, SEQ ID NOs: 121-122, SEQ ID NOs: 137-138, SEQ ID NOs: 153-154, SEQ ID NOs: 169-170, SEQ ID NOs: 185-186, SEQ ID NOs: 197-198, SEQ ID NOs: 199-200, SEQ ID NOs: 201-202, SEQ ID NOs: 204-205, SEQ ID NOs: 206-207, and SEQ ID NOs: 208-209.

4. A pharmaceutical composition comprising the antibody or immunologically active portion thereof according to claim 1.

5. A method of inhibiting the formation of blood clots in a subject comprising administering to the subject a therapeutically effective amount of the antibody or immunologically active portion thereof according to claim 1.

6. A method of inhibiting the formation of blood clots in a subject comprising administering to the subject a therapeutically effective amount of the pharmaceutical composition of claim 4.

7. A method of treating or inhibiting the occurrence of thrombosis or a complication or condition associated with thrombosis comprising administering to a subject a therapeutically effective amount of the antibody or immunologically active portion thereof according to claim 1, wherein the administration does not compromise hemostasis of the subject.

8. A method of treating or inhibiting the occurrence of thrombosis or a complication or condition associated with thrombosis comprising administering to a subject a therapeutically effective amount of the pharmaceutical composition of claim 4, wherein the administration does not compromise hemostasis of the subject.

9. A method of treating or inhibiting the occurrence of sepsis comprising administering to a subject a therapeutically effective amount of the antibody or immunologically active portion thereof according to claim 1, wherein the administration does not compromise hemostasis of the subject.

10. A method of treating or inhibiting the occurrence of sepsis comprising administering to a subject a therapeutically effective amount of the pharmaceutical composition of claim 4, wherein the administration does not compromise hemostasis of the subject.

11. A method of producing the antibody or immunologically active portion thereof according to claim 1, comprising expressing a nucleic acid encoding the antibody cloned in an expression vector in a host cell.

12. The method of claim 11, further comprising purifying the expressed antibody from the host cell.

13. The method of claim 11, wherein the expression vector is a pTT5 vector or pcDNA3 vector.

14. The method of claim 11, wherein the host cell is a CHO cell or an HEK193T cell.

15. A pharmaceutical composition comprising the antibody or immunologically active portion thereof according to claim 3.

* * * * *

SEQUENCE LISTING

<160> NUMBER OF SEQ ID NOS: 209

<210> SEQ ID NO 1
<211> LENGTH: 333
<212> TYPE: DNA
<213> ORGANISM: Mus musculus

<400> SEQUENCE: 1

```
gacattgtgc tgacccaatc tccagcttct ttggctgtgt ctctagggca gagggccacc    60
atctcctgca gagccagcga aagtgttgat aattatgcca ttagtttat gaactggttc    120 caacagaaac caggacagcc acccaaactc ctcatctatg ctgcatccaa cctaggatcc    180
ggggtccctg ccaggtttag tggcagtggg tctgggacag acttcagcct caacatccat    240
cctatggagg aggatgatac tgcaatgtat ttctgtcagc aagataagga ggttccgtgg    300
acgttcggtg gaggcaccga gctggaaatc aaa                                 333
```

<210> SEQ ID NO 2
<211> LENGTH: 354
<212> TYPE: DNA
<213> ORGANISM: Mus musculus

<400> SEQUENCE: 2

```
caggtcactc tgaaagagtc tggccctggg atattgcagc cctcccagac cctcagtctg    60
acttgttctt tctctgggtt ttcactgaac actcctggta tgggtgtgag ctggattcgt    120
cagccttcag gaaagggtct ggaatggctg gcacacattt actgggatga tgacaagcgc    180
tttaacccat ccctgaagag ccgactcaca atctccaagg atacctccag agatcaggta    240
ttcctcatga tcaccagtgt ggacactgca gattctgcca catacttctg tgctcgaaaa    300
ggccgcgggc cctttactta ctggggccaa gggactctgg tcactgtctc ttca          354
```

<210> SEQ ID NO 3
<211> LENGTH: 45
<212> TYPE: DNA
<213> ORGANISM: Mus musculus

<400> SEQUENCE: 3

```
agagccagcg aaagtgttga taattatgcc attagttta tgaac                     45
```

<210> SEQ ID NO 4
<211> LENGTH: 21
<212> TYPE: DNA
<213> ORGANISM: Mus musculus

<400> SEQUENCE: 4

```
gctgcatcca acctaggatc c                                              21
```

<210> SEQ ID NO 5
<211> LENGTH: 27
<212> TYPE: DNA
<213> ORGANISM: Mus musculus

```
<400> SEQUENCE: 5
cagcaagata aggaggttcc gtggacg                                            27

<210> SEQ ID NO 6
<211> LENGTH: 21
<212> TYPE: DNA
<213> ORGANISM: Mus musculus

<400> SEQUENCE: 6
actcctggta tgggtgtgag c                                                  21

<210> SEQ ID NO 7
<211> LENGTH: 48
<212> TYPE: DNA
<213> ORGANISM: Mus musculus

<400> SEQUENCE: 7
cacatttact gggatgatga caagcgcttt aacccatccc tgaagagc                     48

<210> SEQ ID NO 8
<211> LENGTH: 24
<212> TYPE: DNA
<213> ORGANISM: Mus musculus

<400> SEQUENCE: 8
aaaggccgcg ggcccttttac ttac                                              24

<210> SEQ ID NO 9
<211> LENGTH: 111
<212> TYPE: PRT
<213> ORGANISM: Mus musculus

<400> SEQUENCE: 9
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Ala Ile Ser Phe Met Asn Trp Phe Gln Gln Lys Pro Gly Gln Pro Pro
        35                  40                  45

Lys Leu Leu Ile Tyr Ala Ala Ser Asn Leu Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Asp Lys
                85                  90                  95

Glu Val Pro Trp Thr Phe Gly Gly Gly Thr Glu Leu Glu Ile Lys
            100                 105                 110

```
<210> SEQ ID NO 10
<211> LENGTH: 118
<212> TYPE: PRT
<213> ORGANISM: Mus musculus

<400> SEQUENCE: 10
```

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Pro
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Phe Asn Pro Ser
        50                  55                  60

Leu Lys Ser Arg Leu Thr Ile Ser Lys Asp Thr Ser Arg Asp Gln Val
 65                  70                  75                  80

Phe Leu Met Ile Thr Ser Val Asp Thr Ala Asp Ser Ala Thr Tyr Phe
                    85                  90                  95

Cys Ala Arg Lys Gly Arg Gly Pro Phe Thr Tyr Trp Gly Gln Gly Thr
            100                 105                 110

Leu Val Thr Val Ser Ser
        115

<210> SEQ ID NO 11
<211> LENGTH: 15
<212> TYPE: PRT
<213> ORGANISM: Mus musculus

<400> SEQUENCE: 11

Arg Ala Ser Glu Ser Val Asp Asn Tyr Ala Ile Ser Phe Met Asn
 1               5                   10                  15

<210> SEQ ID NO 12
<211> LENGTH: 7
<212> TYPE: PRT
<213> ORGANISM: Mus musculus

<400> SEQUENCE: 12

Ala Ala Ser Asn Leu Gly Ser
 1               5

<210> SEQ ID NO 13
<211> LENGTH: 9
<212> TYPE: PRT
<213> ORGANISM: Mus musculus

<400> SEQUENCE: 13

Gln Gln Asp Lys Glu Val Pro Trp Thr
 1               5

<210> SEQ ID NO 14
<211> LENGTH: 7
<212> TYPE: PRT
<213> ORGANISM: Mus musculus

<400> SEQUENCE: 14

Thr Pro Gly Met Gly Val Ser
 1               5

<210> SEQ ID NO 15
<211> LENGTH: 16
<212> TYPE: PRT
<213> ORGANISM: Mus musculus

<400> SEQUENCE: 15

His Ile Tyr Trp Asp Asp Asp Lys Arg Phe Asn Pro Ser Leu Lys Ser
 1               5                   10                  15

<210> SEQ ID NO 16
<211> LENGTH: 8
<212> TYPE: PRT
<213> ORGANISM: Mus musculus

<400> SEQUENCE: 16

Lys Gly Arg Gly Pro Phe Thr Tyr
1               5

<210> SEQ ID NO 17
<211> LENGTH: 333
<212> TYPE: DNA
<213> ORGANISM: Mus musculus

<400> SEQUENCE: 17

| gacattgtgc tgacccaatc tccagcctct ttgctgtgt ctctagggca gagggccacc | 60 |
| atctcctgca gagccagcga aagtgttgat aattatggca ttagttttct gaactggttc | 120 |
| caacagaaac caggacagcc acccaaactc ctcatctatg ctgcatccaa tctaggatcc | 180 |
| ggggtccctg ccaggtttag tggcagtggg tctgggacag acttcagcct caacatccat | 240 |
| cctatggagg aggatgatac tgcaatgtat ttctgtcagc aagataaggg ggttccgtgg | 300 |
| acgttcggtg gaggcaccaa gctggaaatg aaa | 333 |

<210> SEQ ID NO 18
<211> LENGTH: 354
<212> TYPE: DNA
<213> ORGANISM: Mus musculus

<400> SEQUENCE: 18

| caggttactc tgaaagagtc tggccctggg atattgcagc cctcccagac cctcagtctg | 60 |
| acttgttctt tctctgggtt ttcactgaac acttctggta tgggtgtgag ctggattcgt | 120 |
| cagccttcag gaaagggtct ggagtggctg gcacacattt actgggatga tgacaagcgc | 180 |
| tataaaccat ccctgaagag ccggctcaca atctccaagg atacctccag aaaccaggta | 240 |
| ttcctcatga tcaccagtgt ggacactgca gatactgcca catactactg tgttcgaaaa | 300 |
| ggccgcgggc cctttgctaa ctggggccaa gggactctgg tcactgtctc tgca | 354 |

<210> SEQ ID NO 19
<211> LENGTH: 45
<212> TYPE: DNA
<213> ORGANISM: Mus musculus

<400> SEQUENCE: 19

| agagccagcg aaagtgttga taattatggc attagttttc tgaac | 45 |

<210> SEQ ID NO 20
<211> LENGTH: 21
<212> TYPE: DNA
<213> ORGANISM: Mus musculus

<400> SEQUENCE: 20

| gctgcatcca atctaggatc c | 21 |

<210> SEQ ID NO 21
<211> LENGTH: 27
<212> TYPE: DNA
<213> ORGANISM: Mus musculus

<400> SEQUENCE: 21

| cagcaagata agggggttcc gtggacg | 27 |

```
<210> SEQ ID NO 22
<211> LENGTH: 21
<212> TYPE: DNA
<213> ORGANISM: Mus musculus

<400> SEQUENCE: 22
acttctggta tgggtgtgag c                                              21

<210> SEQ ID NO 23
<211> LENGTH: 48
<212> TYPE: DNA
<213> ORGANISM: Mus musculus

<400> SEQUENCE: 23
cacatttact gggatgatga caagcgctat aaaccatccc tgaagagc                 48

<210> SEQ ID NO 24
<211> LENGTH: 24
<212> TYPE: DNA
<213> ORGANISM: Mus musculus

<400> SEQUENCE: 24
aaaggccgcg ggccctttgc taac                                           24

<210> SEQ ID NO 25
<211> LENGTH: 111
<212> TYPE: PRT
<213> ORGANISM: Mus musculus

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Leu Asn Trp Phe Gln Gln Lys Pro Gly Gln Pro Pro
        35                  40                  45

Lys Leu Leu Ile Tyr Ala Ala Ser Asn Leu Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Asp Lys
                85                  90                  95

Gly Val Pro Trp Thr Phe Gly Gly Gly Thr Lys Leu Glu Met Lys
            100                 105                 110

<210> SEQ ID NO 26
<211> LENGTH: 118
<212> TYPE: PRT
<213> ORGANISM: Mus musculus

<400> SEQUENCE: 26

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Lys Pro Ser
    50                  55                  60
```

```
Leu Lys Ser Arg Leu Thr Ile Ser Lys Asp Thr Ser Arg Asn Gln Val
 65                  70                  75                  80

Phe Leu Met Ile Thr Ser Val Asp Thr Ala Asp Thr Ala Thr Tyr Tyr
                 85                  90                  95

Cys Val Arg Lys Gly Arg Gly Pro Phe Ala Asn Trp Gly Gln Gly Thr
            100                 105                 110

Leu Val Thr Val Ser Ala
            115
```

<210> SEQ ID NO 27
<211> LENGTH: 15
<212> TYPE: PRT
<213> ORGANISM: Mus musculus

<400> SEQUENCE: 27

```
Arg Ala Ser Glu Ser Val Asp Asn Tyr Gly Ile Ser Phe Leu Asn
 1               5                  10                  15
```

<210> SEQ ID NO 28
<211> LENGTH: 7
<212> TYPE: PRT
<213> ORGANISM: Mus musculus

<400> SEQUENCE: 28

```
Ala Ala Ser Asn Leu Gly Ser
 1               5
```

<210> SEQ ID NO 29
<211> LENGTH: 9
<212> TYPE: PRT
<213> ORGANISM: Mus musculus

<400> SEQUENCE: 29

```
Gln Gln Asp Lys Gly Val Pro Trp Thr
 1               5
```

<210> SEQ ID NO 30
<211> LENGTH: 7
<212> TYPE: PRT
<213> ORGANISM: Mus musculus

<400> SEQUENCE: 30

```
Thr Ser Gly Met Gly Val Ser
 1               5
```

<210> SEQ ID NO 31
<211> LENGTH: 16
<212> TYPE: PRT
<213> ORGANISM: Mus musculus

<400> SEQUENCE: 31

```
His Ile Tyr Trp Asp Asp Lys Arg Tyr Lys Pro Ser Leu Lys Ser
 1               5                  10                  15
```

<210> SEQ ID NO 32
<211> LENGTH: 8
<212> TYPE: PRT
<213> ORGANISM: Mus musculus

<400> SEQUENCE: 32

```
Lys Gly Arg Gly Pro Phe Ala Asn
 1               5
```

```
<210> SEQ ID NO 33
<211> LENGTH: 321
<212> TYPE: DNA
<213> ORGANISM: Mus musculus

<400> SEQUENCE: 33
gacatccaga tgacccagtc tccatcctcc ttatctgcct ctctgggaga aagagtcagt    60
ctcacttgtc gggcaagtca ggacattgat attcgcttaa actggcttcg acaggaacca   120
gatggaacta ttaaacgcct gatctacgcc acatccagtt tagattctgg tgtccccaaa   180
aggttcagtg gcagtaggtc tgggtcagat tattctctca ccatcagcag ccttgagtct   240
gaagattttg ttgactatta ctgtctacaa tatgctagtt ctccattcac gttcggctcg   300
gggacaaagt tggaaataaa a                                             321

<210> SEQ ID NO 34
<211> LENGTH: 354
<212> TYPE: DNA
<213> ORGANISM: Mus musculus

<400> SEQUENCE: 34
cagatccagt tggtgcagtc tggacctgaa ctgaagaagc ctggagagac cgtcaagatc    60
tcctgcaagg cttctgggta tatttttcaca gactatggaa tgaactgggt gaagcaggct   120
ccaggaaagg gtttaaagtg gatgggctgg ataaacacct acactggaga gccaacatat   180
gctgatgact tcaagggacg gtttgtcttc tctttggaaa cctctgccag cactgcctat   240
ttacagatca caaacctcaa aaatgaggac acggctacat ttttctgtgc aagaaggagg   300
atgggttatg ctgtggacta ctgggggtcaa ggaacctcag tcaccgtctc ctca         354

<210> SEQ ID NO 35
<211> LENGTH: 33
<212> TYPE: DNA
<213> ORGANISM: Mus musculus

<400> SEQUENCE: 35
cgggcaagtc aggacattga tattcgctta aac                                 33

<210> SEQ ID NO 36
<211> LENGTH: 21
<212> TYPE: DNA
<213> ORGANISM: Mus musculus

<400> SEQUENCE: 36
gccacatcca gtttagattc t                                              21

<210> SEQ ID NO 37
<211> LENGTH: 27
<212> TYPE: DNA
<213> ORGANISM: Mus musculus

<400> SEQUENCE: 37
ctacaatatg ctagttctcc attcacg                                        27

<210> SEQ ID NO 38
<211> LENGTH: 15
<212> TYPE: DNA
<213> ORGANISM: Mus musculus

<400> SEQUENCE: 38
gactatggaa tgaac                                                     15
```

<210> SEQ ID NO 39
<211> LENGTH: 51
<212> TYPE: DNA
<213> ORGANISM: Mus musculus

<400> SEQUENCE: 39
tggataaaca cctacactgg agagccaaca tatgctgatg acttcaaggg a        51

<210> SEQ ID NO 40
<211> LENGTH: 27
<212> TYPE: DNA
<213> ORGANISM: Mus musculus

<400> SEQUENCE: 40
aggaggatgg gttatgctgt ggactac        27

<210> SEQ ID NO 41
<211> LENGTH: 107
<212> TYPE: PRT
<213> ORGANISM: Mus musculus

<400> SEQUENCE: 41

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Asp Ile Arg
            20                  25                  30

Leu Asn Trp Leu Arg Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Phe
                85                  90                  95

Thr Phe Gly Ser Gly Thr Lys Leu Glu Ile Lys
            100                 105

<210> SEQ ID NO 42
<211> LENGTH: 118
<212> TYPE: PRT
<213> ORGANISM: Mus musculus

<400> SEQUENCE: 42

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asp Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Thr Ala Thr Phe Phe Cys
                85                  90                  95

Ala Arg Arg Arg Met Gly Tyr Ala Val Asp Tyr Trp Gly Gln Gly Thr
            100                 105                 110

Ser Val Thr Val Ser Ser
            115

<210> SEQ ID NO 43
<211> LENGTH: 11
<212> TYPE: PRT
<213> ORGANISM: Mus musculus

<400> SEQUENCE: 43

Arg Ala Ser Gln Asp Ile Asp Ile Arg Leu Asn
1               5                   10

<210> SEQ ID NO 44
<211> LENGTH: 7
<212> TYPE: PRT
<213> ORGANISM: Mus musculus

<400> SEQUENCE: 44

Ala Thr Ser Ser Leu Asp Ser
1               5

<210> SEQ ID NO 45
<211> LENGTH: 9
<212> TYPE: PRT
<213> ORGANISM: Mus musculus

<400> SEQUENCE: 45

Leu Gln Tyr Ala Ser Ser Pro Phe Thr
1               5

<210> SEQ ID NO 46
<211> LENGTH: 5
<212> TYPE: PRT
<213> ORGANISM: Mus musculus

<400> SEQUENCE: 46

Asp Tyr Gly Met Asn
1               5

<210> SEQ ID NO 47
<211> LENGTH: 17
<212> TYPE: PRT
<213> ORGANISM: Mus musculus

<400> SEQUENCE: 47

Trp Ile Asn Thr Tyr Thr Gly Glu Pro Thr Tyr Ala Asp Asp Phe Lys
1               5                   10                  15

Gly

<210> SEQ ID NO 48
<211> LENGTH: 9
<212> TYPE: PRT
<213> ORGANISM: Mus musculus

<400> SEQUENCE: 48

Arg Arg Met Gly Tyr Ala Val Asp Tyr
1               5

<210> SEQ ID NO 49
<211> LENGTH: 333
<212> TYPE: DNA
<213> ORGANISM: Mus musculus

<400> SEQUENCE: 49
gacattgtgc tgacccaatc tccagcttct ttggctgtgt ctctagggca gagggccacc      60
atctcctgca gagccagcga aagtgttgat aattatgcca ttagttttat gaattggttc     120

```
caacagaaac caggacagcc acccaaactc ctcatctatg ctgcatccaa cctaggatcc    180
ggggtccctg ccaggtttag tggcagtggg tctgggacag acttcagcct caacatccat    240
cctatggagg aggatgatac tgcaatgtat ttctgtcagc aagataagga ggttccgtgg    300
acgttcggtg gaggcaccaa gctggagctg aaa                                 333

<210> SEQ ID NO 50
<211> LENGTH: 354
<212> TYPE: DNA
<213> ORGANISM: Mus musculus

<400> SEQUENCE: 50
caggttactc tgaaagagtc tggccctggg atagtgcagc cctcccagac cctcaatctg     60
acttgttctt tctctggatt tcactgagc acttctggta tgggtgtgag ctggattcgt    120
cagccttcag gaaagggtct ggattggctg gcacacattt actgggatga tgacaagcgc    180
tataacccat ccctgatgag ccggctcaca atctccaagg atacctccag aaaccaggta    240
ttcctcatga tcaccagtgt ggacactgca gatactgcca catactactg tgctcgaaaa    300
ggccgcgggc cctttgctta ctggggccaa gggactctgg tcactgtctc ttca          354

<210> SEQ ID NO 51
<211> LENGTH: 45
<212> TYPE: DNA
<213> ORGANISM: Mus musculus

<400> SEQUENCE: 51
agagccagcg aaagtgttga taattatgcc attagttta tgaat                      45

<210> SEQ ID NO 52
<211> LENGTH: 21
<212> TYPE: DNA
<213> ORGANISM: Mus musculus

<400> SEQUENCE: 52
gctgcatcca acctaggatc c                                               21

<210> SEQ ID NO 53
<211> LENGTH: 27
<212> TYPE: DNA
<213> ORGANISM: Mus musculus

<400> SEQUENCE: 53
cagcaagata aggaggttcc gtggacg                                         27

<210> SEQ ID NO 54
<211> LENGTH: 21
<212> TYPE: DNA
<213> ORGANISM: Mus musculus

<400> SEQUENCE: 54
acttctggta tgggtgtgag c                                               21

<210> SEQ ID NO 55
<211> LENGTH: 48
<212> TYPE: DNA
<213> ORGANISM: Mus musculus
```

<400> SEQUENCE: 55
cacatttact gggatgatga caagcgctat aacccatccc tgatgagc          48

<210> SEQ ID NO 56
<211> LENGTH: 24
<212> TYPE: DNA
<213> ORGANISM: Mus musculus

<400> SEQUENCE: 56
aaaggccgcg ggccctttgc ttac                                    24

<210> SEQ ID NO 57
<211> LENGTH: 111
<212> TYPE: PRT
<213> ORGANISM: Mus musculus

<400> SEQUENCE: 57

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Ala Ile Ser Phe Met Asn Trp Phe Gln Gln Lys Pro Gly Gln Pro Pro
        35                  40                  45

Lys Leu Leu Ile Tyr Ala Ala Ser Asn Leu Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Asp Lys
                85                  90                  95

Glu Val Pro Trp Thr Phe Gly Gly Gly Thr Lys Leu Glu Leu Lys
            100                 105                 110

<210> SEQ ID NO 58
<211> LENGTH: 118
<212> TYPE: PRT
<213> ORGANISM: Mus musculus

<400> SEQUENCE: 58

Gln Val Thr Leu Lys Glu Ser Gly Pro Gly Ile Val Gln Pro Ser Gln
1               5                   10                  15

Thr Leu Asn Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Asp
        35                  40                  45

Trp Leu Ala His Ile Tyr Trp Asp Asp Asp Lys Arg Tyr Asn Pro Ser
    50                  55                  60

Leu Met Ser Arg Leu Thr Ile Ser Lys Asp Thr Ser Arg Asn Gln Val
65                  70                  75                  80

Phe Leu Met Ile Thr Ser Val Asp Thr Ala Asp Thr Ala Thr Tyr Tyr
                85                  90                  95

Cys Ala Arg Lys Gly Arg Gly Pro Phe Ala Tyr Trp Gly Gln Gly Thr
            100                 105                 110

Leu Val Thr Val Ser Ser
            115

<210> SEQ ID NO 59
<211> LENGTH: 15
<212> TYPE: PRT
<213> ORGANISM: Mus musculus

<400> SEQUENCE: 59

Arg Ala Ser Glu Ser Val Asp Asn Tyr Ala Ile Ser Phe Met Asn
1               5                   10                  15

<210> SEQ ID NO 60
<211> LENGTH: 7
<212> TYPE: PRT
<213> ORGANISM: Mus musculus

<400> SEQUENCE: 60

Ala Ala Ser Asn Leu Gly Ser
1               5

<210> SEQ ID NO 61
<211> LENGTH: 9
<212> TYPE: PRT
<213> ORGANISM: Mus musculus

<400> SEQUENCE: 61

Gln Gln Asp Lys Glu Val Pro Trp Thr
1               5

<210> SEQ ID NO 62
<211> LENGTH: 7
<212> TYPE: PRT
<213> ORGANISM: Mus musculus

<400> SEQUENCE: 62

Thr Ser Gly Met Gly Val Ser
1               5

<210> SEQ ID NO 63
<211> LENGTH: 16
<212> TYPE: PRT
<213> ORGANISM: Mus musculus

<400> SEQUENCE: 63

His Ile Tyr Trp Asp Asp Asp Lys Arg Tyr Asn Pro Ser Leu Met Ser
1               5                   10                  15

<210> SEQ ID NO 64
<211> LENGTH: 8
<212> TYPE: PRT
<213> ORGANISM: Mus musculus

<400> SEQUENCE: 64

Lys Gly Arg Gly Pro Phe Ala Tyr
1               5

<210> SEQ ID NO 65
<211> LENGTH: 333
<212> TYPE: DNA
<213> ORGANISM: Mus musculus

<400> SEQUENCE: 65
cagttcacgc tgactcaacc aaagtccgtg tcaggatctt taagaagcac tatcaccatt      60
ccctgtgagc gcagcagtgg tgacattgga gatagctatg tgagctggta ccaacaacac     120
ttgggaagac ccccatcaa tgtgatctat gctgatgatc aaagaccatc tgaagtgtct      180
gctcggttct cgggctccat cgacagctcc tctaactcag cctcactgac catcactaat     240
ctacagatgg atgatgaggc cgactacttc tgtcagtctt acgatactta tatggatgtt     300
gtgttcggtg gtggaaccaa gctcaatgtc cta                                   333

```
<210> SEQ ID NO 66
<211> LENGTH: 360
<212> TYPE: DNA
<213> ORGANISM: Mus musculus

<400> SEQUENCE: 66
gaggtgcagc tgaaggaatc aggacctggt ctggtgcagc cctcacagac cctgtccctc      60
acctgcactg tctctggatt ctcattaacg gactacagtg tacactgggt tcgccagcct     120
ccaggaaaag gtctggagtg gatgggagta atgtggagtg gtggaagcac agcatataat     180
ccagctctca catcccgact gaccattagc aggacacct ccaagagcca gttttcttta      240
aaaatgaaca gtctgcaaac tgaagataca gccatttact actgtaccag agcacctttt     300
aacaactggg gcaattggct tccttactgg ggccaaggca ctctggtcac tgtctcttca     360

<210> SEQ ID NO 67
<211> LENGTH: 39
<212> TYPE: DNA
<213> ORGANISM: Mus musculus

<400> SEQUENCE: 67
gagcgcagca gtggtgacat tggagatagc tatgtgagc                              39

<210> SEQ ID NO 68
<211> LENGTH: 21
<212> TYPE: DNA
<213> ORGANISM: Mus musculus

<400> SEQUENCE: 68
gctgatgatc aaagaccatc t                                                 21

<210> SEQ ID NO 69
<211> LENGTH: 30
<212> TYPE: DNA
<213> ORGANISM: Mus musculus

<400> SEQUENCE: 69
cagtcttacg atacttatat ggatgttgtg                                        30

<210> SEQ ID NO 70
<211> LENGTH: 15
<212> TYPE: DNA
<213> ORGANISM: Mus musculus

<400> SEQUENCE: 70
gactacagtg tacac                                                        15

<210> SEQ ID NO 71
<211> LENGTH: 48
<212> TYPE: DNA
<213> ORGANISM: Mus musculus

<400> SEQUENCE: 71
gtaatgtgga gtggtggaag cacagcatat aatccagctc tcacatcc                    48

<210> SEQ ID NO 72
<211> LENGTH: 36
<212> TYPE: DNA
<213> ORGANISM: Mus musculus

<400> SEQUENCE: 72 gcaccttta acaactgggg caattggctt ccttac                                  36
```

<210> SEQ ID NO 73
<211> LENGTH: 111
<212> TYPE: PRT
<213> ORGANISM: Mus musculus

<400> SEQUENCE: 73

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Ser
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Ala Arg Phe Ser
    50                  55                  60

Gly Ser Ile Asp Ser Ser Ser Asn Ser Ala Ser Leu Thr Ile Thr Asn
65                  70                  75                  80

Leu Gln Met Asp Asp Glu Ala Asp Tyr Phe Cys Gln Ser Tyr Asp Thr
                85                  90                  95

Tyr Met Asp Val Val Phe Gly Gly Gly Thr Lys Leu Asn Val Leu
            100                 105                 110

<210> SEQ ID NO 74
<211> LENGTH: 120
<212> TYPE: PRT
<213> ORGANISM: Mus musculus

<400> SEQUENCE: 74

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asp Tyr
            20                  25                  30

Ser Val His Trp Val Arg Gln Pro Pro Gly Lys Gly Leu Glu Trp Met
        35                  40                  45

Gly Val Met Trp Ser Gly Gly Ser Thr Ala Tyr Asn Pro Ala Leu Thr
    50                  55                  60

Ser Arg Leu Thr Ile Ser Arg Asp Thr Ser Lys Ser Gln Val Phe Leu
65                  70                  75                  80

Lys Met Asn Ser Leu Gln Thr Glu Asp Thr Ala Ile Tyr Tyr Cys Thr
                85                  90                  95

Arg Ala Pro Phe Asn Asn Trp Gly Asn Trp Leu Pro Tyr Trp Gly Gln
            100                 105                 110

Gly Thr Leu Val Thr Val Ser Ser
        115                 120

<210> SEQ ID NO 75
<211> LENGTH: 13
<212> TYPE: PRT
<213> ORGANISM: Mus musculus

<400> SEQUENCE: 75

Glu Arg Ser Ser Gly Asp Ile Gly Asp Ser Tyr Val Ser
1               5                   10

<210> SEQ ID NO 76
<211> LENGTH: 7
<212> TYPE: PRT
<213> ORGANISM: Mus musculus

<400> SEQUENCE: 76

Ala Asp Asp Gln Arg Pro Ser
1               5

<210> SEQ ID NO 77
<211> LENGTH: 10
<212> TYPE: PRT
<213> ORGANISM: Mus musculus

<400> SEQUENCE: 77

Gln Ser Tyr Asp Thr Tyr Met Asp Val Val
1               5                   10

<210> SEQ ID NO 78
<211> LENGTH: 5
<212> TYPE: PRT
<213> ORGANISM: Mus musculus

<400> SEQUENCE: 78

Asp Tyr Ser Val His
1               5

<210> SEQ ID NO 79
<211> LENGTH: 16
<212> TYPE: PRT
<213> ORGANISM: Mus musculus

<400> SEQUENCE: 79

Val Met Trp Ser Gly Gly Ser Thr Ala Tyr Asn Pro Ala Leu Thr Ser
1               5                   10                  15

<210> SEQ ID NO 80
<211> LENGTH: 12
<212> TYPE: PRT
<213> ORGANISM: Mus musculus

<400> SEQUENCE: 80

Ala Pro Phe Asn Asn Trp Gly Asn Trp Leu Pro Tyr
1               5                   10

<210> SEQ ID NO 81
<211> LENGTH: 339
<212> TYPE: DNA
<213> ORGANISM: Mus musculus

<400> SEQUENCE: 81
caattcacgc tgactcaacc aaagtccgtg tcaggctctt taagaagcac tatcaccatt      60
ccctgtgagc gcagcagtgg tgacattgga gatagctatg tgagctggta ccagcaacac     120
ttgggaagac cccccatcaa tgtgatctat gctgatgatc aaagaccatc tgaagtgtct     180
gatcggttct cgggctccat cgacacctcc tctaactcag cctcactgac catcactaat     240
ctgcagatgg atgatgcggc cgactacttc tgtcagtctt acgatagtaa tattgatttt     300
aaccctgttt tcggtggtgg aaccaagctc actgtccta                            339

<210> SEQ ID NO 82
<211> LENGTH: 363
<212> TYPE: DNA
<213> ORGANISM: Mus musculus -continued

<400> SEQUENCE: 82

```
gaggtgcagc tggtggagtc tgtggaggc ttagtgcagc ctggaaggtc tctgagactc      60
tcctgtacag cctcaggatt cactttcagt aaatatgtca tggcctgggt ccgccaggct    120
ccaacgaagg ggctggagtg ggtcgcatcc attaattatg atggtagtac cacttactat    180
cgagactccg tgcagggccg gttcactctc tccagagata tgcaaaaac caccctatac     240
ctgcaaatgg acagtctgag gtctgaggac acggccactt attactgtgc aaggcaccct    300
tttaacaact cgggatttg gtttgcttac tggggccaag gcactctggt cactgtctct     360
tca                                                                   363
```

<210> SEQ ID NO 83
<211> LENGTH: 39
<212> TYPE: DNA
<213> ORGANISM: Mus musculus

<400> SEQUENCE: 83

```
gagcgcagca gtggtgacat tggagatagc tatgtgagc                            39
```

<210> SEQ ID NO 84
<211> LENGTH: 21
<212> TYPE: DNA
<213> ORGANISM: Mus musculus

<400> SEQUENCE: 84

```
gctgatgatc aaagaccatc t                                               21
```

<210> SEQ ID NO 85
<211> LENGTH: 36
<212> TYPE: DNA
<213> ORGANISM: Mus musculus

<400> SEQUENCE: 85

```
cagtcttacg atagtaatat tgattttaac cctgtt                               36
```

<210> SEQ ID NO 86
<211> LENGTH: 15
<212> TYPE: DNA
<213> ORGANISM: Mus musculus

<400> SEQUENCE: 86

```
aaatatgtca tggcc                                                      15
```

<210> SEQ ID NO 87
<211> LENGTH: 51
<212> TYPE: DNA
<213> ORGANISM: Mus musculus

<400> SEQUENCE: 87

```
tccattaatt atgatggtag taccacttac tatcgagact ccgtgcaggg c              51
```

<210> SEQ ID NO 88
<211> LENGTH: 36
<212> TYPE: DNA
<213> ORGANISM: Mus musculus

<400> SEQUENCE: 88

```
caccctttta caacttcgg gatttggttt gcttac                                36
```

```
<210> SEQ ID NO 89
<211> LENGTH: 113
<212> TYPE: PRT
<213> ORGANISM: Mus musculus

<400> SEQUENCE: 89

Gln Phe Thr Leu Thr Gln Pro Lys Ser Val Ser Gly Ser Leu Arg Ser
1               5                   10                  15

Thr Ile Thr Ile Pro Cys Glu Arg Ser Ser Gly Asp Ile Gly Asp Ser
            20                  25                  30

Tyr Val Ser Trp Tyr Gln Gln His Leu Gly Arg Pro Pro Ile Asn Val
        35                  40                  45

Ile Tyr Ala Asp Asp Gln Arg Pro Ser Glu Val Ser Asp Arg Phe Ser
    50                  55                  60

Gly Ser Ile Asp Thr Ser Ser Asn Ser Ala Ser Leu Thr Ile Thr Asn
65                  70                  75                  80

Leu Gln Met Asp Asp Ala Ala Asp Tyr Phe Cys Gln Ser Tyr Asp Ser
                85                  90                  95

Asn Ile Asp Phe Asn Pro Val Phe Gly Gly Gly Thr Lys Leu Thr Val
            100                 105                 110

Leu

<210> SEQ ID NO 90
<211> LENGTH: 121
<212> TYPE: PRT
<213> ORGANISM: Mus musculus

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Lys Tyr
            20                  25                  30

Val Met Ala Trp Val Arg Gln Ala Pro Thr Lys Gly Leu Glu Trp Val
        35                  40                  45

Ala Ser Ile Asn Tyr Asp Gly Ser Thr Thr Tyr Tyr Arg Asp Ser Val
    50                  55                  60

Gln Gly Arg Phe Thr Leu Ser Arg Asp Asn Ala Lys Thr Thr Leu Tyr
65                  70                  75                  80

Leu Gln Met Asp Ser Leu Arg Ser Glu Asp Thr Ala Thr Tyr Tyr Cys
                85                  90                  95

Ala Arg His Pro Phe Asn Asn Phe Gly Ile Trp Phe Ala Tyr Trp Gly
            100                 105                 110

Gln Gly Thr Leu Val Thr Val Ser Ser
        115                 120

<210> SEQ ID NO 91
<211> LENGTH: 13
<212> TYPE: PRT
<213> ORGANISM: Mus musculus

<400> SEQUENCE: 91

Glu Arg Ser Ser Gly Asp Ile Gly Asp Ser Tyr Val Ser
1               5                   10

<210> SEQ ID NO 92
<211> LENGTH: 7
<212> TYPE: PRT
<213> ORGANISM: Mus musculus
```

<400> SEQUENCE: 92

Ala Asp Asp Gln Arg Pro Ser
1               5

<210> SEQ ID NO 93
<211> LENGTH: 12
<212> TYPE: PRT
<213> ORGANISM: Mus musculus

<400> SEQUENCE: 93

Gln Ser Tyr Asp Ser Asn Ile Asp Phe Asn Pro Val
1               5                   10

<210> SEQ ID NO 94
<211> LENGTH: 5
<212> TYPE: PRT
<213> ORGANISM: Mus musculus

<400> SEQUENCE: 94

Lys Tyr Val Met Ala
1               5

<210> SEQ ID NO 95
<211> LENGTH: 17
<212> TYPE: PRT
<213> ORGANISM: Mus musculus

<400> SEQUENCE: 95

Ser Ile Asn Tyr Asp Gly Ser Thr Thr Tyr Tyr Arg Asp Ser Val Gln
1               5                   10                  15

Gly

<210> SEQ ID NO 96
<211> LENGTH: 12
<212> TYPE: PRT
<213> ORGANISM: Mus musculus

<400> SEQUENCE: 96

His Pro Phe Asn Asn Phe Gly Ile Trp Phe Ala Tyr
1               5                   10

<210> SEQ ID NO 97
<211> LENGTH: 321
<212> TYPE: DNA
<213> ORGANISM: Mus musculus

<400> SEQUENCE: 97
gatgtccgga tgacacagtc tccagcttcc ctgtctgcat ctctgggaga aactgtcaac      60
atcgaatgtc tagcaagtga ggacatttac agtgatttag catggtatca gcagaagcca    120
gggaaatctc ctcagctcct gatctataat gcaaatagtc tacaaaatgg ggtcccttca    180
cggtttagtg gcagtggttc tggcacgcag tattctctaa aaatatccac cctgcaatct    240
gaagatgtcg cgacttattt ctgtcaacaa tatagcaatt atcgtcggac gttcggtgga    300
ggcaccaagc tggaaatcaa t                                              321

<210> SEQ ID NO 98
<211> LENGTH: 381
<212> TYPE: DNA
<213> ORGANISM: Mus musculus

```
<400> SEQUENCE: 98
gaggtgcaac tggtggagtc tgggggaggc ctagtgcagc ctggaaggtc tctgaaacta    60
tcctgtgtag cctctggatt cacattcaac aaccactgga tgacctggat ccgccaggct   120
ccagggaagg ggctggagtg ggttgcatcc attactgata atggtggtag cacttactat   180
ccagactctg tgaagggccg attcactatc tccagagata tgcaaaaag caccctatac    240 ctgcacatga acagtctgag gtctgaggac acggccactt attactgtac aagagatcgg   300
tatgactctg atggttatta ttacgtgagg tactatgttg tggacgcctg gggtcaagga   360
gcttcagtca ctgtctcctc a                                              381

<210> SEQ ID NO 99
<211> LENGTH: 33
<212> TYPE: DNA
<213> ORGANISM: Mus musculus

<400> SEQUENCE: 99
ctagcaagtg aggacattta cagtgattta gca                                 33

<210> SEQ ID NO 100
<211> LENGTH: 21
<212> TYPE: DNA
<213> ORGANISM: Mus musculus

<400> SEQUENCE: 100
aatgcaaata gtctacaaaa t                                              21

<210> SEQ ID NO 101
<211> LENGTH: 27
<212> TYPE: DNA
<213> ORGANISM: Mus musculus

<400> SEQUENCE: 101
caacaatata gcaattatcg tcggacg                                        27

<210> SEQ ID NO 102
<211> LENGTH: 15
<212> TYPE: DNA
<213> ORGANISM: Mus musculus

<400> SEQUENCE: 102
aaccactgga tgacc                                                     15

<210> SEQ ID NO 103
<211> LENGTH: 51
<212> TYPE: DNA
<213> ORGANISM: Mus musculus

<400> SEQUENCE: 103
tccattactg ataatggtgg tagcacttac tatccagact ctgtgaaggg c              51

<210> SEQ ID NO 104
<211> LENGTH: 54
<212> TYPE: DNA
<213> ORGANISM: Mus musculus

<400> SEQUENCE: 104
gatcggtatg actctgatgg ttattattac gtgaggtact atgttgtgga cgcc           54
```

-continued

```
<210> SEQ ID NO 105
<211> LENGTH: 107
<212> TYPE: PRT
<213> ORGANISM: Mus musculus

<400> SEQUENCE: 105
```

Asp Val Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Tyr Ser Asp
                20                  25                  30

Leu Ala Trp Tyr Gln Gln Lys Pro Gly Lys Ser Pro Gln Leu Leu Ile
            35                  40                  45

Tyr Asn Ala Asn Ser Leu Gln Asn Gly Val Pro Ser Arg Phe Ser Gly
    50                  55                  60

Ser Gly Ser Gly Thr Gln Tyr Ser Leu Lys Ile Ser Thr Leu Gln Ser
65                  70                  75                  80

Glu Asp Val Ala Thr Tyr Phe Cys Gln Gln Tyr Ser Asn Tyr Arg Arg
                85                  90                  95

Thr Phe Gly Gly Gly Thr Lys Leu Glu Ile Asn
            100                 105

```
<210> SEQ ID NO 106
<211> LENGTH: 127
<212> TYPE: PRT
<213> ORGANISM: Mus musculus

<400> SEQUENCE: 106
```

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn His
                20                  25                  30

Trp Met Thr Trp Ile Arg Gln Ala Pro Gly Lys Gly Leu Glu Trp Val
            35                  40                  45

Ala Ser Ile Thr Asp Asn Gly Gly Ser Thr Tyr Tyr Pro Asp Ser Val
    50                  55                  60

Lys Gly Arg Phe Thr Ile Ser Arg Asp Asn Ala Lys Ser Thr Leu Tyr
65                  70                  75                  80

Leu His Met Asn Ser Leu Arg Ser Glu Asp Thr Ala Thr Tyr Tyr Cys
                85                  90                  95

Thr Arg Asp Arg Tyr Asp Ser Asp Gly Tyr Tyr Val Arg Tyr Tyr
            100                 105                 110

Val Val Asp Ala Trp Gly Gln Gly Ala Ser Val Thr Val Ser Ser
        115                 120                 125

```
<210> SEQ ID NO 107
<211> LENGTH: 11
<212> TYPE: PRT
<213> ORGANISM: Mus musculus

<400> SEQUENCE: 107
```

Leu Ala Ser Glu Asp Ile Tyr Ser Asp Leu Ala
1               5                   10

```
<210> SEQ ID NO 108
<211> LENGTH: 7
<212> TYPE: PRT
<213> ORGANISM: Mus musculus
```

<400> SEQUENCE: 108

Asn Ala Asn Ser Leu Gln Asn
1               5

<210> SEQ ID NO 109
<211> LENGTH: 9
<212> TYPE: PRT
<213> ORGANISM: Mus musculus

<400> SEQUENCE: 109

Gln Gln Tyr Ser Asn Tyr Arg Arg Thr
1               5

<210> SEQ ID NO 110
<211> LENGTH: 5
<212> TYPE: PRT
<213> ORGANISM: Mus musculus

<400> SEQUENCE: 110

Asn His Trp Met Thr
1               5

<210> SEQ ID NO 111
<211> LENGTH: 17
<212> TYPE: PRT
<213> ORGANISM: Mus musculus

<400> SEQUENCE: 111

Ser Ile Thr Asp Asn Gly Gly Ser Thr Tyr Tyr Pro Asp Ser Val Lys
1               5                   10                  15

Gly

<210> SEQ ID NO 112
<211> LENGTH: 18
<212> TYPE: PRT
<213> ORGANISM: Mus musculus

<400> SEQUENCE: 112

Asp Arg Tyr Asp Ser Asp Gly Tyr Tyr Tyr Val Arg Tyr Tyr Val Val
1               5                   10                  15

Asp Ala

<210> SEQ ID NO 113
<211> LENGTH: 336
<212> TYPE: DNA
<213> ORGANISM: Mus musculus

<400> SEQUENCE: 113
gatgttgtgt tgacacagac tccaggttcc ctgtctgtca cacttggaca gcaagtttct      60
atatcctgta ggtctagtca gagcctggaa agtcgtgatg gaacactta tttggaatgg     120 tacctacaga agccaggcca gtctccacag gtcctcctct atggagtttc caaccgattg     180
tctggggtcc cagacaggtt ccttggcaga gggtcagggg cagatttcac cctcaagatc     240
agcagagtag agcctgagga cttgggagtt tattactgct tccaagctac acatggtcca     300
ttcacgttcg gctcagggac gaagttggaa atgaaa                              336

<210> SEQ ID NO 114
<211> LENGTH: 354
<212> TYPE: DNA
<213> ORGANISM: Mus musculus

<400> SEQUENCE: 114

| caggtgcagc tgaaggagtc aggacctggc ctggtgcagc cctcacagac cctgtctctc | 60 |
| acctgcactg tctctgggtt ctcattaacc acctatcatg tgcactgggt tcgacagcct | 120 |
| ccaggaaaag gtctggagtg gatgggaata atgtggagag atggagacac atcatataat | 180 |
| tcagttctca aatctcgact gagcatcagc aggacatct ccaagagcca agttttctta | 240 |
| aaaatgagca gtctgcaaac tgaagacaca gccacttact tctgtgccag agggggact | 300 |
| cttacaactc cctttactta ctggggccaa ggcactctgg tcactgtctc ttca | 354 |

<210> SEQ ID NO 115
<211> LENGTH: 48
<212> TYPE: DNA
<213> ORGANISM: Mus musculus

<400> SEQUENCE: 115

| aggtctagtc agagcctgga aagtcgtgat gggaacactt atttggaa | 48 |

<210> SEQ ID NO 116
<211> LENGTH: 21
<212> TYPE: DNA
<213> ORGANISM: Mus musculus

<400> SEQUENCE: 116

| ggagtttcca accgattgtc t | 21 |

<210> SEQ ID NO 117
<211> LENGTH: 27
<212> TYPE: DNA
<213> ORGANISM: Mus musculus

<400> SEQUENCE: 117

| ttccaagcta cacatggtcc attcacg | 27 |

<210> SEQ ID NO 118
<211> LENGTH: 15
<212> TYPE: DNA
<213> ORGANISM: Mus musculus

<400> SEQUENCE: 118

| acctatcatg tgcac | 15 |

<210> SEQ ID NO 119
<211> LENGTH: 48
<212> TYPE: DNA
<213> ORGANISM: Mus musculus

<400> SEQUENCE: 119

| ataatgtgga gagatggaga cacatcatat aattcagttc tcaaatct | 48 |

<210> SEQ ID NO 120
<211> LENGTH: 30
<212> TYPE: DNA
<213> ORGANISM: Mus musculus

<400> SEQUENCE: 120

| gggggggactc ttacaactcc ctttacttac | 30 |

<210> SEQ ID NO 121
<211> LENGTH: 112
<212> TYPE: PRT
<213> ORGANISM: Mus musculus

<400> SEQUENCE: 121

Asp Val Val Leu Thr Gln Thr Pro Gly Ser Leu Ser Val Thr Leu Gly
1               5                   10                  15

Gln Gln Val Ser Ile Ser Cys Arg Ser Ser Gln Ser Leu Glu Ser Arg
            20                  25                  30

Asp Gly Asn Thr Tyr Leu Glu Trp Tyr Leu Gln Lys Pro Gly Gln Ser
        35                  40                  45

Pro Gln Val Leu Leu Tyr Gly Val Ser Asn Arg Leu Ser Gly Val Pro
    50                  55                  60

Asp Arg Phe Leu Gly Arg Gly Ser Gly Ala Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Gly Pro Phe Thr Phe Gly Ser Gly Thr Lys Leu Glu Met Lys
            100                 105                 110

<210> SEQ ID NO 122
<211> LENGTH: 118
<212> TYPE: PRT
<213> ORGANISM: Mus musculus

<400> SEQUENCE: 122

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Thr Tyr
            20                  25                  30

His Val His Trp Val Arg Gln Pro Pro Gly Lys Gly Leu Glu Trp Met
        35                  40                  45

Gly Ile Met Trp Arg Asp Gly Asp Thr Ser Tyr Asn Ser Val Leu Lys
    50                  55                  60

Ser Arg Leu Ser Ile Ser Arg Asp Ile Ser Lys Ser Gln Val Phe Leu
65                  70                  75                  80

Lys Met Ser Ser Leu Gln Thr Glu Asp Thr Ala Thr Tyr Phe Cys Ala
                85                  90                  95

Arg Gly Gly Thr Leu Thr Thr Pro Phe Thr Tyr Trp Gly Gln Gly Thr
            100                 105                 110

Leu Val Thr Val Ser Ser
        115

<210> SEQ ID NO 123
<211> LENGTH: 16
<212> TYPE: PRT
<213> ORGANISM: Mus musculus

<400> SEQUENCE: 123

Arg Ser Ser Gln Ser Leu Glu Arg Asp Gly Asn Thr Tyr Leu Glu
1               5                   10                  15

<210> SEQ ID NO 124
<211> LENGTH: 7
<212> TYPE: PRT
<213> ORGANISM: Mus musculus

<400> SEQUENCE: 124

Gly Val Ser Asn Arg Leu Ser
1               5

-continued

<210> SEQ ID NO 125
<211> LENGTH: 9
<212> TYPE: PRT
<213> ORGANISM: Mus musculus

<400> SEQUENCE: 125

Phe Gln Ala Thr His Gly Pro Phe Thr
1               5

<210> SEQ ID NO 126
<211> LENGTH: 5
<212> TYPE: PRT
<213> ORGANISM: Mus musculus

<400> SEQUENCE: 126

Thr Tyr His Val His
1               5

<210> SEQ ID NO 127
<211> LENGTH: 16
<212> TYPE: PRT
<213> ORGANISM: Mus musculus

<400> SEQUENCE: 127

Ile Met Trp Arg Asp Gly Asp Thr Ser Tyr Asn Ser Val Leu Lys Ser
1               5                   10                  15

<210> SEQ ID NO 128
<211> LENGTH: 10
<212> TYPE: PRT
<213> ORGANISM: Mus musculus

<400> SEQUENCE: 128

Gly Gly Thr Leu Thr Thr Pro Phe Thr Tyr
1               5                   10

<210> SEQ ID NO 129
<211> LENGTH: 321
<212> TYPE: DNA
<213> ORGANISM: Mus musculus

<400> SEQUENCE: 129
gatatccgga tgacacagtc tccagcttcc ctgtctgcat ctctgggaga aactgtcaac      60
atcgaatgtc tagcaagtga ggacatttac agtgatttag catggtatca gcagaagcca     120
gggaaatctc cacaactcct gatctataat gcaaatagcg tgcaaaatgg ggtcccttca     180
cggtttagtg gcagtggatc tggcacacag tattctctaa aaataaacag cctgcaatct     240
gaagatgtcg cgacttattt ctgtcaacag tttaacagtt atccgaacac gtttggagct     300
gggaccaagc tggaaatcaa a                                                321

<210> SEQ ID NO 130
<211> LENGTH: 363
<212> TYPE: DNA
<213> ORGANISM: Mus musculus

<400> SEQUENCE: 130
gaggtgcaac ttcaggagtc aggacctggc cttgtgaaac cctcacagtc actctccctc      60
acctgttctg tctctggttt ctccatcact aataattact ggggctggat ccggaagttc     120
ccaagaaata aaatggagtg gattggacac ataagctaca gtggtagcac taactacaac     180
ccatctctca aaagtcgcat ctccattact agagactcat cgaagagtca gttcttcctg     240

```
cagttgaact ctttaactac tgaggacaca gccacatatt actgtgcaag aggatcttat      300
tactatagcg catcgggcta ctttgattat tggggccaag gaatcacggt cacagtctcc      360
tca                                                                    363
```

<210> SEQ ID NO 131
<211> LENGTH: 33
<212> TYPE: DNA
<213> ORGANISM: Mus musculus

<400> SEQUENCE: 131

```
ctagcaagtg aggacattta cagtgattta gca                                    33
```

<210> SEQ ID NO 132
<211> LENGTH: 21
<212> TYPE: DNA
<213> ORGANISM: Mus musculus

<400> SEQUENCE: 132

```
aatgcaaata gcgtgcaaaa t                                                 21
```

<210> SEQ ID NO 133
<211> LENGTH: 27
<212> TYPE: DNA
<213> ORGANISM: Mus musculus

<400> SEQUENCE: 133

```
caacagttta acagttatcc gaacacg                                           27
```

<210> SEQ ID NO 134
<211> LENGTH: 15
<212> TYPE: DNA
<213> ORGANISM: Mus musculus

<400> SEQUENCE: 134

```
aataattact ggggc                                                        15
```

<210> SEQ ID NO 135
<211> LENGTH: 48
<212> TYPE: DNA
<213> ORGANISM: Mus musculus

<400> SEQUENCE: 135

```
cacataagct acagtggtag cactaactac aacccatctc tcaaaagt                    48
```

<210> SEQ ID NO 136
<211> LENGTH: 39
<212> TYPE: DNA
<213> ORGANISM: Mus musculus

<400> SEQUENCE: 136

```
ggatcttatt actatagcgc atcgggctac tttgattat                              39
```

<210> SEQ ID NO 137
<211> LENGTH: 107
<212> TYPE: PRT
<213> ORGANISM: Mus musculus

<400> SEQUENCE: 137

```
Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Tyr Ser Asp
            20                  25                  30
```

```
Leu Ala Trp Tyr Gln Gln Lys Pro Gly Lys Ser Pro Gln Leu Leu Ile
            35                  40                  45

Tyr Asn Ala Asn Ser Val Gln Asn Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Phe Asn Ser Tyr Pro Asn
                85                  90                  95

Thr Phe Gly Ala Gly Thr Lys Leu Glu Ile Lys
                100                 105
```

<210> SEQ ID NO 138
<211> LENGTH: 121
<212> TYPE: PRT
<213> ORGANISM: Mus musculus

<400> SEQUENCE: 138

```
Glu Val Gln Leu Gln Glu Ser Gly Pro Gly Leu Val Lys Pro Ser Gln
1               5                   10                  15

Ser Leu Ser Leu Thr Cys Ser Val Ser Gly Phe Ser Ile Thr Asn Asn
            20                  25                  30

Tyr Trp Gly Trp Ile Arg Lys Phe Pro Arg Asn Lys Met Glu Trp Ile
            35                  40                  45

Gly His Ile Ser Tyr Ser Gly Ser Thr Asn Tyr Asn Pro Ser Leu Lys
        50                  55                  60

Ser Arg Ile Ser Ile Thr Arg Asp Ser Ser Lys Ser Gln Phe Phe Leu
65                  70                  75                  80

Gln Leu Asn Ser Leu Thr Thr Glu Asp Thr Ala Thr Tyr Tyr Cys Ala
                85                  90                  95

Arg Gly Ser Tyr Tyr Tyr Ser Ala Ser Gly Tyr Phe Asp Tyr Trp Gly
                100                 105                 110

Gln Gly Ile Thr Val Thr Val Ser Ser
            115                 120
```

<210> SEQ ID NO 139
<211> LENGTH: 11
<212> TYPE: PRT
<213> ORGANISM: Mus musculus

<400> SEQUENCE: 139

```
Leu Ala Ser Glu Asp Ile Tyr Ser Asp Leu Ala
1               5                   10
```

<210> SEQ ID NO 140
<211> LENGTH: 7
<212> TYPE: PRT
<213> ORGANISM: Mus musculus

<400> SEQUENCE: 140

```
Asn Ala Asn Ser Val Gln Asn
1               5
```

<210> SEQ ID NO 141
<211> LENGTH: 9
<212> TYPE: PRT
<213> ORGANISM: Mus musculus

<400> SEQUENCE: 141

```
Gln Gln Phe Asn Ser Tyr Pro Asn Thr
1               5
```

<210> SEQ ID NO 142
<211> LENGTH: 5
<212> TYPE: PRT
<213> ORGANISM: Mus musculus

<400> SEQUENCE: 142

Asn Asn Tyr Trp Gly
1               5

<210> SEQ ID NO 143
<211> LENGTH: 16
<212> TYPE: PRT
<213> ORGANISM: Mus musculus

<400> SEQUENCE: 143

His Ile Ser Tyr Ser Gly Ser Thr Asn Tyr Asn Pro Ser Leu Lys Ser
1               5                   10                  15

<210> SEQ ID NO 144
<211> LENGTH: 13
<212> TYPE: PRT
<213> ORGANISM: Mus musculus

<400> SEQUENCE: 144

Gly Ser Tyr Tyr Tyr Ser Ala Ser Gly Tyr Phe Asp Tyr
1               5                   10

<210> SEQ ID NO 145
<211> LENGTH: 336
<212> TYPE: DNA
<213> ORGANISM: Mus musculus

<400> SEQUENCE: 145
gacgtggtct tgacccaaac ccctggatca cttagcgtga cactgggcga tccagcatca      60
atgtcctgca gaagctccca gtccttggag agtagcgacg gcaacacata cctcgagtgg     120
tatctgcaga atccgggca gtccccacag ctgctgatct acggcgtgag taacaggttc     180
agcggggtgc ctgataggtt cgccggcagc gggtccggga cagattttac tctcaagatt    240
agccgcgtcg aacccgagga cctgggcgtg tactactgtt ttcaggccac tcgggacccc    300
tttactttcg ggagcgggac aaagctggag attaat                               336

<210> SEQ ID NO 146
<211> LENGTH: 354
<212> TYPE: DNA
<213> ORGANISM: Mus musculus

<400> SEQUENCE: 146
caggtccagc ttaaagagtc cggacctgga cttgtgcagc catcccagac cttgtccttg      60
acctgcaccg tgtcagggtt ctctctcacc agttaccacc tgcattggat caggcagcct    120
cccggcaagg ggctggaatg gatggggctg atgtggagag atgggatac atcttacaac      180 agcaggctga gagccggct gagcattaca cgggacacca gcaagtccca ggtgttcctc      240
aagatgagcg ggctccaaac tgaggacaca gctacatact actgtgcacg cggcatgaca    300
ctcgccactc cctttctgta ttggggccag ggcactctgg tcactgtgtc ctca            354

<210> SEQ ID NO 147
<211> LENGTH: 48
<212> TYPE: DNA
<213> ORGANISM: Mus musculus

<400> SEQUENCE: 147
agaagctccc agtccttgga gagtagcgac ggcaacacat acctcgag                48

<210> SEQ ID NO 148
<211> LENGTH: 21
<212> TYPE: DNA
<213> ORGANISM: Mus musculus

<400> SEQUENCE: 148
ggcgtgagta acaggttcag c                                             21

<210> SEQ ID NO 149
<211> LENGTH: 27
<212> TYPE: DNA
<213> ORGANISM: Mus musculus

<400> SEQUENCE: 149
tttcaggcca ctcgggaccc ctttact                                       27

<210> SEQ ID NO 150
<211> LENGTH: 15
<212> TYPE: DNA
<213> ORGANISM: Mus musculus

<400> SEQUENCE: 150
agttaccacc tgcat                                                    15

<210> SEQ ID NO 151
<211> LENGTH: 48
<212> TYPE: DNA
<213> ORGANISM: Mus musculus

<400> SEQUENCE: 151
ctgatgtgga gagatgggga tacatcttac aacagcaggc tgaagagc                48

<210> SEQ ID NO 152
<211> LENGTH: 30
<212> TYPE: DNA
<213> ORGANISM: Mus musculus

<400> SEQUENCE: 152
ggcatgacac tcgccactcc ctttctgtat                                    30

<210> SEQ ID NO 153
<211> LENGTH: 112
<212> TYPE: PRT
<213> ORGANISM: Mus musculus

<400> SEQUENCE: 153

Asp Val Val Leu Thr Gln Thr Pro Gly Ser Leu Ser Val Thr Leu Gly
1               5                   10                  15

Asp Pro Ala Ser Met Ser Cys Arg Ser Ser Gln Ser Leu Glu Ser Ser
            20                  25                  30

Asp Gly Asn Thr Tyr Leu Glu Trp Tyr Leu Gln Lys Ser Gly Gln Ser
        35                  40                  45

Pro Gln Leu Leu Ile Tyr Gly Val Ser Asn Arg Phe Ser Gly Val Pro
    50                  55                  60

Asp Arg Phe Ala Gly Ser Gly Ser Gly Thr Asp Phe Thr Leu Lys Ile
65                  70                  75                  80

-continued

Ser Arg Val Glu Pro Glu Asp Leu Gly Val Tyr Tyr Cys Phe Gln Ala
            85                  90                  95

Thr Arg Asp Pro Phe Thr Phe Gly Ser Gly Thr Lys Leu Glu Ile Asn
            100                 105                 110

<210> SEQ ID NO 154
<211> LENGTH: 118
<212> TYPE: PRT
<213> ORGANISM: Mus musculus

<400> SEQUENCE: 154

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Leu His Trp Ile Arg Gln Pro Pro Gly Lys Gly Leu Glu Trp Met
        35                  40                  45

Gly Leu Met Trp Arg Asp Gly Asp Thr Ser Tyr Asn Ser Arg Leu Lys
    50                  55                  60

Ser Arg Leu Ser Ile Thr Arg Asp Thr Ser Lys Ser Gln Val Phe Leu
65                  70                  75                  80

Lys Met Ser Gly Leu Gln Thr Glu Asp Thr Ala Thr Tyr Tyr Cys Ala
                85                  90                  95

Arg Gly Met Thr Leu Ala Thr Pro Phe Leu Tyr Trp Gly Gln Gly Thr
            100                 105                 110

Leu Val Thr Val Ser Ser
        115

<210> SEQ ID NO 155
<211> LENGTH: 16
<212> TYPE: PRT
<213> ORGANISM: Mus musculus

<400> SEQUENCE: 155

Arg Ser Ser Gln Ser Leu Glu Ser Ser Asp Gly Asn Thr Tyr Leu Glu
1               5                   10                  15

<210> SEQ ID NO 156
<211> LENGTH: 7
<212> TYPE: PRT
<213> ORGANISM: Mus musculus

<400> SEQUENCE: 156

Gly Val Ser Asn Arg Phe Ser
1               5

<210> SEQ ID NO 157
<211> LENGTH: 9
<212> TYPE: PRT
<213> ORGANISM: Mus musculus

<400> SEQUENCE: 157

Phe Gln Ala Thr Arg Asp Pro Phe Thr
1               5

<210> SEQ ID NO 158
<211> LENGTH: 5
<212> TYPE: PRT
<213> ORGANISM: Mus musculus

<400> SEQUENCE: 158

Ser Tyr His Leu His
1               5

<210> SEQ ID NO 159
<211> LENGTH: 16
<212> TYPE: PRT
<213> ORGANISM: Mus musculus

<400> SEQUENCE: 159

Leu Met Trp Arg Asp Gly Asp Thr Ser Tyr Asn Ser Arg Leu Lys Ser
1               5                   10                  15

<210> SEQ ID NO 160
<211> LENGTH: 10
<212> TYPE: PRT
<213> ORGANISM: Mus musculus

<400> SEQUENCE: 160

Gly Met Thr Leu Ala Thr Pro Phe Leu Tyr
1               5                   10

<210> SEQ ID NO 161
<211> LENGTH: 321
<212> TYPE: DNA
<213> ORGANISM: Mus musculus

<400> SEQUENCE: 161
gatatccgga tgacacagtc gccagcttcc ctgtctgcat ctctgggaga aactgtcaac      60
atcgaatgtc tagcaagtga ggacattcac agtgatttag catggtatca gcagaagcca     120
gggaaatctc ctcagctcct gatctataat gcaaatagct tgcaaaatgg ggtcccttca     180
cggttcagtg gcagtggatc tggcacacag tattctctaa aaataaccag cctgcaatct     240
gaagatgtcg cgacttattt ctgtcaacaa tataccaact atccgaacac gtttggagcg     300
gggaccaagc tggaaatcaa t                                               321

<210> SEQ ID NO 162
<211> LENGTH: 363
<212> TYPE: DNA
<213> ORGANISM: Mus musculus

<400> SEQUENCE: 162
gaggtgcagc ttcaggagtc aggacctggc cttgtgaaac cctcacagtc actctccctc      60
acctgttctg tcactggtta ctccatcact aatcattact ggggctggat ccggaaattc     120
ccaggaaata aaatggagtg gattggacac ataagcaaca gtggtggcac taactacaac     180
ccatcactca aaagtcgaat ctccattact agagacacat cgaagaatca gttcttcctg     240
cagttgaagt ctgtaactac tgaggacaca gccacatatt actgtacaag aggatcttat     300
tactatagcg catcgggcta ctttgattac tggggccaag gagtcctggt cacagtctcc     360
tcc                                                                  363

<210> SEQ ID NO 163
<211> LENGTH: 33
<212> TYPE: DNA
<213> ORGANISM: Mus musculus

<400> SEQUENCE: 163
ctagcaagtg aggacattca cagtgattta gca                                   33

<210> SEQ ID NO 164
<211> LENGTH: 21
<212> TYPE: DNA
<213> ORGANISM: Mus musculus

<400> SEQUENCE: 164
aatgcaaata gcttgcaaaa t                                          21

<210> SEQ ID NO 165
<211> LENGTH: 27
<212> TYPE: DNA
<213> ORGANISM: Mus musculus

<400> SEQUENCE: 165
caacaatata ccaactatcc gaacacg                                    27

<210> SEQ ID NO 166
<211> LENGTH: 15
<212> TYPE: DNA
<213> ORGANISM: Mus musculus

<400> SEQUENCE: 166
aatcattact ggggc                                                 15

<210> SEQ ID NO 167
<211> LENGTH: 48
<212> TYPE: DNA
<213> ORGANISM: Mus musculus

<400> SEQUENCE: 167
cacataagca acagtggtgg cactaactac aacccatcac tcaaaagt             48

<210> SEQ ID NO 168
<211> LENGTH: 39
<212> TYPE: DNA
<213> ORGANISM: Mus musculus

<400> SEQUENCE: 168
ggatcttatt actatagcgc atcgggctac tttgattac                       39

<210> SEQ ID NO 169
<211> LENGTH: 107
<212> TYPE: PRT
<213> ORGANISM: Mus musculus

<400> SEQUENCE: 169

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile His Ser Asp
            20                  25                  30

Leu Ala Trp Tyr Gln Gln Lys Pro Gly Lys Ser Pro Gln Leu Leu Ile
        35                  40                  45

Tyr Asn Ala Asn Ser Leu Gln Asn Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Val Ala Thr Tyr Phe Cys Gln Gln Tyr Thr Asn Tyr Pro Asn
                85                  90                  95

Thr Phe Gly Ala Gly Thr Lys Leu Glu Ile Asn
            100                 105

```
<210> SEQ ID NO 170
<211> LENGTH: 121
<212> TYPE: PRT
<213> ORGANISM: Mus musculus

<400> SEQUENCE: 170

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Asn His
            20                  25                  30

Tyr Trp Gly Trp Ile Arg Lys Phe Pro Gly Asn Lys Met Glu Trp Ile
        35                  40                  45

Gly His Ile Ser Asn Ser Gly Gly Thr Asn Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Lys Ser Val Thr Thr Glu Asp Thr Ala Thr Tyr Tyr Cys Thr
                85                  90                  95

Arg Gly Ser Tyr Tyr Tyr Ser Ala Ser Gly Tyr Phe Asp Tyr Trp Gly
            100                 105                 110

Gln Gly Val Leu Val Thr Val Ser Ser
        115                 120

<210> SEQ ID NO 171
<211> LENGTH: 11
<212> TYPE: PRT
<213> ORGANISM: Mus musculus

<400> SEQUENCE: 171

Leu Ala Ser Glu Asp Ile His Ser Asp Leu Ala
1               5                   10

<210> SEQ ID NO 172
<211> LENGTH: 7
<212> TYPE: PRT
<213> ORGANISM: Mus musculus

<400> SEQUENCE: 172

Asn Ala Asn Ser Leu Gln Asn
1               5

<210> SEQ ID NO 173
<211> LENGTH: 9
<212> TYPE: PRT
<213> ORGANISM: Mus musculus

<400> SEQUENCE: 173

Gln Gln Tyr Thr Asn Tyr Pro Asn Thr
1               5

<210> SEQ ID NO 174
<211> LENGTH: 5
<212> TYPE: PRT
<213> ORGANISM: Mus musculus

<400> SEQUENCE: 174

Asn His Tyr Trp Gly
1               5
```

<210> SEQ ID NO 175
<211> LENGTH: 16
<212> TYPE: PRT
<213> ORGANISM: Mus musculus

<400> SEQUENCE: 175

His Ile Ser Asn Ser Gly Gly Thr Asn Tyr Asn Pro Ser Leu Lys Ser
1               5                   10                  15

<210> SEQ ID NO 176
<211> LENGTH: 13
<212> TYPE: PRT
<213> ORGANISM: Mus musculus

<400> SEQUENCE: 176

Gly Ser Tyr Tyr Tyr Ser Ala Ser Gly Tyr Phe Asp Tyr
1               5                   10

<210> SEQ ID NO 177
<211> LENGTH: 321
<212> TYPE: DNA
<213> ORGANISM: Mus musculus

<400> SEQUENCE: 177
gatatccgga tgacacagtc tccagcttcc ctgtctgcat ctctgggaga aactgtcaac      60
atcggatgtc tagcaagtga ggacatttac agtgatttag catggtatca gcagaagcca     120
gggaagtctc ctcagctcct gatctataat gcaaataact tgcaaaatgg ggtcccttca     180
cggtttagtg gcagtggatc tggcacacaa tattctctaa aaataaacag cctgcaatct     240
gaagatgtcg cgacttattt ctgtcaacaa tataacagtt atccgaacac gtttggagct     300
gggaccaagc tggaaataaa a                                                321

<210> SEQ ID NO 178
<211> LENGTH: 363
<212> TYPE: DNA
<213> ORGANISM: Mus musculus

<400> SEQUENCE: 178
gaggtgcagc ttcaggagtc aggacctggc cttgtgaaac cctcacagtc actctccctc      60
atttgttctg tcactggtta ctccatcact acaacttact ggggctggat ccggaagttc     120
ccaggaaata aaatggagtg gattggacac ataagtaaca gtggtagtac taattacaac     180
ccatctctca aaagtcgaat ctccgttact agagacacat cgacgaatca gttcttcctg     240
cagttgaact ctgtaactac tgaggacaca gccacatatt actgtgcaag aggatcttat     300
tactatagcg cgtcgggcta ctttgattac tggggccacg gagtcatggt cacagtctcc     360
tca                                                                    363

<210> SEQ ID NO 179
<211> LENGTH: 33
<212> TYPE: DNA
<213> ORGANISM: Mus musculus

<400> SEQUENCE: 179
ctagcaagtg aggacattta cagtgattta gca                                   33

<210> SEQ ID NO 180
<211> LENGTH: 21
<212> TYPE: DNA
<213> ORGANISM: Mus musculus -continued

<400> SEQUENCE: 180
aatgcaaata acttgcaaaa t                                         21

<210> SEQ ID NO 181
<211> LENGTH: 27
<212> TYPE: DNA
<213> ORGANISM: Mus musculus

<400> SEQUENCE: 181
caacaatata acagttatcc gaacacg                                   27

<210> SEQ ID NO 182
<211> LENGTH: 15
<212> TYPE: DNA
<213> ORGANISM: Mus musculus

<400> SEQUENCE: 182
acaacttact ggggc                                                15

<210> SEQ ID NO 183
<211> LENGTH: 48
<212> TYPE: DNA
<213> ORGANISM: Mus musculus

<400> SEQUENCE: 183
cacataagta acagtggtag tactaattac aacccatctc tcaaaagt             48

<210> SEQ ID NO 184
<211> LENGTH: 39
<212> TYPE: DNA
<213> ORGANISM: Mus musculus

<400> SEQUENCE: 184
ggatcttatt actatagcgc gtcgggctac tttgattac                       39

<210> SEQ ID NO 185
<211> LENGTH: 107
<212> TYPE: PRT
<213> ORGANISM: Mus musculus

<400> SEQUENCE: 185

Asp Ile Arg Met Thr Gln Ser Pro Ala Ser Leu Ser Ala Ser Leu Gly
1               5                   10                  15

Glu Thr Val Asn Ile Gly Cys Leu Ala Ser Glu Asp Ile Tyr Ser Asp
            20                  25                  30

Leu Ala Trp Tyr Gln Gln Lys Pro Gly Lys Ser Pro Gln Leu Leu Ile
        35                  40                  45

Tyr Asn Ala Asn Asn Leu Gln Asn Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Thr Tyr Phe Cys Gln Gln Tyr Asn Ser Tyr Pro Asn
                85                  90                  95

Thr Phe Gly Ala Gly Thr Lys Leu Glu Ile Lys
            100                 105

<210> SEQ ID NO 186
<211> LENGTH: 121
<212> TYPE: PRT
<213> ORGANISM: Mus musculus

<400> SEQUENCE: 186

Glu Val Gln Leu Gln Glu Ser Gly Pro Gly Leu Val Lys Pro Ser Gln
1               5                   10                  15

Ser Leu Ser Leu Ile Cys Ser Val Thr Gly Tyr Ser Ile Thr Thr Thr
            20                  25                  30

Tyr Trp Gly Trp Ile Arg Lys Phe Pro Gly Asn Lys Met Glu Trp Ile
        35                  40                  45

Gly His Ile Ser Asn Ser Gly Ser Thr Asn Tyr Asn Pro Ser Leu Lys
    50                  55                  60

Ser Arg Ile Ser Val Thr Arg Asp Thr Ser Thr Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Gly Ser Tyr Tyr Tyr Ser Ala Ser Gly Tyr Phe Asp Tyr Trp Gly
            100                 105                 110

His Gly Val Met Val Thr Val Ser Ser
        115                 120

<210> SEQ ID NO 187
<211> LENGTH: 11
<212> TYPE: PRT
<213> ORGANISM: Mus musculus

<400> SEQUENCE: 187

Leu Ala Ser Glu Asp Ile Tyr Ser Asp Leu Ala
1               5                   10

<210> SEQ ID NO 188
<211> LENGTH: 7
<212> TYPE: PRT
<213> ORGANISM: Mus musculus

<400> SEQUENCE: 188

Asn Ala Asn Asn Leu Gln Asn
1               5

<210> SEQ ID NO 189
<211> LENGTH: 9
<212> TYPE: PRT
<213> ORGANISM: Mus musculus

<400> SEQUENCE: 189

Gln Gln Tyr Asn Ser Tyr Pro Asn Thr
1               5

<210> SEQ ID NO 190
<211> LENGTH: 5
<212> TYPE: PRT
<213> ORGANISM: Mus musculus

<400> SEQUENCE: 190

Thr Thr Tyr Trp Gly
1               5

<210> SEQ ID NO 191
<211> LENGTH: 16
<212> TYPE: PRT
<213> ORGANISM: Mus musculus

<400> SEQUENCE: 191

His Ile Ser Asn Ser Gly Ser Thr Asn Tyr Asn Pro Ser Leu Lys Ser
1               5                   10                  15

<210> SEQ ID NO 192
<211> LENGTH: 13
<212> TYPE: PRT
<213> ORGANISM: Mus musculus

<400> SEQUENCE: 192

Gly Ser Tyr Tyr Tyr Ser Ala Ser Gly Tyr Phe Asp Tyr
1               5                   10

<210> SEQ ID NO 193
<211> LENGTH: 108
<212> TYPE: PRT
<213> ORGANISM: Mus musculus

<400> SEQUENCE: 193

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Leu Thr Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Lys Thr Pro Tyr
                85                  90                  95

Ser Phe Gly Gly Gly Thr Lys Leu Glu Arg Leu Arg
            100                 105

<210> SEQ ID NO 194
<211> LENGTH: 115
<212> TYPE: PRT
<213> ORGANISM: Mus musculus

<400> SEQUENCE: 194

Gln Val Gln Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Ile Tyr Trp Val Arg Gln Pro Pro Gly Lys Gly Leu Glu Trp Leu
        35                  40                  45

Gly Met Ile Trp Gly Asp Gly Arg Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Tyr Tyr Gly Ser Lys Asp Tyr Trp Gly Gln Gly Thr Thr Leu
            100                 105                 110

Thr Val Ser
        115

-continued

```
<210> SEQ ID NO 195
<211> LENGTH: 111
<212> TYPE: PRT
<213> ORGANISM: Mus musculus

<400> SEQUENCE: 195

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Gly Asp Pro Trp Thr Phe Gly Gly Gly Thr Lys Leu Glu Ile Lys
            100                 105                 110

<210> SEQ ID NO 196
<211> LENGTH: 123
<212> TYPE: PRT
<213> ORGANISM: Mus musculus

<400> SEQUENCE: 196

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Ala Ala Asp Thr Ala Thr Tyr Tyr
                85                  90                  95

Cys Ala Arg Lys Arg Ser Ser Val Val Ala His Tyr Tyr Ala Met Asp
            100                 105                 110

Tyr Trp Gly Gln Gly Thr Ser Val Thr Val Ser
        115                 120

<210> SEQ ID NO 197
<211> LENGTH: 113
<212> TYPE: PRT
<213> ORGANISM: Artificial
<220> FEATURE:
<223> OTHER INFORMATION: humanized antibody

<400> SEQUENCE: 197

Gln Phe Gln Leu Thr Gln Pro Ser Ser Val Ser Ala Ser Val Gly Asp
1               5                   10                  15

Arg Val Thr Ile Thr Cys Glu Arg Ser Ser Gly Asp Ile Gly Asp Ser
            20                  25                  30

Tyr Val Ser Trp Tyr Gln Gln Lys Pro Gly Gln Pro Pro Lys Asn Val
        35                  40                  45
```

```
Ile Tyr Ala Asp Asp Gln Arg Pro Ser Gly Val Pro Asp Arg Phe Ser
        50                  55                  60

Gly Ser Ile Asp Gly Ser Gly Asn Ser Ala Ser Leu Thr Ile Ser Ser
65                  70                  75                  80

Leu Gln Ala Glu Asp Ala Ala Asp Tyr Phe Cys Gln Ser Tyr Asp Ser
                85                  90                  95

Asn Ile Asp Phe Asn Pro Val Phe Gly Gly Gly Thr Lys Leu Glu Val
            100                 105                 110

Lys

<210> SEQ ID NO 198
<211> LENGTH: 120
<212> TYPE: PRT
<213> ORGANISM: Artificial
<220> FEATURE:
<223> OTHER INFORMATION: humanized antibody

<400> SEQUENCE: 198

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Lys Tyr
                20                  25                  30

Ala Met Ser Trp Val Arg Gln Ala Pro Gly Lys Gly Leu Glu Trp Val
            35                  40                  45

Ser Ala Ile Asn Tyr Asp Gly Ser Thr Thr Tyr Tyr Ala Asp Ser Val
        50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Phe Asn Asn Phe Gly Ile Trp Phe Ala Tyr Trp Gly
            100                 105                 110

Gln Gly Thr Leu Val Thr Val Ser
        115                 120

<210> SEQ ID NO 199
<211> LENGTH: 114
<212> TYPE: PRT
<213> ORGANISM: Artificial
<220> FEATURE:
<223> OTHER INFORMATION: humanized antibody

<400> SEQUENCE: 199

Asp Val Val Leu Thr Gln Thr Pro Leu Ser Leu Pro Val Thr Pro Gly
1               5                   10                  15

Glu Pro Ala Ser Ile Ser Cys Arg Ser Ser Gln Ser Leu Glu Ser Arg
                20                  25                  30

Asp Gly Asn Thr Tyr Leu Glu Trp Tyr Leu Gln Lys Pro Gly Gln Ser
            35                  40                  45

Pro Gln Val Leu Leu Tyr Gly Val Ser Asn Arg Leu Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95
```

Thr His Gly Pro Phe Thr Phe Gly Gln Gly Thr Lys Leu Glu Ile Lys
            100                 105                 110

Arg Thr

<210> SEQ ID NO 200
<211> LENGTH: 118
<212> TYPE: PRT
<213> ORGANISM: Artificial
<220> FEATURE:
<223> OTHER INFORMATION: humanized antibody

<400> SEQUENCE: 200

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

His Val His Trp Val Arg Gln Pro Pro Gly Lys Gly Leu Glu Trp Ile
        35                  40                  45

Gly Ile Met Trp Arg Asp Gly Asp Thr Tyr Tyr Asn Ser Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Gly Gly Thr Leu Thr Thr Pro Phe Thr Tyr Trp Gly Gln Gly Thr
            100                 105                 110

Leu Val Thr Val Ser Ser
        115

<210> SEQ ID NO 201
<211> LENGTH: 114
<212> TYPE: PRT
<213> ORGANISM: Artificial
<220> FEATURE:
<223> OTHER INFORMATION: humanized antibody

<400> SEQUENCE: 201

Asp Val Val Leu Thr Gln Thr Pro Leu Ser Leu Ser Val Thr Pro Gly
1               5                   10                  15

Gln Pro Ala Ser Ile Ser Cys Arg Ser Ser Gln Ser Leu Glu Ser Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Thr Arg Asp Pro Phe Thr Phe Gly Gln Gly Thr Lys Leu Glu Ile Lys
            100                 105                 110

Arg Thr

<210> SEQ ID NO 202
<211> LENGTH: 118
<212> TYPE: PRT
<213> ORGANISM: Artificial
<220> FEATURE:
<223> OTHER INFORMATION: humanized antibody

<400> SEQUENCE: 202

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Tyr
            20                  25                  30

His Leu His Trp Ile Arg Gln Pro Pro Gly Lys Ala Leu Glu Trp Met
        35                  40                  45

Gly Leu Met Trp Arg Asp Gly Asp Thr Ser Tyr Asn Ser Arg Leu Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Gly Met Thr Leu Ala Thr Pro Phe Leu Tyr Trp Gly Gln Gly Thr
            100                 105                 110

Leu Val Thr Val Ser Ser
        115

<210> SEQ ID NO 203
<211> LENGTH: 625
<212> TYPE: PRT
<213> ORGANISM: Homo sapiens

<400> SEQUENCE: 203

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

-continued

```
Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625

<210> SEQ ID NO 204
<211> LENGTH: 114
<212> TYPE: PRT
```

```
<213> ORGANISM: Artificial Sequence
<220> FEATURE:
<223> OTHER INFORMATION: optimized, humanized antibody

<400> SEQUENCE: 204

Asp Ile Val Met Thr Gln Thr Pro Leu Ser Leu Ser Val Thr Pro Gly
1               5                   10                  15

Gln Pro Ala Ser Ile Ser Cys Arg Ser Gln Ser Leu Glu Ser Ser
            20                  25                  30

Asp Gly Asn Thr Tyr Leu Glu Trp Tyr Leu Gln Lys Pro Gly Gln Ser
            35                  40                  45

Pro Gln Leu Leu Ile Tyr Gly Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr Arg Asp Pro Phe Thr Phe Gly Gln Gly Thr Lys Leu Glu Ile Lys
            100                 105                 110

Arg Thr

<210> SEQ ID NO 205
<211> LENGTH: 118
<212> TYPE: PRT
<213> ORGANISM: Artificial Sequence
<220> FEATURE:
<223> OTHER INFORMATION: optimized, humanized antibody

<400> SEQUENCE: 205

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Tyr
            20                  25                  30

Ser Val Ala Trp Ile Arg Gln Pro Pro Gly Lys Ala Leu Glu Trp Leu
            35                  40                  45

Ala Glu Ile Trp Arg Asp Gly Asp Thr Ser Tyr Asn Ser Arg Leu Lys
50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Gly Met Thr Leu Ala Thr Pro Phe Leu Tyr Trp Gly Gln Gly Thr
            100                 105                 110

Leu Val Thr Val Ser Ser
        115

<210> SEQ ID NO 206
<211> LENGTH: 114
<212> TYPE: PRT
<213> ORGANISM: artificial
<220> FEATURE:
<223> OTHER INFORMATION: optimized, humarized antibody

<400> SEQUENCE: 206

Asp Val Val Leu Thr Gln Thr Pro Leu Ser Leu Pro Val Thr Pro Gly
1               5                   10                  15

Glu Pro Ala Ser Ile Ser Cys Arg Ser Gln Ser Leu Glu Ser Arg
            20                  25                  30
```

```
Asp Gly Asn Thr Tyr Leu Glu Trp Tyr Leu Gln Lys Pro Gly Gln Ser
            35                  40                  45

Pro Gln Val Leu Leu Tyr Gly Val Ser Asn Arg Leu Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Thr His Gly Pro Phe Thr Phe Gly Gln Gly Thr Lys Leu Glu Ile Lys
                100                 105                 110

Arg Thr
```

```
<210> SEQ ID NO 207
<211> LENGTH: 118
<212> TYPE: PRT
<213> ORGANISM: Artificial Sequence
<220> FEATURE:
<223> OTHER INFORMATION: optimized, humanized antibody

<400> SEQUENCE: 207

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Ser Thr Tyr
             20                  25                  30

His Val His Trp Val Arg Gln Pro Pro Gly Lys Gly Leu Glu Trp Ile
             35                  40                  45

Gly Ile Met Trp Arg Asp Gly Asp Thr Tyr Tyr Asn Pro Lys Leu Lys
 50                  55                  60

Ser Arg Val Thr Ile Ser Val Asp Thr Ser Lys Asn Gln Val Ser Leu
 65                  70                  75                  80

Lys Leu Ser Ser Val Thr Ala Ala Asp Thr Ala Val Tyr Phe Cys Ala
                 85                  90                  95

Arg Gly Gly Thr Leu Thr Thr Pro Phe Thr Tyr Trp Gly Gln Gly Thr
                100                 105                 110

Leu Val Thr Val Ser Ser
            115
```

```
<210> SEQ ID NO 208
<211> LENGTH: 113
<212> TYPE: PRT
<213> ORGANISM: Artificial Sequence
<220> FEATURE:
<223> OTHER INFORMATION: optimized, humanized antibody

<400> SEQUENCE: 208

Gln Phe Gln Leu Thr Gln Pro Ser Ser Val Ser Ala Ser Val Gly Asp
 1               5                  10                  15

Arg Val Thr Ile Thr Cys Glu Arg Ser Ser Gly Asp Ile Gly Asp Ser
             20                  25                  30

Tyr Val Ser Trp Tyr Gln Gln Lys Pro Gly Gln Pro Pro Lys Asn Val
             35                  40                  45

Ile Tyr Ala Asp Asp Gln Arg Pro Ser Gly Val Pro Asp Arg Phe Ser
 50                  55                  60

Gly Ser Ile Asp Gly Ser Gly Asn Ser Ala Ser Leu Thr Ile Ser Ser
 65                  70                  75                  80

Leu Gln Ala Glu Asp Ala Ala Asp Tyr Phe Cys Gln Ser Tyr Asp Ser
                 85                  90                  95
```

```
Asn Ile Asp Phe Asn Pro Val Phe Gly Gly Thr Lys Leu Thr Val
            100                 105                 110

Leu

<210> SEQ ID NO 209
<211> LENGTH: 120
<212> TYPE: PRT
<213> ORGANISM: Artificial Sequence
<220> FEATURE:
<223> OTHER INFORMATION: optimized, humanized antibody

<400> SEQUENCE: 209

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Lys Tyr
            20                  25                  30

Ala Met Ser Trp Val Arg Gln Ala Pro Gly Lys Gly Leu Glu Trp Val
            35                  40                  45

Ser Ala Ile Asn Tyr Asp Gly Ser Thr Thr Tyr Tyr Ala Asp Ser Val
50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Pro Phe Asn Asn Phe Gly Ile Trp Phe Ala Tyr Trp Gly
            100                 105                 110

Gln Gly Thr Leu Val Thr Val Ser
            115                 120
```